(12) United States Patent
Sharma et al.

(10) Patent No.: US 9,623,238 B2
(45) Date of Patent: Apr. 18, 2017

(54) DEVICE AND IMPLANTATION SYSTEM FOR ELECTRICAL STIMULATION OF BIOLOGICAL SYSTEMS

(71) Applicant: Endostim, Inc., St. Louis, MO (US)

(72) Inventors: Virender K. Sharma, Paradise Valley, AZ (US); Shai Policker, Tenafly, NJ (US); Bevil Hogg, Soquel, CA (US)

(73) Assignee: Endostim, Inc., St. Louis, MO (US)

( * ) Notice: Subject to any disclaimer, the term of this patent is extended or adjusted under 35 U.S.C. 154(b) by 117 days.

(21) Appl. No.: 13/975,162

(22) Filed: Aug. 23, 2013

(65) Prior Publication Data

US 2014/0088664 A1   Mar. 27, 2014

Related U.S. Application Data

(60) Provisional application No. 61/692,555, filed on Aug. 23, 2012.

(51) Int. Cl.
*A61N 1/36* (2006.01)
*A61N 1/05* (2006.01)

(52) U.S. Cl.
CPC ....... *A61N 1/36003* (2013.01); *A61N 1/0517* (2013.01); *A61N 1/36007* (2013.01)

(58) Field of Classification Search
CPC .............. A61N 1/0517; A61N 1/36003; A61N 1/36007
See application file for complete search history.

(56) References Cited

U.S. PATENT DOCUMENTS

| | | |
|---|---|---|
| 3,909,883 A | 10/1975 | Fegen |
| 3,910,281 A | 10/1975 | Kletschka |
| 4,393,883 A | 7/1983 | Smyth |
| 4,414,986 A | 11/1983 | Dickhudt |
| 4,612,934 A | 9/1986 | Borkan |
| 4,735,205 A | 4/1988 | Chachques |
| 5,117,827 A | 6/1992 | Stuebe |
| 5,188,104 A | 2/1993 | Wernicke |
| 5,193,539 A | 3/1993 | Schulman |
| 5,197,491 A | 3/1993 | Anderson |
| 5,231,988 A | 8/1993 | Wernicke |
| 5,263,480 A | 11/1993 | Wernicke |

(Continued)

FOREIGN PATENT DOCUMENTS

| | | |
|---|---|---|
| CN | 1476339 | 2/2004 |
| CN | 1494451 A | 5/2004 |

(Continued)

OTHER PUBLICATIONS

Xing et al., 'Gastric Electrical Stimulation Significantly Increases Canine Lower Esophageal Pressure' M1811 Cleveland, OH.

(Continued)

*Primary Examiner* — Joseph Dietrich
(74) *Attorney, Agent, or Firm* — Novel IP

(57) ABSTRACT

The present specification discloses devices and methodologies for the treatment of achalasia. Individuals with achalasia are treated by implanting a stimulation device within the patient's lower esophageal sphincter and applying electrical stimulation to the patient's lower esophageal sphincter, in accordance with certain predefined protocols. The presently disclosed devices have a simplified design because they do not require sensing systems capable of sensing when a person is engaged in a wet swallow and have improved energy storage requirements.

15 Claims, 14 Drawing Sheets

(56) References Cited

U.S. PATENT DOCUMENTS

| | | |
|---|---|---|
| 5,292,344 A | 3/1994 | Douglas |
| 5,360,428 A | 11/1994 | Hutchinson, Jr. |
| 5,423,872 A | 6/1995 | Cigaina |
| 5,531,778 A | 7/1996 | Maschino |
| 5,540,730 A | 7/1996 | Terry |
| 5,556,425 A | 9/1996 | Hewson |
| 5,649,902 A | 7/1997 | Yoon |
| 5,674,205 A | 10/1997 | Pasricha |
| 5,690,691 A | 11/1997 | Chen |
| 5,697,375 A | 12/1997 | Hickey |
| 5,709,224 A | 1/1998 | Behl |
| 5,716,385 A | 2/1998 | Mittal |
| 5,716,392 A | 2/1998 | Bourgeois |
| 5,810,810 A | 9/1998 | Tay |
| 5,836,994 A | 11/1998 | Bourgeois |
| 5,861,014 A | 1/1999 | Familoni |
| 5,861,044 A | 1/1999 | Crenshaw |
| 5,882,340 A | 3/1999 | Yoon |
| 5,893,883 A | 4/1999 | Torgerson |
| 5,935,126 A | 8/1999 | Riza |
| 5,995,872 A | 11/1999 | Bourgeois |
| 6,006,755 A | 12/1999 | Edwards |
| 6,026,326 A | 2/2000 | Bardy |
| 6,041,258 A | 3/2000 | Cigaina |
| 6,051,017 A | 4/2000 | Loeb |
| 6,091,992 A | 7/2000 | Bourgeois |
| 6,097,984 A | 8/2000 | Douglas |
| 6,216,039 B1 | 4/2001 | Bourgeois |
| 6,221,039 B1 | 4/2001 | Durgin |
| 6,243,607 B1 | 6/2001 | Mintchev |
| 6,254,598 B1 | 7/2001 | Edwards |
| 6,285,897 B1 | 9/2001 | Kilcoyne |
| 6,321,124 B1 | 11/2001 | Cigaina |
| 6,360,130 B1 | 3/2002 | Duysens |
| 6,381,495 B1 | 4/2002 | Jenkins |
| 6,449,511 B1 | 9/2002 | Mintchev |
| 6,510,332 B1 | 1/2003 | Greenstein |
| 6,542,776 B1 | 4/2003 | Gordon |
| 6,571,127 B1 | 5/2003 | Ben-Haim |
| 6,587,719 B1 | 7/2003 | Barrett |
| 6,591,137 B1 | 7/2003 | Fischell |
| 6,611,715 B1 | 8/2003 | Boveja |
| 6,612,983 B1 | 9/2003 | Marchal |
| 6,615,084 B1 | 9/2003 | Cigaina |
| 6,678,561 B2 | 1/2004 | Forsell |
| 6,684,104 B2 | 1/2004 | Gordon |
| 6,749,607 B2 | 6/2004 | Edwards |
| 6,754,536 B2 | 6/2004 | Swoyer |
| 6,760,626 B1 | 7/2004 | Boveja |
| 6,826,428 B1 | 11/2004 | Chen |
| 6,832,114 B1 | 12/2004 | Whitehurst |
| 6,853,862 B1 | 2/2005 | Marchal |
| 6,876,885 B2 | 4/2005 | Swoyer |
| 6,879,859 B1 | 4/2005 | Boveja |
| 6,879,861 B2 | 4/2005 | Benz |
| 6,901,295 B2 | 5/2005 | Sharma |
| 6,915,165 B2 | 7/2005 | Forsell |
| 6,947,792 B2 | 9/2005 | Ben-Haim |
| 6,952,613 B2 | 10/2005 | Swoyer |
| 7,006,871 B1 | 2/2006 | Darvish |
| 7,016,735 B2 | 3/2006 | Imran |
| 7,054,689 B1 | 5/2006 | Whitehurst |
| 7,054,690 B2 | 5/2006 | Imran |
| 7,076,305 B2 | 7/2006 | Imran |
| 7,076,306 B2 | 7/2006 | Marchal |
| 7,087,053 B2 | 8/2006 | Vanney |
| 7,114,502 B2 | 10/2006 | Schulman |
| 7,120,498 B2 | 10/2006 | Imran |
| 7,146,216 B2 | 12/2006 | Bumm |
| 7,167,750 B2 | 1/2007 | Knudson |
| 7,177,693 B2 | 2/2007 | Starkebaum |
| 7,200,443 B2 | 4/2007 | Faul |
| 7,203,551 B2 | 4/2007 | Houben |
| 7,263,405 B2 | 8/2007 | Boveja |
| 7,299,091 B2 | 11/2007 | Barrett |
| 7,310,557 B2 | 12/2007 | Maschino |
| 7,340,306 B2 | 3/2008 | Barrett |
| 7,343,201 B2 | 3/2008 | Mintchev |
| 7,363,084 B2 | 4/2008 | Kurokawa |
| 7,444,183 B2 | 10/2008 | Knudson |
| 7,477,994 B2 | 1/2009 | Sunshine |
| 7,519,431 B2 | 4/2009 | Goetz |
| 7,519,433 B2 | 4/2009 | Foley |
| 7,558,629 B2 | 7/2009 | Keimel |
| 7,593,777 B2 | 9/2009 | Gerber |
| 7,599,736 B2 | 10/2009 | DiLorenzo |
| 7,620,454 B2 | 11/2009 | Dinsmoor |
| 7,664,551 B2 | 2/2010 | Cigaina |
| 7,676,270 B2 | 3/2010 | Imran |
| 7,702,394 B2 | 4/2010 | Imran |
| 7,702,395 B2 | 4/2010 | Towe |
| 7,711,437 B1 | 5/2010 | Bornzin |
| 7,720,539 B2 | 5/2010 | Mintchev |
| 7,729,771 B2 | 6/2010 | Knudson |
| 7,734,355 B2 | 6/2010 | Cohen |
| 7,738,961 B2 | 6/2010 | Sharma |
| 7,742,818 B2 | 6/2010 | Dinsmoor |
| 7,794,425 B2 | 9/2010 | Gobel |
| 7,813,809 B2 | 10/2010 | Strother |
| 7,835,796 B2 | 11/2010 | Maschino |
| 7,848,802 B2 | 12/2010 | Goetz |
| 7,899,540 B2 | 3/2011 | Maschino |
| 7,914,468 B2 | 3/2011 | Shalon |
| 7,941,221 B2 | 5/2011 | Foley |
| 7,957,807 B2 | 6/2011 | Starkebaum |
| 7,962,214 B2 | 6/2011 | Byerman |
| 7,983,755 B2 | 7/2011 | Starkebaum |
| 8,135,470 B2 | 3/2012 | Keimel |
| 8,155,758 B2 | 4/2012 | Roline |
| 8,160,709 B2 | 4/2012 | Soffer |
| 8,185,206 B2 | 5/2012 | Starkebaum |
| 8,282,561 B2 | 10/2012 | Towe |
| 8,380,321 B2 | 2/2013 | Goetz |
| 8,406,868 B2 | 3/2013 | Buschman |
| 8,423,134 B2 | 4/2013 | Buschman |
| 8,447,403 B2 | 5/2013 | Sharma |
| 8,447,404 B2 | 5/2013 | Sharma |
| 8,452,407 B2 | 5/2013 | Whitehurst |
| 8,467,874 B2 | 6/2013 | Chen |
| 8,467,884 B2 | 6/2013 | Chen |
| 8,521,292 B2 | 8/2013 | Wei |
| 8,538,532 B2 | 9/2013 | Starkebaum |
| 8,538,534 B2 | 9/2013 | Soffer |
| 8,543,210 B2 | 9/2013 | Sharma |
| 8,556,952 B2 | 10/2013 | Shadduck |
| 8,594,811 B2 | 11/2013 | Chen |
| 8,712,529 B2 | 4/2014 | Sharma |
| 8,712,530 B2 | 4/2014 | Sharma |
| 8,761,903 B2 | 6/2014 | Chen |
| 8,792,986 B2 | 7/2014 | Cigaina |
| 8,831,737 B2 | 9/2014 | Wesselink |
| 8,892,217 B2 | 11/2014 | Camps |
| 9,020,597 B2 | 4/2015 | Sharma |
| 9,061,147 B2 | 6/2015 | Sharma |
| 2001/0041831 A1 | 11/2001 | Starkweather |
| 2002/0103522 A1 | 8/2002 | Swoyer |
| 2002/0138075 A1 | 9/2002 | Edwards |
| 2002/0161414 A1 | 10/2002 | Flesler |
| 2002/0165589 A1 | 11/2002 | Imran |
| 2003/0014086 A1 | 1/2003 | Sharma |
| 2003/0028226 A1 | 2/2003 | Thompson |
| 2003/0055463 A1 | 3/2003 | Gordon |
| 2003/0078633 A1 | 4/2003 | Firlik |
| 2003/0120321 A1 | 6/2003 | Bumm |
| 2003/0144708 A1 | 7/2003 | Starkebaum |
| 2003/0195600 A1 | 10/2003 | Tronnes |
| 2004/0012088 A1 | 1/2004 | Fukasawa |
| 2004/0015201 A1 | 1/2004 | Greenstein |
| 2004/0024428 A1 | 2/2004 | Barrett |
| 2004/0039427 A1 | 2/2004 | Barrett |
| 2004/0044376 A1 | 3/2004 | Flesler |
| 2004/0059393 A1 | 3/2004 | Policker |
| 2004/0073453 A1 | 4/2004 | Nenov |
| 2004/0088033 A1 | 5/2004 | Smits |

(56) References Cited

U.S. PATENT DOCUMENTS

| | | |
|---|---|---|
| 2004/0116977 A1 | 6/2004 | Finch |
| 2004/0138586 A1 | 7/2004 | Ganz |
| 2004/0147976 A1 | 7/2004 | Gordon |
| 2004/0167583 A1 | 8/2004 | Knudson |
| 2004/0172088 A1 | 9/2004 | Knudson |
| 2004/0186544 A1 | 9/2004 | King |
| 2004/0193229 A1 | 9/2004 | Starkebaum |
| 2004/0243182 A1 | 12/2004 | Cohen |
| 2005/0027328 A1 | 2/2005 | Greenstein |
| 2005/0049655 A1 | 3/2005 | Boveja |
| 2005/0065571 A1 | 3/2005 | Imran |
| 2005/0070974 A1 | 3/2005 | Knudson |
| 2005/0075678 A1 | 4/2005 | Faul |
| 2005/0090873 A1 | 4/2005 | Imran |
| 2005/0131486 A1 | 6/2005 | Boveja |
| 2005/0137480 A1 | 6/2005 | Alt |
| 2005/0137643 A1 | 6/2005 | Mintchev |
| 2005/0137644 A1 | 6/2005 | Boveja |
| 2005/0143787 A1 | 6/2005 | Boveja |
| 2005/0149141 A1 | 7/2005 | Starkebaum |
| 2005/0149142 A1 | 7/2005 | Starkebaum |
| 2005/0149146 A1 | 7/2005 | Boveja |
| 2005/0222637 A1 | 10/2005 | Chen |
| 2005/0222638 A1 | 10/2005 | Foley |
| 2005/0245788 A1 | 11/2005 | Gerber |
| 2005/0251219 A1 | 11/2005 | Evans |
| 2006/0004304 A1 | 1/2006 | Parks |
| 2006/0015162 A1 | 1/2006 | Edward |
| 2006/0036293 A1 | 2/2006 | Whitehurst |
| 2006/0064037 A1 | 3/2006 | Shalon |
| 2006/0074459 A1 | 4/2006 | Flesler |
| 2006/0095077 A1 | 5/2006 | Tronnes |
| 2006/0106442 A1 | 5/2006 | Richardson |
| 2006/0116736 A1 | 6/2006 | DiLorenzo |
| 2006/0167498 A1 | 7/2006 | DiLorenzo |
| 2006/0200217 A1 | 9/2006 | Wessman |
| 2006/0206160 A1 | 9/2006 | Cigaina |
| 2006/0218011 A1 | 9/2006 | Walker |
| 2006/0247717 A1 | 11/2006 | Starkebaum |
| 2006/0247718 A1 | 11/2006 | Starkebaum |
| 2006/0247722 A1 | 11/2006 | Maschino |
| 2006/0265021 A1 | 11/2006 | Herbert |
| 2007/0016274 A1 | 1/2007 | Boveja |
| 2007/0049793 A1 | 3/2007 | Ignagni |
| 2007/0060955 A1 | 3/2007 | Strother |
| 2007/0060968 A1 | 3/2007 | Strother |
| 2007/0060979 A1 | 3/2007 | Strother |
| 2007/0066995 A1 | 3/2007 | Strother |
| 2007/0067000 A1 | 3/2007 | Strother |
| 2007/0100388 A1 | 5/2007 | Gerber |
| 2007/0106337 A1 | 5/2007 | Errico |
| 2007/0106338 A1 | 5/2007 | Errico |
| 2007/0142699 A1 | 6/2007 | Jandrall |
| 2007/0142831 A1 | 6/2007 | Shadduck |
| 2007/0142884 A1 | 6/2007 | Jandrall |
| 2007/0156182 A1 | 7/2007 | Castel |
| 2007/0162084 A1 | 7/2007 | Chen |
| 2007/0162085 A1 | 7/2007 | DiLorenzo |
| 2007/0179542 A1 | 8/2007 | Prakash |
| 2007/0238942 A1 | 10/2007 | Baylor |
| 2007/0239248 A1 | 10/2007 | Hastings |
| 2007/0244375 A1 | 10/2007 | Jenkins |
| 2007/0255118 A1 | 11/2007 | Miesel |
| 2007/0255335 A1 | 11/2007 | Herbert |
| 2007/0255336 A1 | 11/2007 | Herbert |
| 2007/0255352 A1 | 11/2007 | Roline |
| 2007/0265662 A1 | 11/2007 | Ufford |
| 2007/0265666 A1 | 11/2007 | Roberts |
| 2007/0265668 A1 | 11/2007 | Reinke |
| 2007/0265671 A1 | 11/2007 | Roberts |
| 2007/0265674 A1 | 11/2007 | Olson |
| 2007/0282410 A1 | 12/2007 | Cross |
| 2008/0021512 A1 | 1/2008 | Knudson |
| 2008/0039904 A1 | 2/2008 | Bulkes |
| 2008/0046062 A1 | 2/2008 | Camps |
| 2008/0058836 A1 | 3/2008 | Moll |
| 2008/0058891 A1 | 3/2008 | Ben-Haim |
| 2008/0086179 A1 | 4/2008 | Sharma |
| 2008/0132968 A1 | 6/2008 | Starkebaum |
| 2008/0147137 A1 | 6/2008 | Cohen |
| 2008/0154191 A1 | 6/2008 | Gobel |
| 2008/0183238 A1 | 7/2008 | Chen |
| 2008/0195171 A1 | 8/2008 | Sharma |
| 2008/0208355 A1 | 8/2008 | Stack |
| 2009/0012421 A1 | 1/2009 | Bek |
| 2009/0018617 A1 | 1/2009 | Skelton |
| 2009/0018619 A1 | 1/2009 | Skelton |
| 2009/0020406 A1 | 1/2009 | Nirmalakhandan |
| 2009/0030475 A1 | 1/2009 | Brynelsen |
| 2009/0069803 A1 | 3/2009 | Starkebaum |
| 2009/0076498 A1 | 3/2009 | Saadat |
| 2009/0088817 A1 | 4/2009 | Starkebaum |
| 2009/0131993 A1 | 5/2009 | Rousso |
| 2009/0132001 A1 | 5/2009 | Soffer |
| 2009/0187223 A1 | 7/2009 | Gross |
| 2009/0204063 A1 | 8/2009 | Policker |
| 2009/0264951 A1 | 10/2009 | Sharma |
| 2009/0281553 A1 | 11/2009 | Kalloo |
| 2010/0004648 A1 | 1/2010 | Edwards |
| 2010/0049026 A1 | 2/2010 | Gerber |
| 2010/0057085 A1 | 3/2010 | Holcomb |
| 2010/0069789 A1 | 3/2010 | Hirota |
| 2010/0076345 A1 | 3/2010 | Soffer |
| 2010/0170812 A1 | 7/2010 | Odierno |
| 2010/0198039 A1 | 8/2010 | Towe |
| 2010/0324432 A1 | 12/2010 | Bjoerling |
| 2011/0004266 A1 | 1/2011 | Sharma |
| 2011/0046653 A1 | 2/2011 | Addington |
| 2011/0071589 A1 | 3/2011 | Starkebaum |
| 2011/0213437 A9 | 9/2011 | Armstrong |
| 2011/0224665 A1 | 9/2011 | Crosby |
| 2011/0295335 A1 | 12/2011 | Sharma |
| 2011/0295336 A1 | 12/2011 | Sharma |
| 2011/0307027 A1 | 12/2011 | Sharma |
| 2011/0307028 A1 | 12/2011 | Sharma |
| 2012/0232610 A1 | 9/2012 | Soffer |
| 2012/0259389 A1 | 10/2012 | Starkebaum |
| 2012/0265103 A1 | 10/2012 | Policker |
| 2012/0277619 A1 | 11/2012 | Starkebaum |
| 2013/0030503 A1 | 1/2013 | Yaniv |
| 2013/0035740 A1 | 2/2013 | Sharma |
| 2013/0072928 A1 | 3/2013 | Schaer |
| 2013/0090551 A1 | 4/2013 | Sharma |
| 2013/0178912 A1 | 7/2013 | Sharma |
| 2013/0218229 A1 | 8/2013 | Sharma |
| 2013/0231660 A1 | 9/2013 | Edwards |
| 2013/0238048 A1 | 9/2013 | Almendinger |
| 2014/0012348 A1 | 1/2014 | Starkebaum |
| 2014/0018657 A1 | 1/2014 | Sharma |
| 2014/0088664 A1 | 3/2014 | Sharma |
| 2014/0088666 A1 | 3/2014 | Goetz |
| 2014/0135886 A1 | 5/2014 | Cook |
| 2014/0222106 A1 | 8/2014 | Sharma |
| 2014/0228911 A1 | 8/2014 | Sharma |
| 2014/0243593 A1 | 8/2014 | Goode |
| 2015/0045786 A1 | 2/2015 | Edwards |
| 2015/0119952 A1 | 4/2015 | Sharma |
| 2016/0001071 A1 | 1/2016 | Sharma |

FOREIGN PATENT DOCUMENTS

| | | |
|---|---|---|
| CN | 102725021 | 10/2012 |
| EP | 1004330 | 5/2000 |
| WO | 9853878 | 12/1998 |
| WO | 9903532 | 1/1999 |
| WO | 9930776 | 6/1999 |
| WO | 0061223 | 10/2000 |
| WO | 0061223 A1 | 10/2000 |
| WO | 0061224 | 10/2000 |
| WO | 0061224 A1 | 10/2000 |
| WO | 0243467 | 6/2002 |
| WO | 0243467 A2 | 6/2002 |
| WO | 02089655 | 11/2002 |
| WO | 2005051486 A1 | 9/2005 |

(56) References Cited

FOREIGN PATENT DOCUMENTS

| WO | 2007137026 | | 11/2007 |
|---|---|---|---|
| WO | 2009009276 | | 1/2009 |
| WO | 2009114008 | A1 | 9/2009 |
| WO | 2010027963 | | 3/2010 |
| WO | 2010135634 | | 11/2010 |
| WO | 2012151449 | | 11/2012 |
| WO | 2014032030 | | 2/2014 |
| WO | 2015034867 | | 3/2015 |
| WO | 2015077425 | | 5/2015 |
| WO | 2015077435 | | 5/2015 |

OTHER PUBLICATIONS

Xing et al, 'Gastric Electrical Stimulation (GES) with Parameters for Morbid Obesity Elevates Lower Esophageal Sphincter (LES) Pressure in Conscious Dogs'; Obesity Surgery; 15; 2005; pp. 1321-1327.
Cigaina, Valerio; Long-term Follow-Up of Gastric Stimulation for Obesity: The Mestre 8-Year Experience; Obesity Surgery; 14; 2004; S14-22.
Xing et al, 'Gastric Electrical Stimulation Significantly Increases Canine Lower Esophageal Sphincter Pressure'; Digestive Diseases and Sciences; vol. 50, No. 8 (Aug. 2005), pp. 1481-1487.
Sanmiguel et al, 'Effect of electrical stimulation of the LES on LES pressure in a canine model'; Am J Physiol Gastrointest Live Physiol; 295: 389-394; 2008.
Clarke et al,. 'An Endoscopic Implantable Device Stimulates the LES On-Demand by Remote Control in a Canine Model'; Gastrointestinal Endoscopy, vol. 63, No. 5; 2006, AB103, 759.
Kantsevoy et al., 'An Endoscopically Implantable On-Demand Stimulator Is Successful in Increasing Lower Esophageal Sphincter Pressure in a Porcine Model'; Gastrointestinal Endoscopy, vol. 61, No. 5: 2005, AB79, 222.
Christensen et al., 'Physiologic Specialization at Esophagogastric Junction in Three Species', American Journal of Physiology, vol. 225, No. 6, Dec. 1973, 1265-1270.
Ellis, et al., 'The Prevention of Experimentally Induced Reflux by Electrical Stimulation of the Distal Esophagus', American Journal of Surgery, vol. 115, Apr. 1968, 482-487.
Gonzalez et al., 'Different Responsiveness of Excitatory and Inhibitory Enteric Motor Neurons in the Human Esophagus to Electrical Field Stimulation and to Nicotine', Am J Physiol Gastrointest Liver Physiol, 287:G299-G306, 2004.
Kahrilas et al., 'Impact of Fundoplication on Bolus Transit Across Esophagogastric Junction', American Physiological Society, 1998, 1386-1393.
Kamath et al., 'Neurocardiac and Cerebral Responses Evoked by Esophageal Vago-Afferent Stimulation in Humans: Effects of Varying Intensities', Cardiovascular Research, 40 (1998) 591-599.
Lund et al., 'Electrical Stimulation of Esophageal Smooth Muscle and Effects of Antagonists', American Journal of Physiology, vol. 217, No. 5, Nov. 1969, 1369-1374.
Stein et al., 'Three-dimensional Imaging of the Lower Esophageal Sphincter in Gastroesophageal Reflux Disease,' Annual Meeting of the American Surgical Association, Apr. 11-13, 1991, 374-383.
International Search Report for PCT/US2007/068907, Aug. 7, 2008.
International Search Report for PCT/US2012/036408, Aug. 17, 2012.
Summary of Neurostimulation Systems Features, Advanced Neuromodulation Systems (ANS) home page, accessed on May 31, 2007 at http://web.archive.org/web/20040211224857/www.ans-medical.com/patients/WhichSystemIsBest/SumOfNeurostimulation.html.
International Search Report for PCT/US2008/053780, Jun. 8, 2009.
International Search Report for PCT/US2008/056479, Aug. 20, 2008.
International Search Report for PCT/US2011/027243, Jul. 8, 2011.
International Search Report for PCT/US12/053576, Dec. 24, 2012.
International Search Report for PCT/US2012/033695, Aug. 7, 2012.

EPO Search Report EP09704463, Jan. 10, 2011, Virender K. Sharma.
International Search Report for PCT/US2013/056520, Apr. 4, 2014.
Clarke et al., 'An endoscopically implantable device stimulates the lower esophageal sphincter on demand by remote control: a study using a canine model', Endoscopy 2007; 39: 72-76.
Sallam et al, 'Feasibility of gastric electrical stimulation by percutaneous endoscopic transgastric electrodes'; Gastrointestinal Endoscopy; vol. 68, No. 4; 2008, 754-759.
Notice of Allowance dated Feb. 20, 2015 for U.S. Appl. No. 14/201,645.
Office Action dated Feb. 20, 2015 for U.S. Appl. No. 14/175,927.
First Office Action for Application No. CN 01819456, dated Nov. 18, 2014.
Office Action dated Apr. 11, 2014 for U.S. Appl. No. 13/602,184.
Notice of Allowance dated Jul. 21, 2014 for U.S. Appl. No. 13/447,168.
Notice of Allowance dated Apr. 3, 2014 for U.S. Appl. No. 13/447,168.
Notice of Allowance dated Mar. 17, 2014 for U.S. Appl. No. 13/447,168.
Office Action dated Jul. 8, 2014 for U.S. Appl. No. 13/463,803.
Shellock, Frank G. 'RF Bion Microstimulator' MRISafety.com, http://www.mrisafety.com/SafetyInfov.asp?SafetyInfoID=254, Shellock R & D Services, Inc. and Frank G. Shellock, Ph.D., 4 pages, 2014.
Notice of Allowance dated Dec. 24, 2014 for U.S. Appl. No. 13/463,803.
Supplementary European Search Report for EP20120779639, Virender K. Sharma, Nov. 13, 2014.
European Search Opinion for EP20120779639, Virender K. Sharma, Nov. 25, 2014.
Notice of Allowance dated Jan. 20, 2015 for U.S. Appl. No. 13/602,184.
Office Action dated Jun. 25, 2015 for U.S. Appl. No. 14/201,766.
Examination Report for Australian Patent Application No. 2012242533, Oct. 5, 2015.
Examination Report for Australian Patent Application No. 2012250686, Nov. 4, 2015.
Examination Report for New Zealand Patent Application No. 616944, Jun. 17, 2014.
Examination Report for New Zealand Patent Application No. 616944, Nov. 2, 2015.
Extended European Search Report for EPO Application No. 12771852.6, Aug. 28, 2014.
First Office Action for Chinese Patent Application No. 201380054290.1, Apr. 1, 2016.
International Search Report for PCT/US2014/053793, Mar. 27, 2015.
International Search Report for PCT/US2014/066565, Mar. 12, 2015.
International Search Report for PCT/US2014/066578, Mar. 19, 2015.
Jameison, GG et al. "Laparoscopic Nissen Fundoplication". Annals of Surgery, vol. 220. No. 2, p. 139 (1994).
Notice of Allowance date Jan. 20, 2016 for U.S. Appl. No. 14/201,766.
Office Action dated Feb. 1, 2016 for U.S. Appl. No. 14/475,736.
Office Action dated Mar. 10, 2016 for U.S. Appl. No. 14/191,085.
Office Action dated Oct. 2, 2015 for U.S. Appl. No. 14/500,856.
Office Action for Chinese Patent Application No. 201280028867.7, May 4, 2015.
Second Office Action for Chinese Patent Application No. 201280028867.7, dated Mar. 21, 2016.
Tam, WCE et al. "Delivery of radiofrequency energy to the lower esophageal sphincter and gastric cardia inhibits transient oesophageal sphincter relaxations and gastro-oesophageal reflux in patients with reflux disease". Gut, 52(4), 479-785 (2003).
Office Action dated Jun. 8, 2016 for U.S. Appl. No. 14/475,736.
Office Action dated Mar. 15, 2016 for U.S. Appl. No. 14/695,267.
Office Action dated Mar. 17, 2016 for U.S. Appl. No. 14/500,856.
Office Action dated May 4, 2016 for U.S. Appl. No. 14/548,793.

(56) References Cited

OTHER PUBLICATIONS

Notice of Allowance date Jul. 19, 2016 for U.S. Appl. No. 14/191,085.
Supplementary European Search Report for EP13831668, completed on Apr. 15, 2016.

- Lead Placement Combinations
  - AB
  - AB or CD
  - AC / BD Alternating
  - AB / CD Alternating
  - AB Vs. CD

DEVICE AND IMPLANTATION SYSTEM FOR ELECTRICAL STIMULATION OF BIOLOGICAL SYSTEMS

CROSS-REFERENCE

The present application relies on U.S. Provisional Patent Application No. 61/692,555, entitled "Device and Implantation System for Electrical Stimulation of Biological Systems" and filed on Aug. 23, 2012, for priority. The aforementioned application is herein incorporated by reference.

FIELD

The present specification relates generally to a method and apparatus for electrical stimulation of biological systems. More particularly, the present specification relates to a method and apparatus for treating achalasia by electrically stimulating a portion of the gastrointestinal system.

BACKGROUND

Achalasia is a motility disorder of the esophagus wherein a frequently hypertensive lower esophageal sphincter (LES) fails to completely relax accompanied with a lack of peristalsis in the tubular esophagus. The major symptom of patients suffering from achalasia is difficulty swallowing (dysphagia). Other common symptoms include stagnation of swallowed solids and liquids (stasis), regurgitation, weight loss, chest pain, nocturnal cough, and secondary respiratory complications. Although the exact cause of achalasia is unknown, recent studies have suggested that achalasia is an autoimmune disease triggered by some insult, perhaps a virus, in individuals genetically susceptible to the disease. Left untreated, achalasia can worsen and complications include pulmonary disease secondary to chronic aspiration, megaesophagus, and cancer.

Individuals exhibiting symptoms of achalasia are often diagnosed through imaging studies (ultrasound and barium esophagogram), manometry, esophagogastroduodenoscopy (EGD), manometry, and high resolution manometry (HRM) with pressure topography plotting. Elevated LES pressure on manometry, aperistalsis of the smooth muscle of the esophagus, and incomplete relaxation of the LES are the most common features of classic achalasia. Achalasia is considered the antithesis of gastroesophageal reflux disease (GERD), as patients suffering from achalasia exhibit elevated LES pressures and increased LES tone while those with GERD have decreased LES pressures and decreased LES tone. However, patients with achalasia do sometimes experience reflux symptoms, possibly due to retention of acidic food contents or bacterial overgrowth with resultant lactate production in the esophagus.

Since an exact cause is not known, current treatment modalities for achalasia are targeted at relieving symptoms. These treatments include pharmacologic therapy, endoscopy, and surgery. Pharmacologic therapies act to treat achalasia by reducing LES pressure through the use of smooth muscle relaxants. Common medications include calcium channel blockers, nitrates, and phosphodiesterase 5 inhibitors. These are taken shortly before meals and provide limited LES relaxation. Unfortunately, patients still often complain of dysphagia despite relaxation of the LES. In addition, pharmacologic agents have a short duration of action and their use is associated with a large number of side effects. As such, pharmacologic therapy is mostly intended for patients with a new onset of achalasia or for those who are awaiting more long term treatment.

Endoscopic therapies available in the treatment of achalasia include pneumatic dilation of the LES and botulinum toxin injection into the LES. Pneumatic dilation involves passing an inflatable balloon into the patient's mouth and advancing it to the LES, at which point the balloon is inflated with the desired result being disruption of the LES. Pneumatic dilation has been considered the most effective non-surgical treatment of achalasia. However, pneumatic dilation runs the risk of esophageal perforation and studies show symptoms of achalasia return in approximately 50% of patients after 15 years.

Botulinum toxin injection involves injecting a small amount of botulinum toxin into the area of the LES of the affected patient. The neurotoxin blocks the release of acetylcholine from excitatory neurons, resulting in relaxation of the LES. For example, U.S. Pat. No. 5,437,291, assigned to Allergan, Inc., describes a "method for in vivo treatment of smooth muscle disorders of a mammal, comprising: injecting directly into a smooth muscle in a mammal an amount of a neurotoxin which inhibits neurotransmitter release from nerve terminals." In addition, U.S. Pat. No. 8,025,889, assigned to Patricia S. Walker, describes a "method for treating a condition in a patient in need thereof, the method comprising the step of locally administering a therapeutically effective amount of a botulinum toxin in powder form to the patient using a needleless injector, wherein the condition is selected from the group consisting of spasmodic dysphonia, laryngeal dystonia, oromandibular dysphonia, lingual dystonia, cervical dystonia, focal hand dystonia, blepharospasm, strabismus, hemifacial spasm, eyelid disorder, cerebral palsy, focal spasticity, spasmodic colitis, neurogenic bladder, anismus, limb spasticity, tics, tremors, bruxism, anal fissure, achalasia, fibromyalgia, dysphagia, lacrimation, hyperhydrosis, excessive salivation, excessive gastrointestinal secretions, excessive mucous secretion, pain from muscle spasms, headache pain, brow furrows and skin wrinkles, whereby a symptom of the condition is thereby alleviated within 1 to 7 days."

Although botulinum toxin injections have been shown to be safe, 50% of patients have recurrence of symptoms after one year and nearly all patients have recurrence of symptoms after two years. Therefore, repeated treatments are often necessary to treat symptoms.

Surgical options for treating achalasia include myotomy and subtotal esophageal resection. Perforation is a risk associated with LES myotomy, and, although prognosis is quite good following the treatment, many patients suffer from severe GERD post-surgery. Therefore, a fundoplication is included with most myotomy procedures. A laparoscopic Heller myotomy with some type of fundoplication has become the preferred and most effective surgical therapy. However, some patients continue to experience GERD and require additional anti-reflux therapies. Subtotal esophageal resection with gastric pull-up is typically reserved for patients who do not respond to any other treatment. While effective, this procedure is extremely invasive and is associated with a high post-operative morbidity.

Therefore, a need exists for a safe, minimally invasive therapy for achalasia with high long-term efficacy. What is also needed is a treatment for achalasia that is not associated with the numerous side effects encountered with prior art therapies.

Hiatal hernia formation and recurrence is commonly encountered in patients suffering from gastroesophageal reflux disease (GERD). A hiatal hernia is a protrusion of a portion of the stomach through the diaphragm and up into the thorax. Patients having a hiatal hernia experience discomfort associated with reflux of stomach contents as the hiatal hernia impairs the function of the lower esophageal sphincter. Therefore, there is a need for a device and a method for treating GERD that would also prevent the formation or recurrence of a hiatal hernia.

Esophageal foreshortening is an occurrence seen in patients with GERD in which the length of the esophagus shortens and the gastroesophageal junction (GEJ) is briefly pulled upward into the thorax. In a manner similar to that seen with a hiatal hernia, esophageal foreshortening impairs the function of the LES by interfering with its complete closure. This results in decreased competency of the gastroesophageal barrier and leads to GERD. Esophageal foreshortening is also believed to be partly responsible for transient LES relaxations (TLESRs). TLESRs are brief episodes of reflux caused by the loss of LES tone. Esophageal shortening can cause migration of the GEJ into the thorax and, when immediately followed by relaxation of the LES, can result in the reflux of stomach contents back into the esophagus. Therefore, there is a need for a device and a method for treating GERD that would also prevent esophageal foreshortening.

SUMMARY

The present specification is directed toward a method for treating achalasia in a patient, comprising: incising the lower esophageal sphincter muscle of said patient to eliminate tone of said lower esophageal sphincter muscle; providing a device comprising at least one electrode operably connected to a pulse generator and an energy source, wherein said device is adapted to apply electrical stimulation to a target tissue; implanting said device within the upper gastrointestinal tract of the patient, wherein said at least one electrode is positioned proximate a portion of said lower esophageal sphincter muscle of said patient; and, operating said device to apply electrical stimulation to said lower esophageal sphincter muscle to modulate function of said lower esophageal sphincter muscle.

The present specification is also directed toward a method for treating esophageal dysfunction in a patient, comprising: providing a device comprising at least one electrode operably connected to a pulse generator, and an energy source, said device adapted to apply electrical stimulation to a target tissue; implanting said device within the upper gastrointestinal tract of the patient, wherein said at least one electrode is positioned proximate a portion of esophageal tissue of the patient; and, operating said device to apply electrical stimulation to said esophageal tissue to effectuate a decrease in lower esophageal sphincter (LES) resting tone and pressure.

In one embodiment, the electrical stimulation applied to the esophageal tissue further effectuates an increase in peristaltic activity within the esophageal body.

In one embodiment, the esophageal dysfunction comprises any one or more of achalasia, pain with swallowing, stasis, and/or regurgitation. In one embodiment, said esophageal tissue comprises any one or more of the proximal, mid, distal esophagus and/or LES.

In one embodiment, said operation defines, uses, or is dependent upon a plurality of stimulation parameters that determine the application of electrical stimulation to the patient's esophageal tissue and wherein said stimulation parameters are selected, derived, obtained, calculated, or determined, at least in part, to avoid esophageal muscle fatigue and tolerance.

In another embodiment, said operation defines, uses, or is dependent upon a plurality of stimulation parameters that determine the application of electrical stimulation to the patient's esophageal tissue and wherein said stimulation parameters are selected, derived, obtained, calculated, or determined, at least in part, to account for a latent, delayed, time-delayed, or future response of the patient's lower esophageal sphincter.

In one embodiment, said operation is initiated prior to a pre-defined point in time wherein said pre-defined point in time is associated with an achalasia triggering event and wherein said initiation occurs prior to said pre-defined point in time by a minimum time period. In various embodiments, said minimum time period is at least 5 minutes, 10 minutes, 15 minutes, 30 minutes, 1 hour, 2 hours, 3 hours, 12 hours, 24 hours, or any time increment therein. In one embodiment, electrical stimulation is terminated after said pre-defined point in time has passed. In one embodiment, operation is performed in accordance with a preset period and said preset period is not dependent upon, influenced by, modified by, lengthened by, or shortened by a physiological state of a patient. In one embodiment, said operation is performed in accordance with at least one on period, wherein said on period is between 1 second and 24 hours and at least one off period, wherein said off period is greater than 10 seconds.

In one embodiment, the method for treating esophageal dysfunction in a patient further comprises: providing a sensor capable of sensing and reporting a physiological parameter of the patient; implanting said sensor within the upper gastrointestinal tract; and, adjusting said electrical stimulation based upon sensed data from said sensor. In various embodiments, the physiological parameter comprises any one or more of LES pressure, esophageal pressure, patient position, esophageal temperature, gastrointestinal muscle tone or impedance, peristaltic activity, esophageal peristalsis, esophageal pH, esophageal impedance, esophageal electrical activity, gastric peristalsis, gastric electrical activity, gastric chemical activity, gastric hormonal activity, gastric temperature, gastric impedance, electrical activity, gastric pH, blood chemical and hormonal activity, vagal or other gastrointestinal neural activity and salivary chemical activity.

In one embodiment, the current of electrical stimulation from said at least one electrode ranges from greater than or equal to 8 mAmp to less than or equal to 1 Amp. In one embodiment, the pulse duration of electrical stimulation from said at least one electrode ranges from greater than or equal to 100 μsec to less than or equal to 1 second.

The present specification is also directed toward a method of programming an electrical stimulator wherein said stimulator is implanted proximate a lower esophageal sphincter of a patient, comprising: applying an energy input to said stimulator to cause said stimulator to stimulate the lower esophageal sphincter; monitoring a pressure level of said lower esophageal sphincter while said energy input is being applied to said stimulator; recording a time when the pressure level of said lower esophageal sphincter drops below a first threshold value; terminating said energy input to said stimulator when the pressure level of said lower esophageal sphincter drops below said first threshold value; monitoring the pressure level of said lower esophageal sphincter after terminating said energy input to said stimulator; recording a time when the pressure level of said lower esophageal sphincter reaches a second threshold value; and, programming said stimulator to operate for a fixed, preset period based on said recorded time.

The present specification is also directed toward a method of programming an electrical stimulator wherein said stimulator is implanted proximate a lower esophageal sphincter of a patient, comprising: applying an energy input to said stimulator to cause said stimulator to stimulate the lower esophageal sphincter; recording a first time and a first lead impedance value when said energy input is first applied to said stimulator; monitoring a pressure level of said lower esophageal sphincter while said energy input is being applied to said stimulator; recording a second time when the pressure level of said lower esophageal sphincter drops below a first threshold value; recording a second lead impedance value when the pressure level of said lower esophageal sphincter drops below said first threshold value; terminating said energy input to said stimulator when the pressure level of said lower esophageal sphincter drops below said first threshold value; monitoring the pressure level of said lower esophageal sphincter after terminating said energy input to said stimulator; recording a third time when the pressure level of said lower esophageal sphincter reaches a second threshold value; recording a third lead impedance value when the pressure level of said lower esophageal sphincter reaches said second threshold value; and, programming said stimulator to operate for a fixed, preset period based on said third recorded time.

The present specification is also directed toward a system for treating esophageal dysfunction in a patient, comprising: a pulse generator in electrical communication with at least one electrode, wherein said pulse generator is implanted within the upper gastrointestinal tract and said at least one electrode is positioned proximate the proximate, mid, distal esophagus and/or lower esophageal sphincter (LES), further wherein said pulse generator with said at least one electrode provide electrical stimulation to the esophagus to effectuate a decrease in LES tone and pressure and/or an increase in esophageal peristalsis; a controller module wired or wirelessly connected to said pulse generator, said controller module capable of receiving, storing and transmitting programmatic instructions directed toward the operation of said pulse generator; and, an energy storage component, wherein said energy storage component is integrated with said pulse generator or with said controller module, is independently implanted within the patient, or, is secured outside the patient against the patient's skin.

In one embodiment, the system for treating esophageal dysfunction in a patient further comprises: a sensor capable of sensing, and reporting to said controller module, a physiological parameter of the patient, wherein said physiological parameter comprises any one or more of LES pressure, esophageal pressure, patient position, esophageal temperature, gastrointestinal muscle tone or impedance, peristaltic activity, esophageal peristalsis, esophageal pH, esophageal impedance, esophageal electrical activity, gastric peristalsis, gastric electrical activity, gastric chemical activity, gastric hormonal activity, gastric temperature, gastric impedance, electrical activity, gastric pH, blood chemical and hormonal activity, vagal or other gastrointestinal neural activity and salivary chemical activity; further wherein said controller module adjusts said electrical stimulation based upon sensed data from said sensor.

In one embodiment, said esophageal dysfunction comprises any one or more of achalasia, pain with swallowing, stasis, and/or regurgitation.

The present specification is also directed toward a method of preventing a hiatal hernia in a patient with gastroesophageal reflux disease (GERD), comprising of the steps of: implanting a first, proximate end of a device in the lower esophageal sphincter of said patient and implanting a second end, opposite said first end, of said device in the anterior abdominal wall of said patient; wherein the device prevents the formation or recurrence of a hiatal hernia over time.

In one embodiment, there is a slack in the device of between 1 and 10 cm and, more preferably, between 2 and 5 cm, to allow for physiological movement in said lower esophageal sphincter. In various embodiments, the device has a tensile strength in a range of 1 to 100 newtons (N). In one embodiment, the device has a tensile strength of 20 N. In one embodiment, the device is made of a biocompatible material.

The present specification is also directed toward a method of preventing esophageal foreshortening in a patient with gastroesophageal reflux disease (GERD), comprising the steps of: a) implanting a first, proximate end of a device in the lower esophageal sphincter of said patient; and, b) implanting a second end, opposite said first end, of said device in the anterior abdominal wall of said patient, wherein the device interferes with foreshortening of the esophagus.

In one embodiment, there is a slack in said device of between 1 and 10 cm and, more preferably, between 2 and 5 cm, to allow for physiological movement in said lower esophageal sphincter. In various embodiments, the device has a tensile strength in a range of 1 to 100 newtons (N). In one embodiment, the device has a tensile strength of 20 N. In one embodiment, the device is made of a biocompatible material.

In one embodiment, the interference includes any one or combination of a reduction in the length of foreshortening, a reduction in the duration of foreshortening, a reduction in the number of foreshortening events, and a reduction in the number of foreshortening events associated with a reflux event. In one embodiment, the reduction in the length of foreshortening is at least 10%, the reduction in the duration of foreshortening is at least 10%, and/or the reduction in the number of foreshortening events either associated with a reflux event or not associated with a reflux event is at least 10%.

The aforementioned and other embodiments of the present specification shall be described in greater depth in the drawings and detailed description provided below.

BRIEF DESCRIPTION OF THE DRAWINGS

These and other features and advantages of the present specification will be further appreciated, as they become better understood by reference to the detailed description when considered in connection with the accompanying drawings.

DETAILED DESCRIPTION

Figure 1:
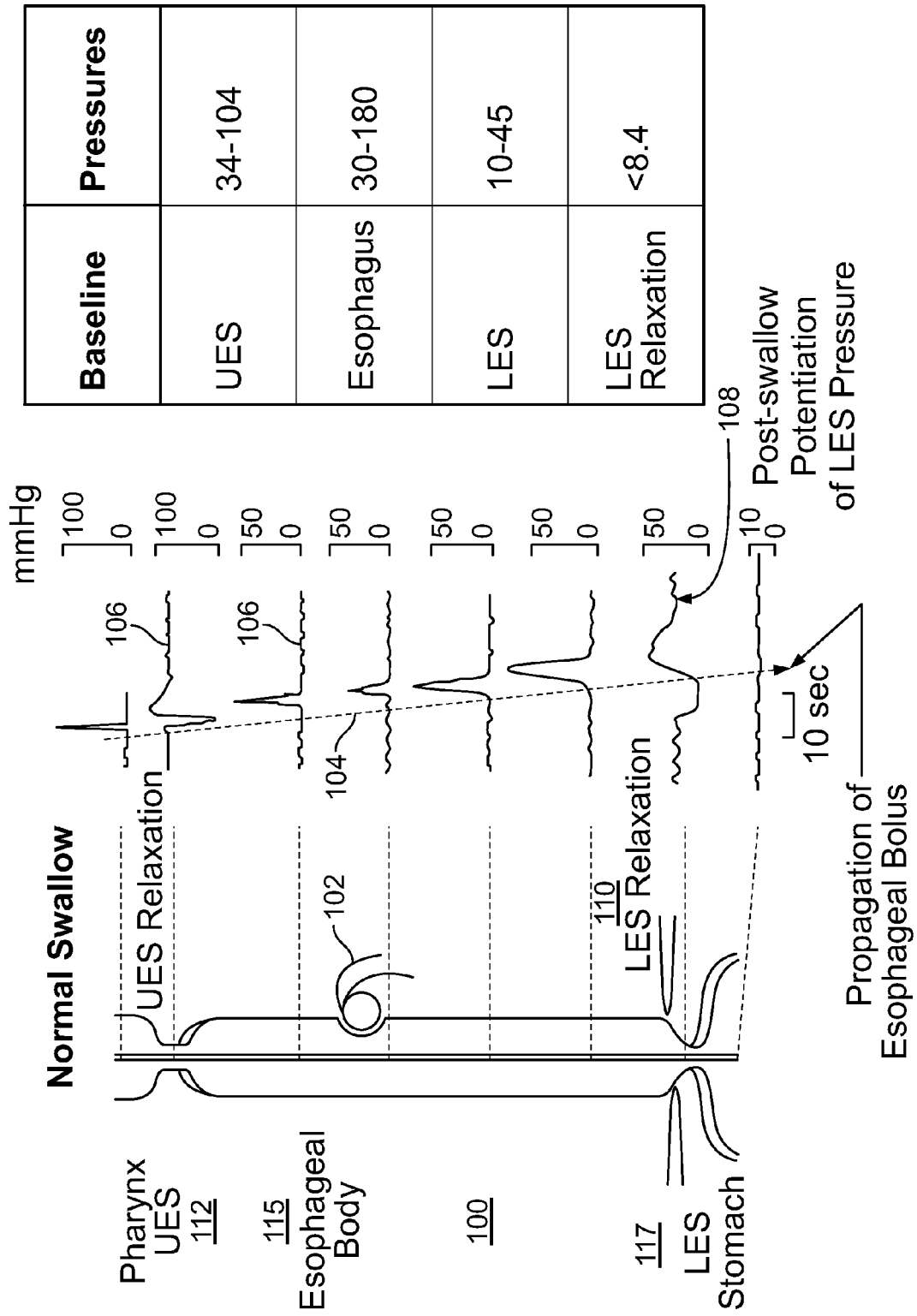
FIG. 1 is a graph depicting the physiology, including pressure measurements, of a normal swallow.

The present specification is directed toward a method and system of using programmable implantable electro-medical devices for the treatment of achalasia. The electro-medical devices of the present specification employ stimulators, including macrostimulators or microstimulators, which can be implanted with minimal invasiveness in the gastrointestinal system. Specifically, these devices can be beneficial for deep implant locations for which there is a natural orifice access providing closer proximity than from outside the body. It should further be appreciated that the devices are capable of stimulating all smooth muscle, not limited to GI smooth muscles and that the devices can additionally be used to deliver stimulation to the proximal stomach or area adjacent to the proximal stomach for treating various diseases that can be affected by gastric stimulation, such as, gastric motility problems and diabetes. The present application further incorporates by reference U.S. Pat. No. 6,901,295, PCT/US08/56479, and U.S. patent application Ser. Nos. 12/030,222, 11/539,645, and 12/359,317 in their entirety.

The systems and methods disclosed herein can be used to achieve a plurality of different therapeutic objectives, including: treatment of achalasia; normalizing a patient's LES function; treatment of a hypertensive LES; treatment of aperistalsis of the esophagus; decreasing resting or baseline LES pressure; treating a patient to normalize esophageal pH, wherein said normalization is achieved when a patient has an esophageal pH value of less than 4 for a period of time no greater than 5%, 10%, or 15% of a 24 hour period or some fraction thereof; treating a patient to normalize esophageal pH when in the supine position, wherein said normalization is achieved when a patient has an esophageal pH value of less than 4 for a period of time no greater than 3% of a 24 hour period; treating a patient to prevent damage to the patient's lower esophageal sphincter caused by stasis; treating a patient to reduce the incidence of stasis; treating a patient to mitigate damage to the patient's lower esophageal sphincter caused by stasis; treating a patient to stop progression of damage to the patient's lower esophageal sphincter caused by stasis; modifying or decreasing esophageal body pressure; modifying or improving esophageal body function; reducing incidents of regurgitation; decreasing lower esophageal tone; treating a patient to reduce the incidence of complications secondary to achalasia, including, but not limited to, weight loss, respiratory complications, nocturnal cough, and chest pain; detecting when a patient swallows; detecting when a patient is eating; treating a gastrointestinal condition of a patient; treating a patient to minimize the patient's consumption of certain solids or liquids; reducing patient symptoms associated with achalasia wherein such reduction is measured by an improvement in a patient quality of life survey and wherein said improvement is calculated by having a patient provide a first set of responses to said quality of life survey prior to treatment and having a patient provide a second set of responses to said quality of life survey after said treatment and comparing the first set of responses to said second set of responses; treating a patient for any of the above-listed therapeutic objectives with the additional requirement of avoiding tissue habituation, tissue fatigue, tissue injury or damage, or certain adverse reactions, including, but not limited to, chest pain, pain associated with swallowing, heartburn, injury to surrounding tissue, or arrhythmias.

The disclosed treatment methods may be practiced within, and devices may be implanted within, a plurality of anatomical regions to achieve one or more of the therapeutic objectives described above. Treatment sites, or implantation sites, include: the lower esophageal sphincter; within 5 cm above and 5 cm below the LES; proximate to the LES; in the vicinity of the LES; the esophageal body; the upper esophageal sphincter (UES); within, proximate to, or in the vicinity of the gastro-esophageal junction; the esophagus, including esophageal body, LES, and UES; proximate to the esophagus; in the vicinity of the esophagus; at or within the stomach; nerves supplying the LES or gastro-esophageal junction; nerves supplying the esophageal body; nerves supplying the UES; or nerves supplying the esophagus, including the esophageal body, LES, and UES.

Additionally, it should be appreciated that a therapy which requires a lower amount of energy increases the long-term functionality of a stimulation device. Furthermore, accurate implantation of electrodes is imperative for improved efficacy and safety of these devices. Submucosa of organ systems, such as the area within the gastrointestinal tract between the muscularis mucosa and muscularis propria (two high impedance layers), have a relatively lower electrode-tissue interface impedance (referred to as impedance herein) and are therefore desirable locations for lead implantation and improved efficacy of stimulation. In addition, the loose connective tissue of the submucosa provides an improved environment for tunneling and creating pockets for lead implantation and microstimulator implantation.

In one embodiment, a method for treating achalasia in a patient comprises the following steps: incising the lower esophageal sphincter muscle of the patient to eliminate its tone; providing a device comprising at least one electrode operably connected to a pulse generator and an energy source, wherein the device is adapted to apply electrical stimulation to a target tissue; implanting the device within the upper gastrointestinal tract of the patient, wherein the electrode is positioned proximate a portion of the lower esophageal sphincter muscle; and, operating the device to apply electrical stimulation to the lower esophageal sphincter muscle to modulate its function.

In one embodiment, the macrostimulator, microstimulator or their respective electrodes are implanted in the submucosa proximate to the LES, esophagus, or UES to cause adjacent smooth muscle contraction using electrical field stimulation. Additional stimulator structures and/or electrodes may be placed in the adjacent muscularis or serosa and used in combination with the aforementioned macrostimulator or microstimulator. In another embodiment, the stimulator or electrodes are implanted in the gastrointestinal submucosa to cause gastrointestinal muscle contraction using electrical field stimulation. Additional stimulator structures and/or electrodes may be placed in or proximate the adjacent gastrointestinal muscularis mucosa, gastrointestinal serosa, or gastrointestinal nerves.

In one embodiment, the present specification is also directed toward a method of preventing a hiatal hernia in a patient with gastroesophageal reflux disease (GERD), comprising the steps of: implanting a first, proximate end of a device in the lower esophageal sphincter of the patient; and, implanting a second end, opposite the first end, of the device in the anterior abdominal wall of the patient; wherein the device prevents the formation or recurrence of a hiatal hernia over time.

The present invention is directed toward multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

Treatment Methodologies

In one embodiment, any stimulator device, including a macrostimulator or microstimulator, is programmed to implement one or more treatment protocols disclosed herein.

It should be appreciated that the treatment methods described below are implemented in a stimulator, such as a macrostimulator or microstimulator, having a plurality of electrodes, or at least one electrode, including, but not limited to, unipolar or bipolar electrodes, an energy source, such as a battery or capacitor, and a memory, whether local to the stimulator or remote from the stimulator and adapted to transmit data to the stimulator, which stores a plurality of programmatic instructions wherein said instructions, when executed by the macro/microstimulator, execute the stimulation therapies, as described below.

The present specification is directed toward stimulation treatment methods that permit a patient, with one or more implanted stimulator systems as described above, to engage in a swallow that causes liquid, food mass, food mass mixed with liquid, or any bolus of matter greater than 1 cc to pass through the patient's esophagus (collectively referred to as a wet swallow or bolus swallow; wet swallow and bolus swallow shall be used interchangeably) while concurrently having one or more gastrointestinal anatomical structures, such as the upper esophagus, upper esophageal sphincter, esophagus, lower esophageal sphincter, the distal esophagus, the gastric cardia, gastric fundus, and/or the vagus nerve, or any of the other anatomical structures described herein, be subjected to electrical stimulation.

The prior art has conventionally taught that stimulation of gastrointestinal structures, particularly the esophagus and lower esophageal sphincter, must cease when a patient engages in a swallow. It has now been unexpectedly determined that, if stimulated appropriately, such stimulation need not cease during, concurrent with, or in response to a patient engaging in a wet swallow. The stimulation protocols, described below, are effectuated through the stimulation devices described herein and by the patent documents incorporated herein by reference. Such devices generally include any device for electrical stimulation of one or more structures in the esophagus, comprising a pulse generator providing electrical stimulation, a power source for powering the pulse generator, one or more stimulating electrodes operatively coupled or connected to the pulse generator wherein the electrode sets are adapted to be positioned within or adjacent to one or more anatomical structures described herein. Preferably, the stimulating electrodes are designed to be implanted predominantly in the submucosal layer or the muscularis layer of the esophagus. In one embodiment, a plurality of electrodes in electrical communication with a macrostimulator is implanted predominantly in the muscularis propria. In one embodiment, a plurality of electrodes in electrical communication with a microstimulator is implanted predominantly in the submucosal layer, if done endoscopically, and in the muscularis layer if done laparoscopically.

In one embodiment, the stimulation parameters, which are effectuated through an electrical pulse that can be of any shape, including square, rectangular, sinusoidal or sawtooth, may comprise any of the variable ranges detailed in the table below

TABLE 1

| Pulse Type | Pulse Width | Pulse Frequency | Pulse Amplitude | On Cycle | Off Cycle |
|---|---|---|---|---|---|
| Short Pulse | 1-999 μsec | 1-100 Hz | Low (1-999 μAmp) Intermediate (1-50 mAmp) and any values therein | 0-24 hrs | 0-24 hrs |

TABLE 1-continued

| Pulse Type | Pulse Width | Pulse Frequency | Pulse Amplitude | On Cycle | Off Cycle |
|---|---|---|---|---|---|
| Intermediate Pulse | 1-250 msec | 1-100 Hz | Low (1-999 µAmp) Intermediate (1-50 mAmp) and any values therein | 0-24 hrs | 0-24 hrs |
| Intermediate Pulse | 1-250 msec | 1-59 cpm | Low (1-999 µAmp) Intermediate (1-50 mAmp) and any values therein | 0-24 hrs | 0-24 hrs |
| Long Pulse | 251 msec-1 sec | 1-59 cpm | Low (1-999 µAmp) Intermediate (1-50 mAmp) and any values therein | 0-24 hrs | 0-24 hrs |

In one embodiment, the present specification is directed toward a method for treating esophageal disease by electrically stimulating a lower esophageal sphincter or nerve supplying the LES that causes a decrease in the lower esophageal sphincter pressure without affecting, preventing, prohibiting, or otherwise hindering a bolus swallow induced relaxation of the lower esophageal sphincter or bolus swallow induced esophageal body motility. In one embodiment, the present specification is directed toward a method for treating esophageal disease by electrically stimulating the esophageal smooth muscle or a nerve supplying the esophageal smooth muscle that causes an increase in esophageal peristaltic activity without affecting, preventing, prohibiting, or otherwise hindering a bolus swallow induced relaxation of the lower esophageal sphincter or bolus swallow induced esophageal body motility. In these embodiments, because electrical stimulation need not be inhibited, there is no need to sense for the bolus swallow in order to trigger a cessation of electrical stimulation and, therefore, a stimulator need not be programmed to sense for the bolus swallow, to modify stimulation in response to a bolus swallow (even if the stimulation device has sensing capabilities), or to be otherwise responsive to a bolus swallow.

This stimulation process normalizes lower esophageal sphincter function because it decreases lower esophageal sphincter pressure while not prohibiting or preventing a natural bolus swallow. This process also a) does not affect gastric distension induced relaxation of the lower esophageal sphincter, b) improves the post bolus swallow reduction of the LES pressure, and c) improves the esophageal body function, among other therapeutic benefits, as described above.

Having eliminated the need to dynamically control the electrical stimulation based on swallow sensing, the system can be allowed to engage in automated "on/off" duty cycles that can range from 1 second to 24 hours. During the "on" period, stimulation is preferably applied for a long enough period to enable recruitment of adequate nerves and/or muscle fibers to achieve the desired pressure, function or effect. The desired "on" period is patient specific and is preferably calculated based on the time required to change the LES pressure from baseline pressure or function to the desired therapeutic pressure or function plus additional time to maintain the therapeutic pressure (maintenance time) or function. In one embodiment, the maintenance time ranges from 1 second to 12 hours. While sensors are not required, in one embodiment, the "on" period can be determined, or triggered by, sensors that sense changes in the LES, such as LES pressure changes, or changes in the esophagus. Those sensing electrodes sense one or more of changes in gastrointestinal muscle tone or impedance, peristaltic activity, esophageal peristalsis, esophageal pH, esophageal pressure, esophageal impedance, esophageal electrical activity, gastric peristalsis, gastric electrical activity, gastric chemical activity, gastric hormonal activity, gastric temperature, gastric impedance, electrical activity, gastric pH, blood chemical and hormonal activity, vagal or other gastrointestinal neural activity and salivary chemical activity and can be preferably positioned in or adjacent one or more of the esophagus, the stomach, the small intestine, the colon, the vagus or other gastrointestinal nerves and the vascular system.

The "off" period is preferably set in order to prevent development of tolerance or muscle fatigue, to improve device functionality, and to optimize energy consumption from the battery. The desired "off" period ranges from 1 second to 24 hours. The desired "off" period is patient specific and calculated based on the time required to change the LES pressure or function from the desired therapeutic pressure or function to the baseline pressure or function plus optional additional time to maintain the baseline pressure (relaxation time) or function. In one embodiment, the relaxation time ranges from 1 second to 12 hours. While sensors are not required, in one embodiment, the "off" period can be determined, or triggered by, sensors that sense changes in the LES, such as pressure, or changes in the esophagus. Those sensing electrodes sense one or more of changes in gastrointestinal muscle tone or impedance, peristaltic activity, esophageal peristalsis, esophageal pH, esophageal pressure, esophageal impedance, esophageal electrical activity, gastric peristalsis, gastric electrical activity, gastric chemical activity, gastric hormonal activity, gastric temperature, gastric impedance, gastric pH, blood chemical and hormonal activity, vagal or other gastrointestinal neural activity and salivary chemical activity and can be preferably positioned in or adjacent one or more of the esophagus, the stomach, the small intestine, the colon, the vagus or other gastrointestinal nerves and the vascular system.

Accordingly, in one embodiment, stimulation can be provided for a first period to generate a LES pressure, function or esophageal function of a first threshold level, then the stimulation can be lowered or removed while still maintaining LES pressure at or below the first threshold level of LES pressure while LES function and/or esophageal function remain at or above the first threshold level of LES function or esophageal function, thereby treating achalasia and other gastrointestinal indications. Stimulation of greater than a first threshold level of LES pressure can be delivered within a time period of less than a first time period, thereby treating certain gastrointestinal indications. In one embodiment, the present specification discloses a treatment method in which stimulation, such as at or under 30 mAmp, 15 mAmp, 10 mAmp, 8 mAmp, or any increment therein, is applied to achieve a LES pressure of less than a first threshold level and, concurrently, wet swallows are still enabled without terminating or decreasing the stimulation. In one embodiment, the present specification discloses a treatment method in which stimulation, such as at or under 30 mAmp, 15 mAmp, 10 mAmp, 8 mAmp, or any increment therein, is applied and then terminated, after which LES pressure decreases and esophageal function increases beyond a first threshold level and, concurrently, wet swallows are still enabled. It should be appreciated that the stimulation parameters can be presented in terms of total energy applied. For example, the current stimulation parameters can be replaced, throughout this specification, with preferred energy levels, such as at or under 6 millicoulombs (mC), 3 mC, 1 mC, 0.08 mC, or any increment therein.

It should further be appreciated that the treatment methodologies disclosed herein adjust for, take advantage of, account for, or otherwise optimally use a delayed, or latent, pressure response from the LES in response to electrical stimulation. Conventionally, the prior art has taught that the LES instantaneously responds, either by contracting or relaxing, to the application of, or removal of, electrical stimulation. In the present treatment methodologies, the LES has a delayed or latent response to electrical stimulation, thereby resulting in a gradual decrease in LES pressure after the application of electrical stimulation and a sustained reduced level of LES pressure after electrical stimulation is terminated, at least for certain stimulation parameters. Accordingly, a desired normalization of LES pressure or tone can be achieved well in advance of an expected achalasia triggering event, such as eating or bolus swallowing by applying electrical stimulation before the achalasia triggering event and then terminating the stimulation prior to, during, or after the achalasia triggering event. Multiple embodiments of the present invention take advantage of this delayed response by stimulating the LES in a manner that does not cause immediate relaxation of the musculature or an immediate decrease in LES pressure. In one embodiment, stimulation is directed to the LES at a level of no more than 6 mC repeated on a regular basis, for example 20 times a second, for a specific period of time, for example 30 minutes. This results in relaxation of the LES and a decrease in LES pressure that does not occur until after the initial stimulation has been initiated and that continues or persists once stimulation has been terminated. In one embodiment, using stimulation parameters similar to those above, the relaxation of the LES and decrease in LES pressure does not occur until after the initial 5 minutes of stimulation and continues once stimulation has been terminated.

In these stimulation methodologies, a sub-threshold stimulation that does not generate an instantaneous LES or esophageal function response is applied for a predefined duration of time to achieve a therapeutic response. In one embodiment, sub-threshold stimulation means that an applied stimulation does not substantially instantaneously achieve relaxation of the LES. Sub-threshold stimulation may have stimulation parameters of less than 20 mAmp, less than 10 mAmp, or less than 8 mAmp. In one embodiment, a threshold or above threshold stimulation means that an applied stimulation substantially instantaneously achieves relaxation of the LES and may have stimulation parameters of greater than 20 mAmp, greater than 10 mAmp, or greater than 8 mAmp. Sub-threshold stimulation has multiple advantages, including improved device functionality, improved energy transfer in a wireless microstimulator, improved patient safety, decreased patient adverse symptoms or side effects and decreased tolerance and/or fatigue.

Referring to FIG. 1, a normal esophageal pressure profile 100 is shown. With deglutition, the peristaltic wave follows immediately after the UES relaxation, producing a lumen-occluding contraction of the esophageal circular muscle. The contraction wave migrates aborally at a speed that varies along the esophagus. The peristaltic velocity averages about 3 cm/sec in the upper esophagus, then accelerates to about 5 cm/sec in the mid-esophagus, and slows again to approximately 2.5 cm/sec distally. The duration and amplitude of individual pressure waves also varies along the esophagus. The duration of the wave is shortest in the proximal esophagus (approximately 2 seconds) and longest distally (approximately 5 to 7 seconds). Peak pressures average 53±9 mmHg in the upper esophagus, 35±6 mmHg in the mid-portion, and 70±12 mmHg in the lower esophagus. These parameters can be influenced by a number of variables including bolus size, viscosity, patient position (e.g., upright vs. supine), and bolus temperature. For instance, a large bolus elicits stronger peristaltic contractions that migrate distally at a slower rate than a small bolus. The peristaltic velocity is also slowed by outflow obstruction or increases in intra-abdominal pressure. Warm boluses tend to enhance, whereas cold boluses inhibit, the amplitude of peristaltic contractions.

Accordingly, bolus 102 propagates through the UES 112, esophageal body 115, and LES 117 over a period of approximately, and typically, ten seconds. As the bolus 102 passes through the esophagus, portions of the UES 112, esophageal body 115, and LES 117 experience an increase in pressure. In a normal person, the baseline pressure range for the UES 112 is between 34 and 104 mmHg, for the esophagus 115 is between 30 and 180 mmHg, and for the LES 117 is between 10 and 45 mmHg. At the point of LES relaxation 110, which occurs to permit the bolus to pass through into the stomach, the LES pressure decreases to below approximately 8.4 mmHg. Notably, in a normal patient, post-swallow, the LES pressure increases, after having decreased for the swallow, and then remains at a higher baseline pressure level than just immediately prior to the swallow.

In one embodiment, the presently disclosed methods and systems return an abnormally functioning LES to a state of normalcy, post-stimulation or post initiation of stimulation. The treatment methodology comprises implanting a stimulation device, as described herein, and electrically stimulating the device to cause a decrease in LES pressure, in accordance with any of the stimulation methodologies described herein. After stimulation is terminated, one or more of the following functional parameters, characteristic of an abnormally functioning LES, achieves normal physiological range: a) LES basal pressure (respiratory minima) returns to a range of 15-32 mmHg, b) LES basal pressure (respiratory mean) returns to a range of 10-43 mmHg, c) LES residual pressure returns to a range of less than 15 mmHg, d) LES percent relaxation returns to a range of greater than 40%, e) LES duration of contraction returns to a range of 2.9 seconds to 5.1 seconds (3 cm above the LES), 3 seconds to 5 seconds (8 cm above the LES), or 2.8 seconds to 4.2 seconds (13 cm above the LES), and/or f) normal bolus swallows return with complete bolus transit, defined as detection of bolus exit in all 3 of the distal impedance channels.

Accordingly, the presently disclosed methods and systems modify one or more of the aforementioned functional parameters characteristic of an abnormally functioning LES or the esophagus to that of a normally or improved functioning LES or the esophagus, even after stimulation is terminated. By transforming an abnormally functioning LES or the esophagus to a normally or improved functioning LES or the esophagus, achalasia, esophageal motility disorders or esophageal neural, muscular or neuromuscular disorders, can be effectively treated.

In another embodiment, the presently disclosed methods and systems modify an abnormally functioning LES or the esophagus to provide for an adequately functioning LES or the esophagus post-stimulation. The treatment methodology comprises implanting a stimulation device, as described herein, and electrically stimulating the tissue to cause a decrease in LES pressure, in accordance with any of the stimulation methodologies described herein. After stimulation is terminated, one or more of the following functional parameters, characteristic of an abnormally functioning LES, returns to a physiological range sufficient to treat achalasia, esophageal motility disorders or esophageal neural, muscular or neuromuscular disorders: a) LES basal pressure, b) LES residual pressure, c) LES percent relaxation, d) LES duration of contraction, and e) esophageal body function. Accordingly, the present invention modifies physiological parameters characteristic of an abnormally functioning LES, relative to the patient's pre-treatment state, to that of an adequately functioning LES, even after stimulation is terminated. By transforming an abnormally functioning LES to an adequately functioning LES, achalasia, esophageal motility disorders or esophageal neural, muscular or neuromuscular disorders can be effectively mitigated.

In another embodiment, the present invention improves the LES pressure profile of an abnormally functioning LES post-stimulation. The treatment methodology comprises implanting a stimulation device, as described herein, and electrically stimulating the tissue to cause an increase in LES pressure, in accordance with any of the stimulation methodologies described herein. After stimulation is terminated, LES basal pressure is reduced, relative to the patient's pre-treatment state, by at least 5%, preferably 10%. Accordingly, the presently disclosed methods and systems modify the pressure profile of an abnormal functioning LES, even after stimulation is terminated. By doing so, achalasia, esophageal motility disorders or esophageal neural, muscular or neuromuscular disorders can be effectively mitigated.

In another embodiment, the presently disclosed methods and systems improve, post-stimulation, at least one of a) esophageal body pressure, b) esophageal body contractility, c) esophageal body motility, d) esophageal body bolus transit, or e) esophageal body peristalsis, resulting in improved esophageal bolus transit, decreasing solid and liquid retention time, and minimizing damage from exposure of retained solids and liquids. The treatment methodology comprises implanting a stimulation device, as described herein, and electrically stimulating the tissue to cause a decrease in LES pressure and/or and increase in esophageal peristaltic activity, in accordance with any of the stimulation methodologies described herein. After stimulation is terminated, at least one of a) esophageal body pressure, b) esophageal body contractility, c) esophageal body motility, e) esophageal body bolus transit, or f) esophageal body peristalsis improves and remains in an improved state while the stimulator is off.

In another embodiment, the presently disclosed methods and devices achieve any of the aforementioned therapeutic objectives by providing or implanting a stimulation device adapted to be implanted within the patient's lower esophageal sphincter, wherein the patient's esophagus has a function, and treating the patient by applying electrical stimulation, wherein the stimulation causes an improvement in esophageal function. Esophageal function may include any one of esophageal pressure, bolus transit, esophageal perception, esophageal accommodation or esophageal clearance of refluxate and/or retained solids and liquids.

In another embodiment, the presently disclosed methods and devices achieve any of the aforementioned therapeutic objectives by providing or implanting a stimulation device adapted to be implanted within the patient's lower esophageal sphincter, wherein the patient's esophagus has a function, and treating the patient by applying electrical stimulation, wherein the stimulation causes a non-instantaneous or delayed improvement in esophageal function. Esophageal function may include any one of esophageal pressure, bolus transit, esophageal perception, esophageal accommodation or esophageal clearance of refluxate and/or retained solids and liquids.

Figure 2:
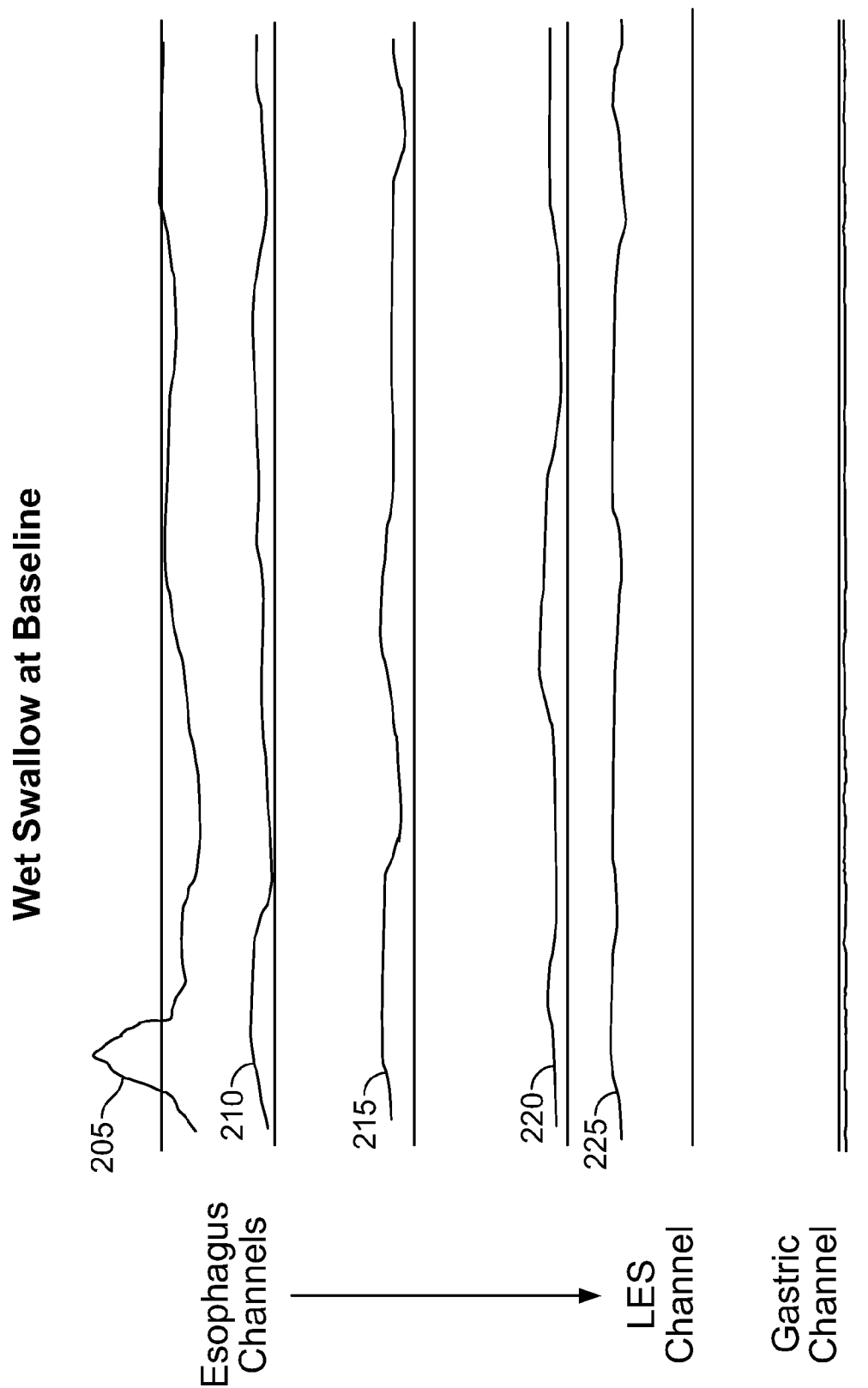
FIG. 2 is a graph depicting pressure values throughout the esophagus at baseline during a wet swallow for a patient with achalasia.

FIG. 2 is a graph depicting pressure values throughout the esophagus at baseline during a wet swallow for a patient with achalasia. After the patient swallows 205, there is little or no pressure change seen throughout the esophageal body due to a lack of peristalsis. Pressure values at the proximal 210, mid 215, and distal esophagus 220 remain relatively unchanged. In addition, the LES fails to relax, remaining at or above a baseline LES pressure 225 value of 10-45 mm Hg. The LES pressure 225 does not drop below the value of 10 mm Hg, necessary for passage of a bolus past the LES, resulting in symptoms of achalasia in the patient.

Figure 3:
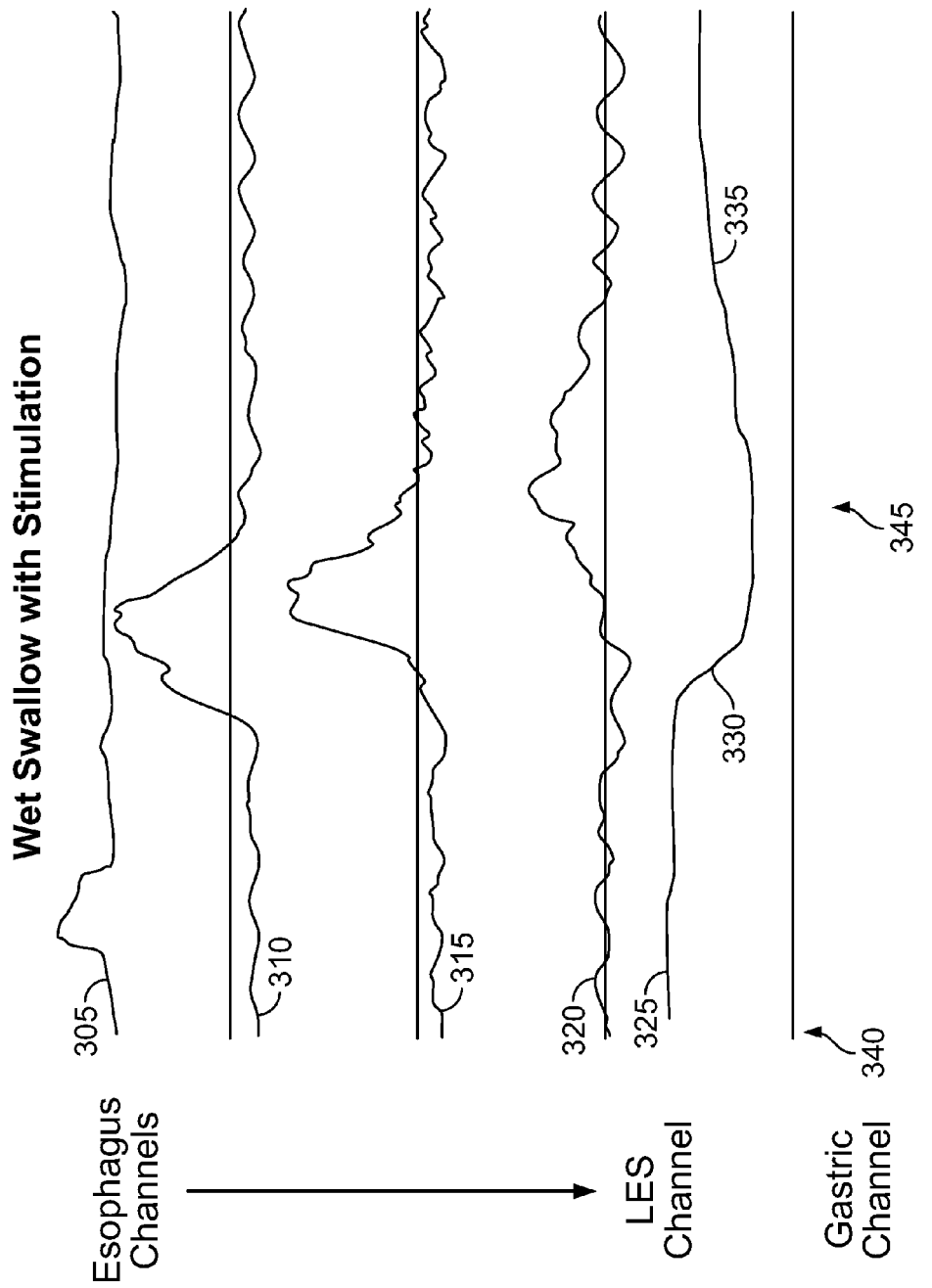
FIG. 3 is a graph depicting pressure values throughout the esophagus with stimulation during a wet swallow for a patient with achalasia.
Figure 4:
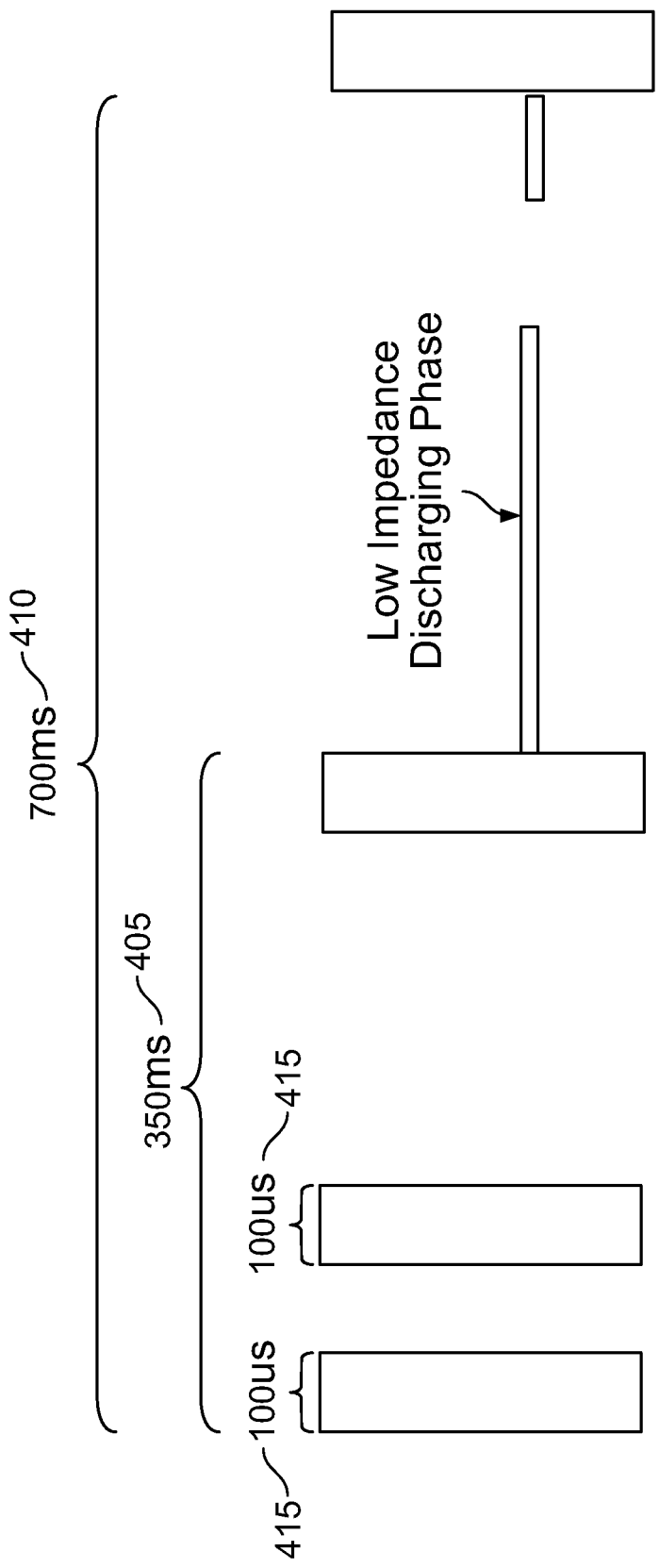
FIG. 4 is a schematic of modulated pulse trains.

FIG. 3 is a graph depicting pressure values throughout the esophagus with stimulation during a wet swallow for a patient with achalasia. In one embodiment, electrical stimulation is initiated 340 just prior to a wet swallow 305. In one embodiment, electrical stimulation is provided throughout the esophageal body and at the LES, with the objective of increasing peristaltic activity in the esophagus and decreasing pressure and lowering tone at the LES, all in an attempt to improve swallowing. In another embodiment, electrical stimulation is provided only throughout the esophageal body. In yet another embodiment, electrical stimulation is provided only at the LES. As can be seen in FIG. 3, pressure increases through the proximal 310, mid 315, and distal 320 esophagus as peristaltic activity passes the bolus down the esophagus. LES pressure begins at a high baseline value 325 and decreases 330 with electrical stimulation. In one embodiment, after stimulation is terminated 345, LES pressure remains lower 335 than baseline and slowly starts to rise again. Through the use of electrical stimulation devices and particular stimulation parameters of the present specification, the abnormally functioning esophagus encountered in patients with achalasia can be effectively treated to approximate the normal function of a healthy esophagus, as illustrated in FIG. 1.

Accordingly, in one embodiment, the present invention encompasses a method for controlling muscle action using electrical stimulation by a modulated electrical signal having carrier frequency in the range of 2 KHz-100 KHz and an on-off modulating signal having an "on" duration in the range of 5 µs to 500 msec and, in particular, 200 µs.

In one embodiment, a pacemaker lead, such as a modified Medtronic 6416 200 cm, is secured to the LES in a submucosal tunnel using endoclips along the body of the lead and exteriorized nasally. Stimulation is applied using a 200 µsec to 3 msec pulse with a pulse amplitude of 1 mAmp to 15 mAmp, more preferably 5 mAmp to 10 mAmp, pulse frequency of preferably less than 1 msec, more preferably 200 µs, and a pulse width of 200 µsec. The patient's resting LES pressure, which is greater than or equal to 25 mmHg, is thereafter decreased by at least 5%, more preferably 25-50%. Additionally, LES function is improved by at least 5%, esophageal body pressure is improved by at least 5%, esophageal body function is improved by at least 5%, quality of life is improved by at least 5%, caloric intake is improved by at least 5%, and/or weight is improved by at least 5%.

These improvements are achieved without any adverse symptoms or cardiac rhythm disturbances. These improvements are also achieved by avoiding continuous electrical stimulation, which yields problems of muscle fatigue, build up of tolerance, tissue damage, and excessively high requirements for local energy storage, such as capacitor size or battery life.

In another embodiment, the stimulator may be operated using a pulse having a frequency of 20 Hz (1-100 Hz), a pulse amplitude of 1 µAmp-1 Amp, more preferably 1-20 mAmp, and a pulse width of 1 µsec-1 msec, and more preferably 100-500 µsec. The stimulator may also be stimulated using a pulse having a frequency of 20 Hz (1-100 Hz), a pulse amplitude of 1-20 mA (1 µAmp-1 Amp), and a pulse width of 1-50 msec (500 µsec-100 msec). The stimulator may also be stimulated using a pulse having a frequency of 5 cpm (1-100 cpm), a pulse amplitude of 1-20 mAmp (1 µAmp-1 Amp), and a pulse width of 100-500 msec (1 msec-1 sec).

In certain applications, there is an advantage to combining neural stimulation with direct muscle stimulation. Such applications include, for example, gastric stimulation for gastroparesis where a combined effect on gastric muscle and neural modulation can be synergistic in improving both gastric emptying rates and symptoms associated with gastroparesis. Another example can be the treatment of chronic reflux disease where both high frequency and low frequency pulses can have desirable effects on maintaining adequate lower esophageal sphincter tone or function while modulating the perception of symptoms associated with diurnal GERD.

In certain applications where an implantable electrode or a leadless device is used for delivering electrical stimulation, it is technically more feasible to apply lower pulse width signals (having higher frequency components) than signals having wider pulse duration. The reason is that irreversible electrochemical effects occur when the total charge transfer through the electrode-tissue interface at any given time increases above a certain threshold. In these cases, electrolysis occurs which releases metal ions into the tissue, damages the electrode, and causes dangerous pH changes in the local tissue. This has negative effects on the electrode longevity and on the tissue and should be avoided especially in chronic applications where stimulation of the same site using the same electrode or device is planned for an extended period of time.

Some methods for overcoming the problems of using long pulse durations were developed that attempt to enhance the capacitance of the electrode-tissue interface so as to increase the threshold for irreversible effects, thereby increasing the maximal pulse width that can be used chronically. Electrode capacitance can be increased in various ways, such as by enhancing effective electrode surface area by coating (e.g. coating with iridium-oxide or titanium nitride), by changing the electrode material, and/or by geometrical changes in the electrode shape. These methods, however, have some undesirable consequences, such as a significant increase in the manufacturing cost of the electrode and/or making the electrode unsuitable for specific implantation procedures. It is therefore useful to minimize the use of long pulse durations.

Furthermore, it should be noted that the use of square wave pulses, which is very common in conventional electrical stimulation systems, contains energy in frequency bands that are higher than the base rate of the pulse width. In general, when a square wave is used most of the energy is delivered in the base rate and a portion of the energy is delivered in frequencies that are multiples (harmonics) of such base rate. Consequently, when a wide pulse width is delivered at a low frequency rate, some energy is also delivered in higher bands (multiples of the base rate) and also multiples of the reciprocal value of the pulse width. The practical effect, however, of these higher frequency components (or harmonics) is relatively small since only a small portion of the energy is delivered in these bands. It should further be appreciated that some frequencies, especially very high ones, are not absorbed in most tissues and can therefore be used as carriers to lower frequency signals that modulate them. Accordingly, high frequencies can be used to transfer or carry energy to the tissue without any physiological effect. Recovery of the low frequency signal is performed using a demodulator.

In light of the above, in one embodiment, a combination of low and high frequency signals (e.g. a waveform including both a high frequency component and a low frequency component) are delivered through an electrode or a leadless stimulating device with the purpose of applying two separate effects to the stimulated tissue and positively impacting increased esophageal sphincter tone. The low frequency signal will be modulated on a high frequency carrier known to be neutral to muscle tone whereas the low frequency signal will be demodulated by the tissue itself and deliver a separate impact on the tissue, which is known to occur with a direct muscle stimulation using low frequency signals. The signal is designed to have a zero net charge delivered to the tissue over durations shorter than 1 msec, thereby allowing greater flexibility in electrode design than would be capable if using a long pulse duration directly.

In one embodiment, referring to FIG. 8, the modulation is achieved by pulse trains having a base high frequency and duration equal to the desired long pulse width. Here, the stimulation train does not have a net zero charge; therefore, in order to discharge the electrode-tissue capacitance, a 350 msec time period 405 can be deployed, using a low impedance pathway switched by the stimulation device. Alternatively, a single negative discharging pulse can be applied once every 700 msec cycle 410. The low impedance connection can also preferably be applied following each of the 100 µsec pulses 415 thereby minimizing the maximal net charge accumulated on the electrode-tissue capacitance. There are several advantages of this waveform configuration: 1) the longest pulse duration applied is 100 µsec thereby relaxing the demands on a chronically implantable electrode capacitance that would have been required for a 350 msec pulse duration; 2) a train duration of 350 msec adds a low frequency component which is known to have a direct positive effect on muscle tone; 3) there is a reduced energy requirement from the device, resulting from the lower total pulse durations; and 4) the total stimulation result is optimized by a combination of two different frequency bands, each controlling the muscle through an independent physiological mechanism.

In another embodiment, the present specification encompasses an apparatus comprising a housing, pulse generator capable of generating square waves in the frequency range of 2 KHz-100 KHz, conductive tissue interface, means for fixation of conductive tissue interface to muscle tissue, programmable control unit capable of delivering said pulse generator output to the tissue intermittently whereas each "on" duration can be programmable in the range of 5 μsec to 500 msec and an "off" duration programmable in the same or different range. Optionally, the muscle tissue is the LES, esophagus, or UES. Optionally, the carrier frequency is in the range of 40 KHz-60 KHz and "on" duration is 300-400 msec. Optionally, the signal structure may be triggered by other timing mechanisms, including various patient-specific attributes, activities, and states. Optionally, a control unit, which is separate from a microstimulation device, includes a demodulator and a pulse generator for the high frequency carrier, transmits energy to the microstimulator to power the pulse generator, and includes modulation information using a different carrier frequency. Optionally, the stimulation device comprises multiple leads output and alternates a modulation signal between two or more stimulation locations where, while one location has an "on" state, the other location has an "off" state, and vice-versa.

In another embodiment, the stimulator may be stimulated using an "on" phase and an "off" phase, wherein the on phase is between 1 minute and 1 hour and the off phase is between 1 minute and 1 hour. Preferably, both the on and off phases are between 5 and 30 minutes. In another embodiment, the stimulator or microstimulator may be stimulated using a combination of a low frequency pulse and an intermediate or high frequency pulse. In one embodiment, the low frequency pulses are delivered for a duration that is 1% to 1000% of the intermediate or high pulse duration.

In another embodiment, the stimulator may be stimulated using an "on" phase and an "off" phase, wherein the on phase is between 1 second and 24 hours and the off phase is between 1 second and 24 hours. Preferably, the off phase is longer than the on phase. In this embodiment, the stimulator or microstimulator may be stimulated using a combination of a low frequency pulse and an intermediate or high frequency pulse. In one embodiment, the low frequency pulses are delivered for a duration that is 1% to 1000% of the intermediate or high pulse duration. In another embodiment, a combination of same frequency pulses with varying amplitude can be used. For example, a patient can receive intermittent or continuous stimulation at a lower amplitude with one or more sessions of stimulation at a higher amplitude, wherein the higher amplitude is at least twice the lower amplitude.

It should be appreciated that, wherever stimulation parameters are described, the stimulation may be initiated by "ramping up" to the stated stimulation levels or may be terminated by "ramping down" to an off state. The ramp up and ramp down can be as slow or as fast as required to effectuate the required therapy.

In one embodiment, the programmed duty cycle, pulse frequency, pulse width, pulse amplitude of the stimulator, and corresponding electrode configuration are configured to trigger secretion of neurokinin A (NKA) or a similar peptide. The configuration of the frequency and amplitude is set to efficiently achieve a clinically significant secretion with minimal energy. The session duration can make use of the long degradation time of NKA and be configured to turn off stimulation following the expected accumulation of sufficient NKA secretion. Electrode configuration, as further described below, can be adapted so that the desired optimal session duration will alternate in different regions using implantation of electrodes in different regions of the LES.

It should further be noted that, because the stimulation device enables the therapeutically effective treatment of a plurality of ailments, as described above, at currents below 15 mAmp, one can avoid subjecting the patient to physical pain, sensation, or discomfort. The present system can achieve the therapeutic goals and effectively operate by delivering lower stimulation levels for longer periods of time, such as by delivering 3 mAmp for 10 minutes rather than 15 mAmp for 5 minutes. The pulse frequency can be 20 Hz and the stimulation can be delivered less than five times per day, such as three times per day.

In one embodiment, the presently disclosed methods and devices achieve any of the aforementioned therapeutic objectives by providing or implanting a stimulation device, such as a macrostimulator or microstimulator, adapted to be implanted within the patient's lower esophageal sphincter and adapted to apply electrical stimulation to the patient's lower esophageal sphincter; and programming, using, or operating said stimulation device, wherein said programming, use, or operation defines, uses, or is dependent upon a plurality of stimulation parameters that determine the application of electrical stimulation to the patient's lower esophageal sphincter and wherein said stimulation parameters are selected, derived, obtained, calculated, or determined, at least in part, to account for a latent, delayed, time-delayed, or future response of the patient's lower esophageal sphincter.

In one embodiment, the presently disclosed methods and devices achieve any of the aforementioned therapeutic objectives by providing or implanting a stimulation device adapted to be implanted within the patient's lower esophageal sphincter and to apply electrical stimulation to the patient's lower esophageal sphincter, wherein said lower esophageal sphincter exhibits a latent, delayed, time-delayed, or future response to applied electrical stimulation; and treating said patient by applying electrical stimulation based upon derived from, or dependent upon said latent, delayed, time-delayed or future response.

In one embodiment, the presently disclosed methods and devices achieve any of the aforementioned therapeutic objectives by providing or implanting a stimulation device adapted to be implanted within the patient's lower esophageal sphincter and to apply electrical stimulation to the patient's lower esophageal sphincter; and initiating, activating, beginning, or starting said electrical stimulation prior to a pre-defined or fixed time wherein said pre-defined or fixed time is associated with an achalasia triggering event and wherein said initiation occurs prior to said pre-defined or fixed time by a minimum period, such as at least 5 minutes, 10 minutes, 15 minutes, 30 minutes, 1 hour, 2 hours, 3 hours, 12 hours, 24 hours, or any time increment therein.

In one embodiment, the presently disclosed methods and devices achieve any of the aforementioned therapeutic objectives by providing or implanting a stimulation device adapted to be implanted within the patient's lower esophageal sphincter and adapted to apply electrical stimulation to the patient's lower esophageal sphincter; and initiating, activating, beginning, or starting said electrical stimulation prior to a pre-defined or fixed time wherein said pre-defined or fixed time is associated with an achalasia triggering event and wherein said initiation occurs prior to said pre-defined or fixed time by a minimum period, such as at least 5 minutes, 10 minutes, 15 minutes, 30 minutes, 1 hour, 2 hours, 3 hours, 12 hours, 24 hours, or any time increment therein; and terminating said electrical stimulation after said pre-defined or fixed time has passed.

In one embodiment, the presently disclosed methods and devices achieve any of the aforementioned therapeutic objectives by providing or implanting a stimulation device adapted to be implanted within the patient's lower esophageal sphincter and adapted to apply electrical stimulation to the patient's lower esophageal sphincter; and programming, using, or operating said stimulation device, wherein said programming, use, or operation defines, uses, or is dependent upon a plurality of stimulation parameters that determine the application of electrical stimulation to the patient's lower esophageal sphincter and wherein said stimulation parameters are selected, derived, obtained, calculated, or determined, at least in part, to treat achalasia without lowering LES pressure to a point wherein the patient experiences symptoms of esophageal reflux.

In one embodiment, the presently disclosed methods and devices achieve any of the aforementioned therapeutic objectives by providing or implanting a stimulation device adapted to be implanted within the patient's lower esophageal sphincter; and treating said patient by applying electrical stimulation while the patient swallows, during periods of esophageal motility, or during esophageal peristalsis.

In one embodiment, the presently disclosed methods and devices achieve any of the aforementioned therapeutic objectives by providing or implanting a stimulation device adapted to be implanted within the patient's lower esophageal sphincter; and treating said patient by applying electrical stimulation in accordance with a preset period and wherein said preset period is not dependent upon, influenced by, modified by, lengthened by, or shortened by a physiological state of a patient.

In one embodiment, the presently disclosed methods and devices achieve any of the aforementioned therapeutic objectives by providing or implanting a stimulation device adapted to be implanted within the patient's lower esophageal sphincter; and treating said patient by applying electrical stimulation in accordance with a preset period and wherein said preset period is not dependent upon, influenced by, modified by, lengthened by, or shortened by the patient swallowing, esophageal motility, esophageal peristalsis, or being in a feeding state.

In one embodiment, the presently disclosed methods and devices achieve any of the aforementioned therapeutic objectives by providing or implanting a stimulation device adapted to be implanted within the patient's lower esophageal sphincter; and treating said patient by applying electrical stimulation that is not dependent upon, influenced by, modified by, lengthened by, or shortened by a physiological state, biological parameter, sensed physiological or biological parameters of a patient.

In one embodiment, the presently disclosed methods and devices achieve any of the aforementioned therapeutic objectives by providing or implanting a stimulation device adapted to be implanted within the patient's lower esophageal sphincter; and treating said patient by applying electrical stimulation that is not dependent upon, influenced by, modified by, lengthened by, or shortened by the patient swallowing, esophageal motility, esophageal peristalsis, or being in a feeding state.

In one embodiment, the presently disclosed methods and devices achieve any of the aforementioned therapeutic objectives by providing or implanting a stimulation device adapted to be implanted within the patient's lower esophageal sphincter, wherein said lower esophageal sphincter has a pressure; and treating said patient by applying sufficient electrical stimulation to decrease said pressure but not allow for reflux of stomach contents into the distal esophagus.

In one embodiment, the presently disclosed methods and devices achieve any of the aforementioned therapeutic objectives by providing or implanting a stimulation device adapted to be implanted within the patient's lower esophageal sphincter, wherein the lower esophageal sphincter has a function, and treating the patient by applying sufficient electrical stimulation to improve the function but not to inhibit, hinder, stop, or prevent swallowing, esophageal motility, or esophageal peristalsis or dissuade a patient from being in a feeding state.

In one embodiment, the presently disclosed methods and devices achieve any of the aforementioned therapeutic objectives by providing or implanting a stimulation device adapted to be implanted within the patient's lower esophageal sphincter, wherein said lower esophageal sphincter has a pressure; and treating said patient by applying electrical stimulation, wherein said stimulation causes an decrease in said pressure of at least 5% only after an elapsed period of time of at least one minute.

In one embodiment, the presently disclosed methods and devices achieve any of the aforementioned therapeutic objectives by providing or implanting a stimulation device adapted to be implanted within the patient's lower esophageal sphincter, wherein said lower esophageal sphincter has a pressure; and treating said patient by applying electrical stimulation, wherein said stimulation improves or normalizes lower esophageal function, improves or normalizes LES pressure, or decreases LES pressure to a normal physiological range only after an elapsed period of time or only after a delay of at least one minute.

In one embodiment, the presently disclosed methods and devices achieve any of the aforementioned therapeutic objectives by providing or implanting a stimulation device adapted to be implanted within the patient's lower esophageal sphincter, wherein said lower esophageal sphincter has a pressure; and treating said patient by applying electrical stimulation, wherein said stimulation causes a non-instantaneous or delayed decrease in said pressure.

In one embodiment, the presently disclosed methods and devices achieve any of the aforementioned therapeutic objectives by providing or implanting a stimulation device adapted to be implanted within the patient's lower esophageal sphincter, wherein the lower esophageal sphincter has a function, and treating the patient by applying electrical stimulation, wherein the stimulation causes a non-instantaneous or delayed improvement in the function.

In one embodiment, the presently disclosed methods and devices achieve any of the aforementioned therapeutic objectives by providing or implanting a stimulation device adapted to be implanted within the patient's lower esophageal sphincter, wherein said lower esophageal sphincter has a pressure; and treating said patient by applying electrical stimulation, wherein said stimulation causes a non-instantaneous or delayed decrease in said pressure and wherein said non-instantaneous or delayed decrease in the pressure normalizes LES function, normalizes LES pressure, decreases LES pressure to a normal physiological range, or decreases LES pressure by at least 3%.

In one embodiment, the presently disclosed methods and devices achieve any of the aforementioned therapeutic objectives by providing or implanting a stimulation device adapted to be implanted within the patient's lower esophageal sphincter, wherein said lower esophageal sphincter has a pressure; and treating said patient by applying electrical stimulation, wherein said stimulation causes a gradual decrease in said pressure.

In one embodiment, the presently disclosed methods and devices achieve any of the aforementioned therapeutic objectives by providing or implanting a stimulation device adapted to be implanted within the patient's lower esophageal sphincter, wherein said lower esophageal sphincter has a pressure; and treating said patient by applying electrical stimulation, wherein said stimulation causes a decrease in said pressure after said electrical stimulation is terminated.

In one embodiment, the presently disclosed methods and devices achieve any of the aforementioned therapeutic objectives by providing or implanting a stimulation device adapted to be implanted within the patient's lower esophageal sphincter, wherein said lower esophageal sphincter has a pressure; and treating said patient by applying electrical stimulation having a first level, wherein said stimulation causes a decrease in said pressure after said electrical stimulation is decreased from said first level.

In one embodiment, the presently disclosed methods and devices achieve any of the aforementioned therapeutic objectives by improving the pressure or function of the patient's lower esophageal sphincter.

In one embodiment, the presently disclosed methods and devices achieve any of the aforementioned therapeutic objectives, wherein said patient has a lower esophageal sphincter and wherein said lower esophageal sphincter has a pressure, by decreasing the pressure of the patient's lower esophageal sphincter through the application of electrical stimulation to the lower esophageal sphincter or areas proximate thereto.

In one embodiment, the presently disclosed methods and devices achieve any of the aforementioned therapeutic objectives, wherein said patient has a lower esophageal sphincter and wherein said lower esophageal sphincter has a pressure, by decreasing the pressure of the patient's lower esophageal sphincter through the application of electrical stimulation to the lower esophageal sphincter or areas proximate thereto, and wherein said pressure does not result in episodes of gastroesophageal reflux.

In one embodiment, the presently disclosed methods and devices achieve any of the aforementioned therapeutic objectives by modifying the pressure or function of the patient's lower esophageal sphincter.

In one embodiment, the presently disclosed methods and devices achieve any of the aforementioned therapeutic objectives by modifying the pressure or function of the patient's lower esophageal sphincter through the application of electrical stimulation to the lower esophageal sphincter or areas proximate thereto.

In one embodiment, the presently disclosed methods and devices achieve any of the aforementioned therapeutic objectives by modifying the pressure or function of the patient's lower esophageal sphincter through the application of electrical stimulation to the lower esophageal sphincter or areas proximate thereto and wherein said pressure does not result in episodes of gastroesophageal reflux.

In one embodiment, the presently disclosed methods and devices achieve any of the aforementioned therapeutic objectives by providing or implanting a stimulation device adapted to be implanted within the patient's lower esophageal sphincter, and treating said patient by applying electrical stimulation in accordance with at least one on period, wherein said on period is between 1 second and 24 hours and is not triggered by, substantially concurrent to, or substantially simultaneous with an incidence of achalasia, and at least one off period, wherein said off period is greater than 1 second.

In one embodiment, the presently disclosed methods and devices achieve any of the aforementioned therapeutic objectives by providing or implanting a stimulation device adapted to be implanted within the patient's lower esophageal sphincter, and treating said patient by applying electrical stimulation, wherein a pulse amplitude from a single electrode pair ranges from greater than or equal to 1 mAmp to less than or equal to 8 mAmp.

In one embodiment, the presently disclosed methods and devices achieve any of the aforementioned therapeutic objectives by providing or implanting a stimulation device adapted to be implanted within the patient's lower esophageal sphincter, and treating said patient by applying electrical stimulation having a pulse duration of approximately 200 µsec.

In one embodiment, the presently disclosed methods and devices achieve any of the aforementioned therapeutic objectives by providing or implanting a stimulation device adapted to be implanted within the patient's lower esophageal sphincter, and treating said patient by applying electrical stimulation having a pulse duration of approximately 1 msec.

In one embodiment, the presently disclosed methods and devices achieve any of the aforementioned therapeutic objectives by providing or implanting a stimulation device adapted to be implanted within the patient's lower esophageal sphincter, and treating said patient by applying electrical stimulation having a pulse energy level of <10 mAmp, pulse duration of <1 second, and/or pulse frequency of <50 Hz.

In one embodiment, the presently disclosed methods and devices achieve any of the aforementioned therapeutic objectives by providing or implanting a stimulation device adapted to be implanted within the patient's lower esophageal sphincter, and treating said patient by applying electrical stimulation having a pulse energy level of 1 mAmp to 10 mAmp (preferably 1 mAmp), pulse duration in a range of 50 µsec to 1 msec (preferably 215 µsec), a pulse frequency of 5 Hz to 50 Hz (preferably 20 Hz), pulse on time in a range of 10 minutes to 120 minutes (preferably 30 minutes), and/or pulse off time in a range of 10 minutes to 24 hours.

In one embodiment, the presently disclosed methods and devices achieve any of the aforementioned therapeutic objectives by providing or implanting a stimulation device adapted to be implanted within the patient's lower esophageal sphincter, and treating said patient by applying electrical stimulation to decrease LES pressure below a baseline or threshold LES pressure, wherein said LES pressure remains below said baseline or threshold LES pressure after termination of electrical stimulation.

In one embodiment, the presently disclosed methods and devices achieve any of the aforementioned therapeutic objectives by providing or implanting a stimulation device adapted to be implanted within the patient's lower esophageal sphincter, and treating said patient by applying electrical stimulation to decrease LES tone below a threshold LES tone, wherein said LES tone remains below said threshold LES tone after termination of electrical stimulation.

In one embodiment, the presently disclosed methods and devices provide a macrostimulator programmed, adapted to, or configured to perform any of the aforementioned methods or treatment protocols.

In one embodiment, the presently disclosed methods and devices provide a macrostimulator comprising at least one electrode, an energy source, and a pulse generator in electrical communication with the at least one electrode and energy source, wherein said pulse generator is programmed, adapted, or configured to perform any of the aforementioned methods or treatment protocols.

In one embodiment, the presently disclosed methods and devices provide a microstimulator programmed, adapted, or configured to perform any of the aforementioned methods or treatment protocols.

In one embodiment, the presently disclosed methods and devices provide a microstimulator comprising at least one electrode, an energy source, and a pulse generator in electrical communication with the at least one electrode and energy source, wherein said pulse generator is programmed, adapted, or configured to perform any of the aforementioned methods or treatment protocols.

Such treatment methods may be combined, directed toward any of the aforementioned therapeutic objectives, and/or implemented through stimulating any of the aforementioned anatomical areas. The treatment methods may be further modified by using specific stimulation parameters, open loop data processes, closed loop data processes, the patient's physical position and degree of activity, the patient's eating state, timing, quantity or content thereof, certain physiological parameters sensed by the device, including LES pressure, or anti-habituation methods to prevent anatomical habituation to a specific set of stimulation parameters. Additionally, because the device can operate on a time based schedule and not on a physiological trigger based schedule (although a physiological trigger based schedule can be an optional embodiment), stimulation schedules can be tailored to user behavior and/or routine. For example, stimulation therapy can be delivered or stimulation energy can be transmitted at times that are most convenient, least disruptive to the patient's activities of daily living, such as only scheduling stimulation while the patient is sleeping, relaxing, or watching TV and scheduling stimulation only before or after mealtimes. Such additional embodiments are described below.

Open Loop Programming

In one optional embodiment, the stimulation parameters, including pulse width, pulse frequency, pulse amplitude, ramp rates, and/or duty cycle, can be modified by a physician using data sensed by, stored within, or transmitted from the stimulation device, data sensed by, stored within, or transmitted from a sensor implanted in the patient, and/or data captured by an external computing device used by a patient. A stimulator device having a local memory, or a transmitter capable of communicating sensed information to a remotely located memory, captures a plurality of sensed data, as discussed in greater detail below. Concurrently, a patient controlled computing device, such as a laptop, personal computer, mobile device, or tablet computer, which is external to the patient, is used by the patient to store data input by the patient relevant to evaluating, monitoring, and adjusting the operation of the stimulator. Both the stimulator captured data and patient inputted data is then transmitted to a physician controlled device, as described below, to enable the physician to properly evaluate, monitor, and modify the stimulation parameters.

In one embodiment, the patient-controlled computing device comprises a plurality of programmatic instructions that, when executed, generate a display which prompts a user to input information regarding the user's diet, physical activity, and symptoms, such as: the timing of food intake; exercise regimen; degree and extent of physical symptoms; incidents of achalasia; when the user sleeps; when the user lays down; type of food being consumed; and quantity of food among other variables, and, is capable of receiving said input from the user. This data is captured and stored locally and/or transmitted to a remote server for access by a physician. If accessed remotely by a physician, the physician can transmit alerts back to the patient, via a network in communication with the computing device or via conventional communication systems, such as email, text messaging or phone, to confirm dose amounts, patient state information, or provide for therapy adjustment.

In one embodiment, the stimulator captured data includes what stimulation parameters were used and when, the sensed LES pressure profile, including the percentage or amount of time the LES pressure was above a certain threshold level, such as 25 mmHg, or above a $2^{nd}$ threshold level, such as 15 mm Hg, esophageal pH, supine events, and degree of physical movement, among other variables.

The patient-inputted data, when combined with the stimulator captured data, can provide a holistic view of the patient's condition and the efficacy of a stimulation regimen. In particular, as patient symptoms are mapped to stimulation parameters and analyzed in relation to food or drink intake, sleep, and exercise regimens, a physician will be able to determine how best to modify the stimulation parameters, including duty cycle, stimulation initiation times or triggers, stimulation termination times or triggers, pulse width, pulse amplitude, duty cycle, ramp rates, or pulse frequency, to improve patient treatment. As further discussed below, the physician will receive both the patient-captured and stimulation device captured data into a diagnostic terminal that can be used to process the information and transmit new stimulation parameters, if necessary, to the stimulation device. For example, the physician can modify the stimulation parameters in a manner that would lower the incidents of reported achalasia, generalized pain, pain while swallowing, generalized discomfort, discomfort while swallowing, or lack of comfort during sleeping or physical exercise. The physician can also modify the stimulation parameters, including the initiation and termination of stimulation, to better match one or more achalasia triggering events, such as eating, sleeping, lying down, or engaging in physical activity. The physician can also modify the stimulation parameters, including the initiation and termination of stimulation, to better match the patient's personal work or vacation schedule.

Additionally, alerts can be created that can be either programmed into the patient-controlled device or stimulation device which serve to notify the patient of a device malfunction, a recommendation to take a drug, and a recommendation to come back for a checkup, among other variables. Those alerts can also be transmitted, via a computing network, to the physician. Furthermore, external data sources, such as demographic data or expert protocols, can be integrated into the physician system to help the physician improve the diagnostic and evaluation process and optimize the programmed set of stimulation parameters.

It should further be appreciated that, as the patient controlled device and stimulator device accumulate data that maps the therapeutic regimen against the patient's activities and symptoms, the patient controlled device will be able to determine, and therefore inform the patient of, patterns which tend to increase or decrease the incidents of achalasia, including types of food, quantity of food, and timing of eating, among other variables.

Closed Loop Programming

In one optional embodiment, the stimulation parameters, including pulse width, pulse frequency, pulse amplitude, initiation of stimulation, triggers for stimulation, termination of stimulation, triggers to terminate stimulation, ramp rates, and/or duty cycle, can be dynamically and intelligently modified by the stimulation device using data sensed by, stored within, or transmitted from the stimulation device, data sensed by, stored within, or transmitted from a sensor implanted in the patient, and/or data captured by, stored within, and/or transmitted from an external computing device used by the patient.

As discussed above, data can be captured by a patient-controlled device and/or the stimulator device. In this embodiment, a stimulator is further programmed to intelligently modify stimulation parameters, without physician input, based upon sensed data and/or patient inputs. In one embodiment, a stimulator determines that LES pressure or function fails to improve above a predefined threshold, even after a predefined amount of stimulation, and, accordingly, automatically modifies the stimulation parameters, within a preset range of operation, to yield an improvement in LES pressure decrease. In one embodiment, a stimulator determines that LES function improves significantly or LES pressure drops below a predefined threshold, after a predefined amount of stimulation, or maintains a level below a predefined threshold and, accordingly, automatically modifies the stimulation parameters, within a preset range of operation, to yield an improvement in LES pressure levels or function.

In one embodiment, a stimulator determines the LES pressure levels remain below a predefined threshold level for a sufficient amount of time such that a subsequent pre-programmed stimulation session or sessions can be postponed or cancelled. In one embodiment, a stimulator device monitors LES pressure and initiates stimulation only when LES pressure rises above a predetermined threshold. Pre-programmed stimulation may be modified in order to continue or increase in energy, duration, or frequency until LES pressure drops below a predetermined threshold. The LES pressure threshold may be dynamically modified based upon sensed data.

In one embodiment, a stimulator receives a communication from an external patient controlled device indicating that the patient is reporting a number of adverse incidents above a predefined threshold, such as achalasia, generalized pain, pain while swallowing, generalized discomfort, discomfort while swallowing, lack of comfort when sleeping, etc. and, accordingly, automatically modifies the stimulation parameters, within a preset range of operation, to yield a lower level of such incidents. In one embodiment, a stimulator receives a communication from an external patient controlled device detailing a schedule of potential achalasia triggering events, including sleep times, eating times, or exercise times, and, accordingly, automatically modifies the stimulation parameters, within a preset range of operation, to properly account for such events.

In one embodiment, the stimulator operates using both open loop and closed loop programming. Stimulation parameters may be established using open loop programming methods, as described above, and then modified through the aforementioned closed loop programming methods. Stimulation parameters may also be established using closed loop programming methods, as described above, and then modified through the aforementioned open loop programming methods.

Stimulation Modification Based on Sensed Data

It should be appreciated that the stimulation device may stimulate based on a plurality of data, including based on LES pressure registering above a predefined threshold, based on a patient's pH level, based on the patient's physical orientation, based on the patient's meal intake, or based on a predefined time period, among other triggers. It should also be appreciated that the controller may initiate or stop a stimulation based on a plurality of triggers, including based on the LES pressure exceeding a predefined threshold, based on a patient's pH level, based on the patient's physical orientation, or based on a predefined time period, among other triggers.

Using various data sensors, including, but not limited to impedance, electrical activity, piezoelectric, pH, accelerometer, inclinometer, ultrasound-based sensors, RF-based sensors, or strain gauge, the stimulator device can determine whether a patient is eating, how much the patient is eating, how long the patient is eating, and/or what the patient is eating, and, based on that information, adjust stimulation parameters accordingly. In particular, pH data may be used to determine what kind of food a patient is eating, wherein the type of food is defined in terms of its acidity.

In one embodiment, the stimulator device senses LES pressure and initiates stimulation of the LES when the pressure is above a pre-defined threshold level for a pre-defined period of time and terminates stimulation of the LES when the pressure is below a pre-defined threshold level for a predefined period of time. LES pressure may be determined by sensing and processing impedance measurements, electrical activity measurements, strain gauge, and/or piezo-electric measurements. One or more of the various measurements are constantly measured to create a contiguous LES pressure profile. Based upon the LES pressure profile, the stimulator can modify stimulation parameters, including pulse amplitude, pulse width, duty cycle, pulse frequency, stimulation initiation time, ramp rate, or stimulation termination time, to achieve, with respect to the LES pressure, an absolute amount of change, a percentage amount of change, increases or decreases above or below a threshold value, increases or decreases based on time, or increases or decreases based on a LES pressure slope, among other measures of change.

In another embodiment, the stimulator device uses various data sensors to determine the pulmonary, intra-thoracic, or intra-abdominal pressure and, based on pulmonary, intra-thoracic, or intra-abdominal pressure, create a patient-specific dose, such as a specific pulse amplitude, pulse width, duty cycle, pulse frequency, stimulation initiation time, ramp rate, or stimulation termination time, required to affect LES tone, pressure, or function to the levels needed by that patient.

In another embodiment, the stimulator device uses various data sensors to determine the esophageal temperature and, based on that temperature reading, create a patient-specific dose, such as a specific pulse amplitude, pulse width, duty cycle, pulse frequency, stimulation initiation time, ramp rate, or stimulation termination time.

In another embodiment, the stimulator device uses various data sensors to determine the esophageal pH and, based on that pH reading, create a patient-specific dose, such as a specific pulse amplitude, pulse width, duty cycle, pulse frequency, stimulation initiation time, ramp rate, or stimulation termination time.

In another embodiment, the stimulator device uses a combination of data inputs from the above described sensors to generate a total score from which a stimulation therapeutic regimen is derived. For example, if the patient has not eaten for a long time and lays down, a lower (or no) therapy dose would be delivered. Detecting various patient parameters by various means and using them in an algorithm enables clinicians to target specific achalasia events. In addition, in various embodiments, multiple algorithms are programmed into the stimulator device so that treatment can be tailored to various symptoms experienced by patients with achalasia, based upon input relayed by the sensors. In one embodiment, data from any combination of one or more of the following parameters is used by an algorithm to determine stimulation protocol: patient feed state including type of intake (via patient input or eating detection by a physical sensor that can detect and/or evaluate liquids/solids/caloric value); patient position (via inclinometer/accelerometer); patient activity (via accelerometer/actimeter); patient reflux profile (via patient input/pH recording); LES pressure; LES electrical activity; LES mechanical activity (via accelerometer in the LES, pressure sensor, impedance measure or change thereof); gastric pressure; gastric electrical activity; gastric chemical activity; gastric temperature; gastric mechanical activity (via an accelerometer in the stomach, pressure sensor, impedance measurement and changes); patient intuition; vagal neural activity; and, splanchnic neural activity. Based on input from one or more of the above parameters, the algorithm quantifies the vulnerability for achalasia and modifies accordingly the amplitude, frequency, pulse-width, duty cycle, ramp rate, and timing of stimulation treatment. The table below lists the parameters, measurements, and values used in an exemplary treatment protocol of one embodiment of the present invention.

TABLE 2

| Parameter | Measurement | Value |
| --- | --- | --- |
| LES Pressure | Normal | 0 |
| | High | 1 |
| Inclination | Upright | 0 |
| | Supine | 1 |
| Feed State | Pre-prandial | 1 |
| | Post-prandial/Fasting | 0 |
| Time of the day | Day time | 1 |
| | Night time | 0 |
| Fat content of meal | Low | 0 |
| | High | 1 |
| Patient pH Profile | Low-risk period | 0 |
| | High-risk period | 1 |
| Patient Symptom Input | Low-risk period | 0 |
| | High-risk period | 1 |
| Gastric Activity | Food Absent | 0 |
| | Food Present | 1 |
| Upright Activity Level | Low | 0 |
| | High | 1 |
| Supine Activity Level | High | 1 |
| | Low | 0 |
| Patient Intuition | Low Likelihood | 0 |
| | High Likelihood | 1 |

In the table above, each individual parameter is given a score of 1 or 0 depending on the value measured. In one embodiment, a summary score is tabulated using one or more parameters in the above exemplary algorithm scoring system to determine patient vulnerability to a reflux event. Based on the score, the treatment parameter is modified. Patients with a higher summary score are indicated for a greater level of treatment. Patients with high LES pressure are assigned a 1 while those with normal LES pressure are assigned a 0. Patients in a pre-prandial feeding state are assigned a 1 and those in a fasting or post-prandial feeding state are assigned a 0. Daytime hours provide a 1 score and nighttime hours provide a 0 score. Patients are capable of inputting scores as well, with high risk symptom periods and high likelihood intuition both receiving 1 scores and low risk symptom periods and low likelihood intuition both receiving 0 scores.

In one embodiment, a measured parameter is used as a modifier for another parameter. For example, gastric activity showing food absent does not have an individual score but modifies the feed state score from a post-prandial score to a fasting/pre-prandial score. In another embodiment, a measured parameter has an absolute value that is not impacted by other measured parameters. For example, patient intuition of a high likelihood of achalasia is an absolute parameter that delivers the highest level of achalasia therapy irrespective of other sensed parameters.

In one embodiment, the scoring system for certain individual parameters is a scale rather than a binary score. For example, in one embodiment, the score given to LES pressure is within a range from 0-5 based on duration of increased pressure. With each incremental 5 minute duration of increased LES pressure, the score increases by one increment.

In another embodiment, different weight is given to different parameters. For example, in one embodiment, high LES pressure is given an absolute score higher than pre-prandial feed state.

In another embodiment, the scoring system is tailored to be patient specific. In one embodiment, for example, for a patient with low symptom predictability as ascertained by symptom association with LES pressure measurements, patient symptom input is given a lower weight.

Modifications to Prevent Habituation or Fatigue

Stimulation parameters may also be periodically modified, in accordance with a predefined schedule or dynamically by real-time physician or patient control, to reduce, avoid, or prevent the occurrence of muscle fatigue, habituation, and/or tolerance. Manipulation of the length of the "on" and "off" cycles can be performed while still obtaining the desired level of LES function. In one embodiment, the length of stimulation time to achieve the therapeutic goal can be decreased while the stimulation off time required for LES function to return to baseline can be increased. Less time spent in the "on" cycle will result in fewer incidents of muscle fatigue.

In another embodiment, the "on" and "off" cycles, as described previously, can cycle rapidly. For example, during a 30 minute period, the stimulation may be repeatedly on for 3 seconds and then off for 2 seconds during the entire 30 minute period.

In another embodiment, the patient can take a "stimulation holiday". In other words, stimulation can be further stopped for a time period greater than the "off" cycle to allow the muscle to recover. Greatly increasing the time period in which there is no stimulation also serves to avoid muscle fatigue and tolerance.

In another embodiment, stimulation parameters can be intermixed in an attempt to avoid muscle fatigue, habituation, and/or tolerance while still obtaining the desired level of LES function. For example, alternating short pulses can be intermixed with intermediate pulses to stimulate the LES. The variation in stimuli received by the muscle will assist in avoiding fatigue and tolerance.

In another embodiment, LES function can be normalized using the present specification without decreasing LES pressure below the mid-normal range. This is achieved by minimizing the energy delivered to the muscle to, but not beyond, the point where the LES regains normal function. Less energy delivered results in less fatigue and tolerance.

In another embodiment, the stimulation parameters can be changed, such as by modifying pulse width, frequency, amplitude, ramp rate, or the duty cycle, on a predefined periodic basis to avoid having the muscles habituate to a known and repeated stimulation setting. In such an embodiment, a stimulator may locally store a plurality of different stimulation parameters which are implemented in accordance with a predefined schedule. The stimulator may also store a single set of stimulation parameters, each parameter having an acceptable range of operation, and then randomly implement a stimulation parameter bounded by the acceptable ranges of operation.

Figure 5:
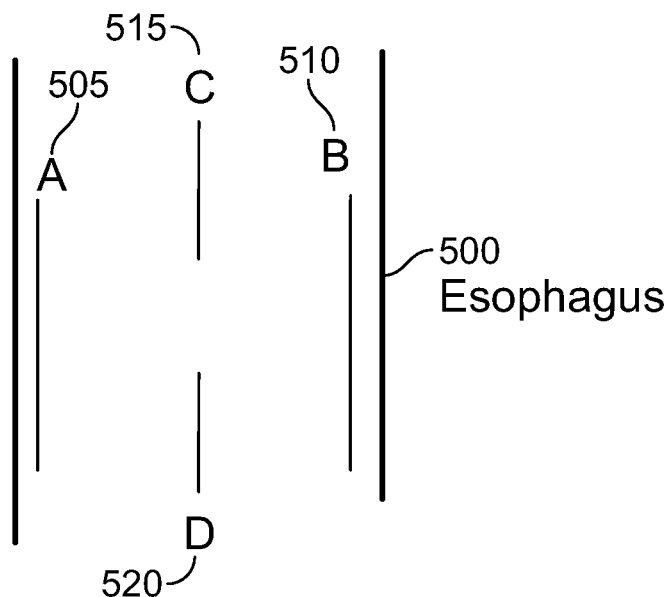
FIG. 5 depicts one exemplary electrode configuration in the esophagus of a patient.

Electrode Configurations and Methods of Placing and Confirming the Placement of Electrodes In one embodiment, the therapeutic objectives described herein are achieved by at least one of a plurality of different electrode configurations, as shown in FIG. 5. It should be appreciated that, in one embodiment, the electrode placement, as shown, at least partly enables the patient's LES function to normalize, post-stimulation, and/or the patient's LES pressure to decrease post-stimulation. The electrode configurations described herein may be used in accordance with any of the stimulation parameters, system architectures, and sensing systems described herein.

Within the esophagus 500, and more particularly the LES, a plurality of different electrode combinations can be used to achieve the therapeutic and operational objectives described herein. In one embodiment, a first electrode 505 is placed proximate the left lateral wall of the esophagus 500 and operated in combination with a second electrode placed proximate the right lateral wall 510 of the esophagus 500. In one embodiment, a first electrode 505 is placed proximate the left lateral wall of the esophagus 500 and operated in combination with a second electrode placed in the anterior proximal wall 515 of the esophagus 500. In one embodiment, a first electrode 510 is placed proximate the right lateral wall of the esophagus 500 and operated in combination with a second electrode placed in the anterior proximal wall 515 of the esophagus 500. In another embodiment, a first electrode 505 is placed proximate the left lateral wall of the esophagus 500 and operated in combination with a second electrode placed in the anterior, distal wall 520 of the esophagus 500. In one embodiment, a first electrode 510 is placed proximate the right lateral wall of the esophagus 500 and operated in combination with a second electrode placed in the anterior, distal wall 520 of the esophagus 500. In another embodiment, a first electrode 515 and a second electrode 520 are placed proximally and distally in the anterior wall of the esophagus 500. In another embodiment, more than one of the above described combinations are used serially along the length of the esophagus 500.

Figure 6:
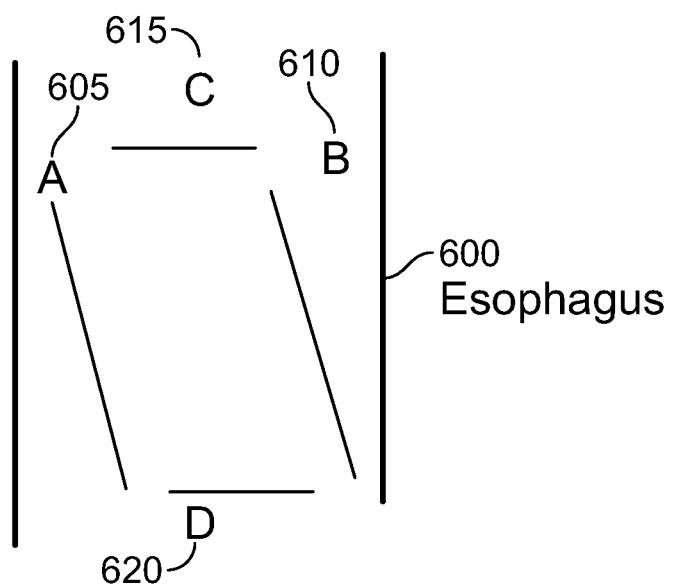
FIG. 6 depicts another exemplary electrode configuration in the esophagus of a patient.

Referring to FIG. 6, the electrodes 605, 610, 615, 620 can be placed longitudinally or transversely or in any orientation relative to the length of the esophagus 600 and can be implemented in the same exemplary combinations described in relation to FIG. 5. It should be appreciated that not all of the electrodes shown in FIG. 5 need to be implanted or operated concurrently. For example, to achieve any of the aforementioned therapeutic objectives, only one pair of electrodes, such as 505 and 510 or 515 and 520 need be implanted and/or operated concurrently.

Figure 7:
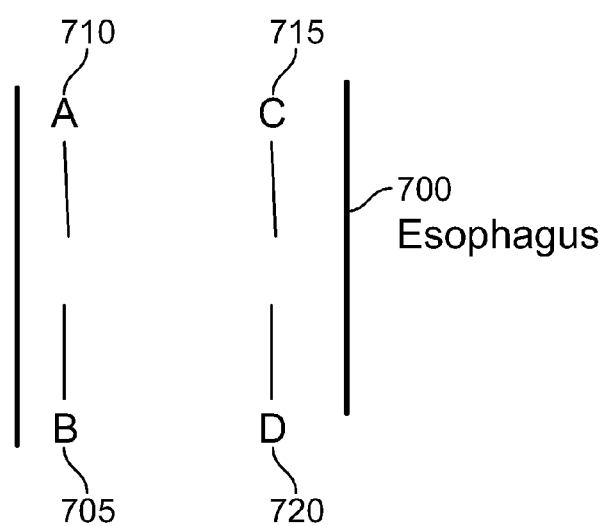
FIG. 7 depicts another exemplary electrode configuration in the esophagus of a patient.

In another embodiment, shown in FIG. 7, electrodes can be implanted in series with two electrodes 710, 705 proximate the left lateral wall of the esophagus 700 and two electrodes 715, 720 proximate the right lateral wall of the esophagus 700. These electrodes can be activated in various combinations, as described above, to provide for the optimal normalization of LES pressure, with minimal energy delivered to the tissue and minimal muscle fatigue or depletion of neurotransmitter storages. It should be appreciated that, in one embodiment, stimulation parameters (amplitude, timing of stimulation session and switching of electrode configuration) will be set so as to activate release of the appropriate neurotransmitter. Such parameters can vary between patients due to surgical variation and physiological sensitivity. The electrode activation or implantation combinations can include electrodes 710 and 715, electrodes 710 and 705, electrodes 715 or 720, electrodes 710/715 alternating with 705/720, and electrodes 710/705 alternating with 715/720.

It should be appreciated that the length and surface area of the electrode and the distance between the electrodes can affect the degree and duration of the patient's post-stimulation normalization of LES function. It should further be appreciated that the length and surface area of the electrode can affect the current amplitude required to increase LES pressure post-stimulation.

In one embodiment, a patient is treated to achieve any one of the aforementioned therapeutic objectives by implanting the electrodes in a "linear" configuration. This is accomplished by implanting a first electrode axially along the length of the smooth muscle of the LES, shown as 515 in FIG. 5, and implanting a second electrode 520 below and substantially in alignment with the first electrode 515. In various embodiments, the bottom of the first electrode 515 is separated from the top of the second electrode 520 by a distance of no greater than 5 cm, preferably no greater than 2 cm, and most preferably approximately 1 cm. Each electrode is placed preferably more than 1 mm away from the vagal trunk. This electrode configuration is supplied with a stimulation pulse from a stimulator. The stimulation pulse may be delivered in accordance with any of the aforementioned stimulation parameters. In one embodiment, the stimulation pulse has a pulse amplitude no greater than 15 mAmp and more preferably no greater than 8 mAmp. In one embodiment, the stimulation pulse has a pulse width of approximately 200 μsec and a pulse repetition frequency of 20 Hz. A stimulator may further be configured to detect any of the aforementioned biological parameters, including LES pressure. In one embodiment, the LES pressure is derived from a sensor adapted to generate an impedance measurement. In one embodiment, LES pressure is derived from piezoelectric sensors or electrical activity based sensors.

In one embodiment, a patient is treated to achieve any one of the aforementioned therapeutic objectives by implanting the electrodes in a "parallel" configuration. Referring again to FIG. 5, this is accomplished by implanting a first electrode 505 axially along the length of the smooth muscle of the LES and implanting a second electrode 510 axially on the other side of the esophagus 500, parallel to the first electrode 505. In one embodiment, the distance between the first electrode 505 and the second electrode 510 is less than half the circumference of the LES. The electrodes 505, 510 are implanted in the anterior portion of the LES, with preferably at least one electrode being in the right anterior portion of the LES (this places the stimulation as far as possible from the heart). Each electrode is placed preferably more than 1 mm away from the vagal trunk. This electrode configuration is supplied with a stimulation pulse from a stimulator. The stimulation pulse may be delivered in accordance with any of the aforementioned stimulation parameters. In one embodiment, the stimulation pulse has a pulse amplitude no greater than 15 mAmp and more preferably no greater than 8 mAmp. In one embodiment, the stimulation pulse has a pulse width of approximately 200 μsec. A stimulator may further be configured to detect any of the aforementioned biological parameters, including LES pressure. In one embodiment, the LES pressure is derived from a sensor adapted to generate an impedance measurement. In one embodiment, LES pressure is derived from piezoelectric sensors or electrical activity based sensors.

Referring now to FIG. 6, in one embodiment, a patient is treated to achieve any one of the aforementioned therapeutic objectives by implanting a first electrode 615 transaxially across the length of the smooth muscle of the LES and implanting a second electrode 620 substantially parallel to the first electrode and spaced apart from the first electrode 615 by a distance of no greater than 5 cm. This electrode configuration is supplied with a stimulation pulse from a stimulator. The stimulation pulse may be delivered in accordance with any of the aforementioned stimulation parameters. In one embodiment, the stimulation pulse has a pulse amplitude no greater than 15 mAmp and more preferably no greater than 8 mAmp. In one embodiment, the stimulation pulse has a pulse width of approximately 200 μsec. A stimulator may further be configured to detect any of the aforementioned biological parameters, including LES pressure. In one embodiment, the LES pressure is derived from a sensor adapted to generate an impedance measurement. In one embodiment, LES pressure is derived from piezoelectric sensors or electrical activity based sensors.

In one embodiment, a patient is treated to achieve any one of the aforementioned therapeutic objectives by implanting a first electrode and a second electrode in a configuration that concentrates current density at two or fewer points close to each electrode. This electrode configuration is supplied with a stimulation pulse from a stimulator. The stimulation pulse may be delivered in accordance with any of the aforementioned stimulation parameters. In one embodiment, the stimulation pulse has a pulse amplitude no greater than 15 mAmp and more preferably no greater than 8 mAmp. In one embodiment, the stimulation pulse has a pulse width of approximately 200 μsec.

In one embodiment, a patient is treated to achieve any one of the aforementioned therapeutic objectives by implanting a first electrode and a second electrode in a configuration that avoids distributing substantially all of the current density along the length of each electrode.

This electrode configuration is supplied with a stimulation pulse from a stimulator. The stimulation pulse may be delivered in accordance with any of the aforementioned stimulation parameters. In one embodiment, the stimulation pulse has a pulse amplitude no greater than 15 mAmp and more preferably no greater than 8 mAmp. In one embodiment, the stimulation pulse has a pulse width of approximately 200 μsec.

Variations in the stimulation and placement of electrodes also convey the added benefit of avoiding muscle fatigue and tolerance, as previously discussed. For example, as shown in FIG. 6, two pairs of electrodes, 605/610 and 615/620, can be implanted and stimulated in alternative succession. In one embodiment, the two pairs of electrodes receive simultaneous stimulations with the same stimulation parameters. In another embodiment, the two pairs of electrodes receive sequential stimulations with the same stimulation parameters. In another embodiment, the two pairs of electrodes receive simultaneous stimulations with different stimulation parameters. In another embodiment, the two pairs of electrodes receive sequential stimulations with different stimulation parameters. Electrode placement can also be manipulated to decrease muscle fatigue and tolerance. In one embodiment, the two pairs of electrodes are placed so that the distance between any set of electrodes is less than two times the distance between the pair of electrodes, resulting in the stimulation from a set of electrodes stimulating less than 100% of the LES.

Preferably, during the implantation process, electrode configurations are tested to verify that the proper configuration has been achieved. In one embodiment, a catheter or endoscope configured to measure LES pressure in combination with a manometer is advanced to a location proximate the implantation area while the newly implanted electrodes are stimulated. LES pressure is measured before, during, and/or after stimulation. If the desired LES pressure profile is achieved, the implantation is deemed successful and the testing may terminate. If the desired LES pressure profile is not achieved, the electrode configuration may be modified. LES pressure testing is then repeated until the proper LES pressure profile is achieved. Other sensed data, such as temperature, may also be used in this testing process. It should be appreciated that the testing process can be conducted separate from the implantation procedure. For example, patients can be tested with temporary electrodes, inserted non-invasively (nasogastrically, for example), and upon success can be deemed suitable for implant.

Device for Preventing a Hiatal Hernia

In one embodiment, the present specification provides a method of preventing the formation or recurrence of a hiatal hernia in a patient with gastroesophageal reflux disease (GERD), comprising the following steps: implanting a first, proximate end of a device in the lower esophageal sphincter of a patient and, implanting a second end, opposite the first end, of the device in the anterior abdominal wall of the patient; wherein the device prevents formation or recurrence of a hiatal hernia over time.

In one embodiment, the device is a lead as described in the present specification and the presence of the lead in the patient's LES prevents the formation or recurrence of a hiatal hernia. In one embodiment, the device functions like a string or strap that is anchored in the abdomen and acts mechanically to prevent the formation or recurrence of a hiatal hernia. In another embodiment, electrical stimulation provided by the device prevents the formation or recurrence of a hiatal hernia. In another embodiment, the formation or recurrence of a hiatal hernia is prevented both by the physical presence of the device and by the electrical stimulation provided by the device. In one embodiment, the device has a slack to allow for physiological movement in the LES. In one embodiment, the slack is between 1 and 10 cm. In another embodiment, the slack is between 2 and 5 cm. In various embodiments, the device has a tensile strength in a range of 1 to 100 newtons (N). In one embodiment, the device has a tensile strength of 20 N. In one embodiment, the device is made of a biocompatible material.

Figure 8A:
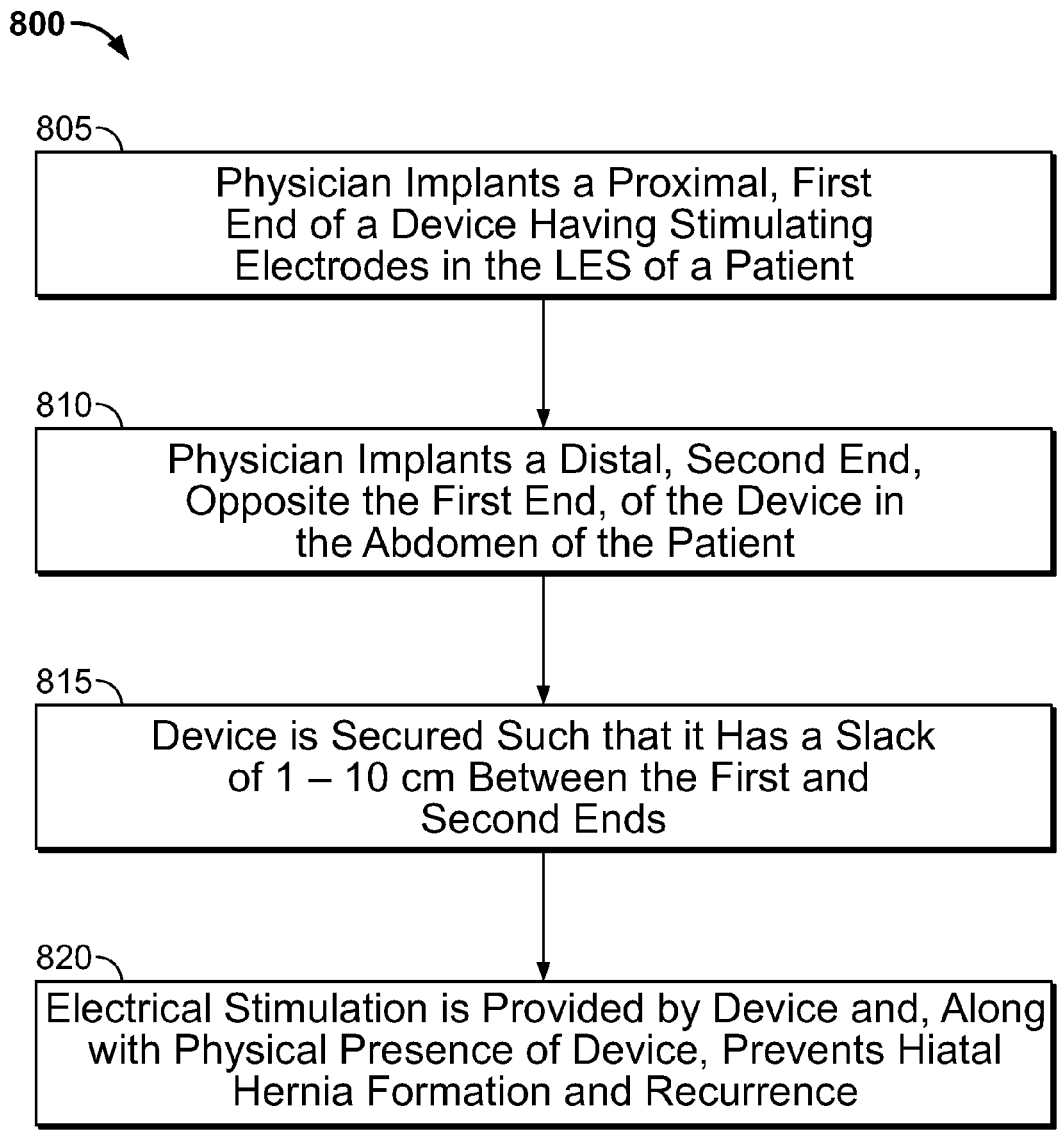
FIG. 8A is a flowchart listing the steps involved in one embodiment of a method of preventing a hiatal hernia in a patient with GERD using a device of the present specification.

FIG. 8A is a flowchart 800 listing the steps involved in one embodiment of a method of preventing a hiatal hernia in a patient with GERD using a device of the present specification. At step 805 a physician implants a proximal, first end of a device in the LES of a patient suffering from GERD. The first end includes at least one stimulating electrode. Then, at step 810, the physician implants a distal, second end, opposite the first end, of the device in the abdomen of the patient. The second end includes a pulse generator. The device is secured such that it includes a slack in a range of 1 to 10 cm between the first and second ends at step 815. At step 820, electrical stimulation is provided by the device to the LES and the stimulation, along with the physical presence of the device, prevents hiatal hernia formation and recurrence.

Device for Interfering with Esophageal Foreshortening

In one embodiment, the present specification provides a method of preventing esophageal foreshortening in a patient with gastroesophageal reflux disease (GERD), comprising the following steps: implanting a first, proximate end of a device in the lower esophageal sphincter of a patient and, implanting a second end, opposite the first end, of the device in the anterior abdominal wall of the patient; wherein the device interferes with the foreshortening of the esophagus. The present specification hereby incorporates by reference U.S. patent application Ser. No. 13/463,803, entitled "Device and Implantation System for Electrical Stimulation of Biological Systems", filed on May 3, 2012 and assigned to the applicant of the present invention, in its entirety.

In various embodiments, the device interferes with foreshortening of the esophagus in any one or combination of the following manners: a reduction in the length of esophageal foreshortening; a reduction in the duration of esophageal foreshortening; a reduction in the number of esophageal foreshortening events; and, a reduction in the number of esophageal foreshortening events associated with a reflux event. In one embodiment, the device reduces the length of esophageal foreshortening by at least 10%. In one embodiment, the device reduces the duration of esophageal foreshortening by at least 10%. In one embodiment, the device reduces the number of esophageal foreshortening events and/or esophageal foreshortening events associated with a reflux event by at least 10%.

In one embodiment, the device is a lead as described in the present specification and the physical presence of the lead in the patient's LES prevents esophageal foreshortening. In one embodiment, the device functions like a string or strap that is anchored in the abdomen and acts mechanically to interfere with esophageal foreshortening. In another embodiment, electrical stimulation provided by the device prevents esophageal foreshortening. In another embodiment, esophageal foreshortening is prevented both by the physical presence of the device and by the electrical stimulation provided by the device. In one embodiment, the device has a slack to allow for physiological movement in the LES. In one embodiment, the slack is between 1 and 10 cm. In another embodiment, the slack is between 2 and 5 cm. In various embodiments, the device has a tensile strength in a range of 1 to 100 newtons (N). In one embodiment, the device has a tensile strength of 20 N. In one embodiment, the device is made of a biocompatible material.

Figure 8B:
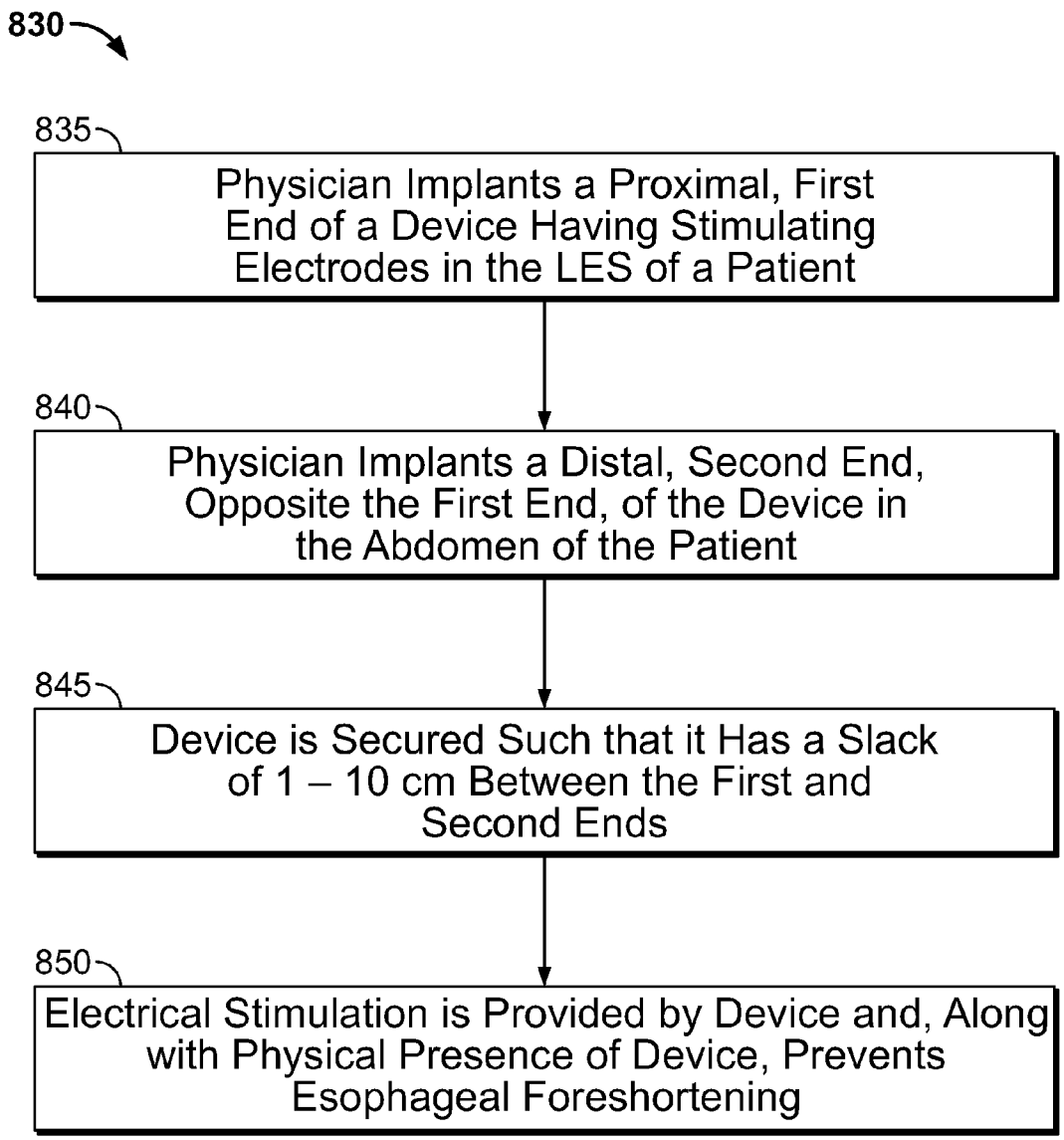
FIG. 8B is a flowchart listing the steps involved in one embodiment of a method of preventing esophageal foreshortening in a patient with GERD using a device of the present specification.

FIG. 8B is a flowchart 830 listing the steps involved in one embodiment of a method of preventing esophageal foreshortening in a patient with GERD using a device of the present specification. At step 835 a physician implants a proximal, first end of a device in the LES of a patient suffering from GERD. The first end includes at least one stimulating electrode. Then, at step 840, the physician implants a distal, second end, opposite the first end, of the device in the abdomen of the patient. The second end includes a pulse generator. The device is secured such that it includes a slack in a range of 1 to 10 cm between the first and second ends at step 845. At step 850, electrical stimulation is provided by the device to the LES and the stimulation, along with the physical presence of the device, prevents foreshortening of the esophagus.

Stimulator Energy Storage and Sensing Systems
Non-Sensing Active Implantable Medical Devices The embodiments disclosed herein achieve one or more of the above listed therapeutic objectives using stimulation systems that are energy efficient and do not require sensing systems to identify wet swallows, bolus propagation, or patient symptom changes, thereby enabling a less complex, smaller stimulation device which can more readily be implanted using endoscopic, laparoscopic or stereotactic techniques. The disclosed stimulation methods permit a natural wet or bolus swallow to override the electrically induced stimulation effect, thereby allowing for a natural wet or bolus swallow without having to change, terminate, or modify the stimulation parameters.

It should be appreciated that, in one embodiment, the stimulation device receives energy from a remote energy source that is wirelessly transmitting ultrasound or RF based energy to the stimulation device, which comprises receivers capable of receiving the energy and directing the energy toward stimulating one or more electrodes. It should further be appreciated that the device may be voltage driven or current driven, depending upon the chosen embodiment.

It should be appreciated that, in another embodiment, the stimulation device is a macrostimulator that receives energy from a local energy source, such as a battery, and directs the energy toward stimulating one or more electrodes. It should further be appreciated that the device may be voltage driven or current driven, depending upon the chosen embodiment.

By not requiring sensing systems that identify wet swallows, bolus propagation, or patient symptom changes, at least certain embodiments can operate with increased reliability and also be smaller in size. The smaller device size results in increased patient comfort, allows for placement (implantation) in the patient in more appropriate and/or convenient locations in the patient's anatomy, and allows for the use of different surgical techniques for implantation (laparoscopic, endoscopic) and/or smaller incisions, which are less invasive, cause less trauma and tissue damage, and have less risk of infection. The small size can also allow placement of a larger number of devices so as to provide redundancy, improved clinical efficacy, durability and reliability.

In addition to the absence of certain components which, conventionally, were required to be part of such an electrical stimulation system, embodiments of the present specification can achieve the above-listed therapeutic objectives using stimulation systems that operate at low energy levels, such as at or below 20 Hz with a current of at or below 8 mAmp, preferably 3 mAmp, and a pulse width of 200 μsec.

As a result of the operative energy range, the following benefits can be achieved: a) a wider range of electrode designs, styles, or materials may be implemented, b) the need to use special protective coatings on electrodes, such as iridium oxide, or titanium nitride, while still maintaining electrode surface areas below 5 $mm^2$, can be eliminated, c) one has the option of using small electrode surface areas, preferably below a predefined size with coatings to increase the effective surface area, such as iridium oxide, or titanium nitride, d) one can operate in wireless energy ranges that are within regulatory guidelines and safety limits and do not pose interference issues, such as a RF field strength below a predefined limit and ultrasound field strength below a predefined limit.

It should further be appreciated that the presently disclosed systems can be implemented using a variety of surgical techniques, including laparoscopic and endoscopic techniques. In one embodiment, a laparoscopically implanted device comprises a battery providing local energy storage and only optionally receives energy through wireless transfer, such as RF or ultrasound. In such an embodiment, the device stimulates at a higher amperage for shorter periods of time, relative to embodiments without local energy storage, thereby allowing for longer off cycles, lower duty cycles, and better battery efficiency. In one embodiment, an endoscopically implanted device may or may not comprise a local energy storage device but does comprise a wireless receiver to receive energy wirelessly transmitted from an external energy source and transmission device. In such an embodiment, this device stimulates at a lower energy setting for longer on cycles and shorter off cycles, relative to the embodiment with local energy storage, thereby having a greater duty cycle than a laparoscopic implant.

The stimulators of the present specification, when properly programmed in accordance with the stimulation parameters described herein and associated with the appropriate electrode configurations, exhibit a high degree of energy efficiency. In one embodiment, the electrical stimulation device initiates electrical stimulation based upon an internal clock or a patient activated trigger. Electrical stimulation then continues for a preset or predefined period of time. Referencing a 24 hour period of time, the preset or predefined period of time may be equal to an "on" time period that is less than or equal to 24 hours, 12 hours, 1 second, or any increment therein. Upon completion of that predefined period of time, the internal clock then causes the electrical stimulation device to terminate electrical stimulation.

It should be appreciated that any activation by an internal clock can be configured to cycle daily or a few times daily or be synchronized to meal times, as signaled manually by a patient. It should further be appreciated that the timing of meal times or other physiologically relevant events can be saved and/or learned, thereby enabling the device to default to standard initiation of stimulation time or termination of stimulation time based upon past data gathered. The setting of stimulation times may be set by a physician, based on an interview with a patient or based on the detection of eating using pH sensing or some other automated eating detection mechanism. In one embodiment, stimulation is initiated in advance of a predefined meal time to achieve a decrease in LES tone before the patient eats. For example, if a patient's predefined meal time is 2 pm, then stimulation is set to initiate in advance of 2 pm, such as 1:30 pm. If a patient's predefined meal time is 12 pm, then set stimulation is set to initiate in advance of 12 pm, such as 11:30 am.

In another embodiment, the electrical stimulation device initiates electrical stimulation based upon an internal clock or a patient activated trigger. Electrical stimulation then continues for a preset or predefined period of time. Upon completion of that predefined period of time, the internal clock then causes the electrical stimulation device to terminate electrical stimulation. This ratio of the predefined period of stimulation relative to the time where electrical stimulation is terminated is less than 100%, up to a maximum duty cycle, such as 70%, 75%, 80%, 85%, 90%, 95%, or any increment therein.

In another embodiment, the electrical stimulation device initiates electrical stimulation based upon an internal clock or a patient activated trigger. Electrical stimulation then continues for a preset or predefined period of time. The preset or predefined period of time may be equal to a time period that is up to a maximum "on" period, such as 12 hours, during which the device may be continually operating. Upon completion of that predefined period of time, the internal clock then causes the electrical stimulation device to terminate electrical stimulation.

In another embodiment, the electrical stimulation device initiates electrical stimulation based upon an internal clock or a patient activated trigger. Electrical stimulation then continues for a preset or predefined period of time. The preset or predefined period of time may be equal to a time period that is up to a maximum "off" period, such as 12 hours, during which the device is not operating. Upon completion of that predefined period of time, the internal clock then causes the electrical stimulation device to restart electrical stimulation.

In another embodiment, the electrical stimulation device initiates electrical stimulation based upon an internal clock or a patient activated trigger. Electrical stimulation then continues for a preset or predefined period of time. The preset or predefined period of time may be equal to a time period that is less than the time required to see a visible change in the LES pressure. Upon completion of that predefined period of time, the internal clock then causes the electrical stimulation device to terminate electrical stimulation. The desired decrease in LES pressure occurs post-stimulation, followed by an increase in LES pressure which still remains below a pre-stimulation state after a period of >1 hour.

It should be appreciated that other stimulation protocols, which result in the desired effect of operating for less than 100% of duty cycle and which have a preset or predefined period of non-stimulation, can be achieved using combinations of turning on and off subsets of electrodes at different times. For example, one may turn a first subset of electrodes on, turn a second subset of electrodes on, then turn all electrodes off, followed by turning a second subset of electrodes on, turning a first subset of electrodes on, and then all electrodes off again.

Sensing Active Implantable Medical Devices

It should be appreciated that the stimulating devices of the present specification can be optionally operated in combination with sensing systems capable of sensing physiological events, such as eating, swallowing, a bolus propagating through the esophagus, muscle fatigue, pH level, esophageal pressure, tissue impedance, LES tone/pressure, patient position, sleep state, or wake state. In such a case, a physiological event can be used to modify the stimulation schedule by, for example, extending the stimulation time period based upon sensed pH level, eating, swallowing, or a bolus propagating through the esophagus or, for example, terminating the stimulation period before the preset time period expires based upon sensed muscle fatigue.

It should also be appreciated that the stimulating devices of the present specification can be driven by, and fully triggered by, sensing systems capable of sensing physiological events, such as eating, swallowing, a bolus propagating through the esophagus, muscle fatigue, pH level, esophageal pressure, tissue impedance, LES tone/pressure, patient position, sleep state, or awake state. In such a case, a physiological event can be used to initiate the stimulation schedule.

By operating the stimulation system less than 100% duty cycle and having the stimulation device switched off during preselected periods, the presently disclosed stimulation system uses less energy than prior art devices. Accordingly, the stimulation systems disclosed herein can effectively operate to achieve the above-listed therapeutic objectives using an energy source local to the stimulator that a) does not include a battery, b) includes a small battery capable of being recharged from an external energy source, c) only includes a capacitor and, more specifically, a capacitor having a rating of less than 0.1 Farads or d) only includes a battery that is not rechargeable.

In one embodiment, a stimulator uses a remote data sensor for automatically adjusting parameters. The stimulator comprises stimulating circuitry contained within a housing that includes a power source, means for delivering stimulation, a receiver to collect data from a remote sensor and a control unit that analyzes the data received from the receiver and adjusts the stimulation parameters based on a plurality of stored programmatic instructions and the received data. The means for stimulation may include any form of leaded or a leadless device. The stimulator element would preferably be implanted either under the skin, in cases where the stimulator comprises a macrostimulator internal pulse generator (IPG), or close to the stimulation area, in cases where the stimulator comprises a microstimulator. The stimulator can also comprise a plurality of separate units, in separate housings, including, for example, an external control unit and receiver and an implantable stimulator, similar to a passive microstimulator.

The stimulator is in wireless or wired data communication with one or more sensor elements. The sensor elements are implanted in an area that allows the sensor to collect physiological data relevant to controlling the operation of the stimulator. Each sensor element includes means for sensing the required physiological function and means for transmitting the data to the control unit. In one embodiment, the sensor element comprises a capsule adapted to measure physiological pH and transmit pH data from within the lumen of the esophagus to an implantable stimulator device. In another embodiment, the sensor element comprises a pH sensor located within a nasogastric tube and means for transmitting the pH data to an implanted control unit. In another embodiment, the stimulator comprises electrodes implanted in the LES that are wired to an implantable IPG, which is in data communication with a pH measuring element, such as but not limited to a pH capsule or a catheter based device, that is transmitting pH data to the device via uni-directional or bi-directional communication.

In another embodiment, the stimulator/sensing system disclosed herein can locally store a plurality of programmatic instructions that, when executed by circuitry within the IPG, uses data received from a capsule to automatically refine stimulation parameters within a pre-defined range of boundaries. The data may be continuously streamed from the sensing capsule to the IPG and may be subject to continuous monitoring and processing. The data may comprise any one of pH data, pressure data, LES pressure data, temperature, impedance, incline, or other physiological data.

Figure 9A:
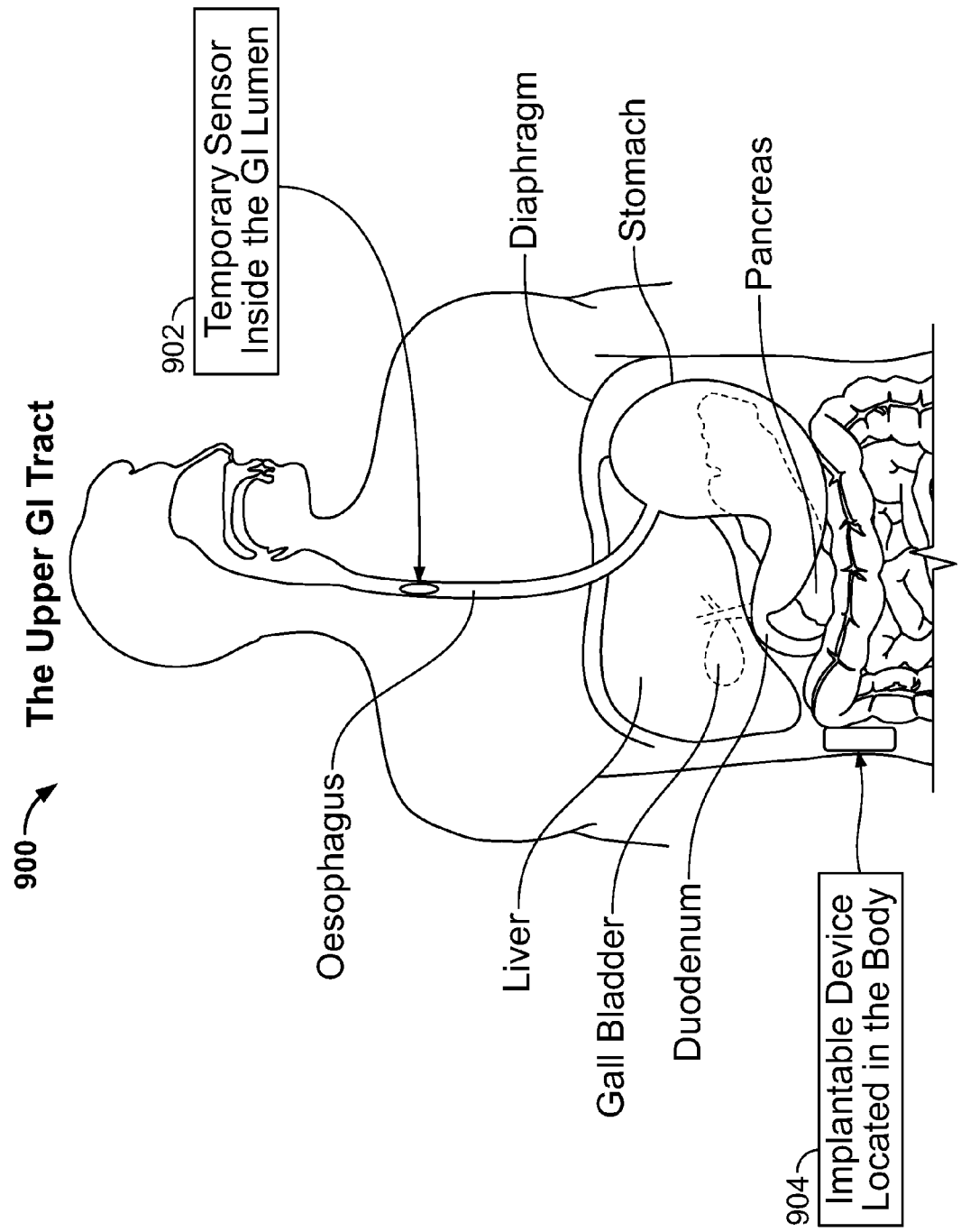
FIG. 9A is a cross-sectional illustration of the upper gastrointestinal tract showing a pH sensing capsule in the esophagus and a stimulator adapted to be implanted within the tissue of the patient.

Referring to FIG. 9A, a patient 900 has implanted within his tissue a stimulator 904, as further described below. The stimulator 904 is adapted to dynamically communicate with a temporary sensor 902, as further described below, which may be located inside the patient's GI lumen. The implanted stimulator 904 comprises stimulator circuitry and memory having programmatic instructions that, when executed, perform the following functions: transmit an interrogating signal designed to elicit or cause a transmission of sensed data from the temporary sensor 902 or receive a transmitted signal comprising sensed data from the temporary sensor 904 and process the sensed data to modify stimulation parameters, such as frequency, duration, amplitude, or timing. Optionally, the stimulator 904 may also analyze the received sensed data signal to determine if the data is reliable. The implanted stimulator 904 is adapted to only modify stimulation parameters or otherwise engage in a processing routine adapted to use the sensed data to determine how the simulation parameters should be modified when it senses and receives the sensed data. Optionally, the implanted stimulator 904 is adapted to modify stimulation parameters or otherwise engage in a processing routine adapted to use the sensed data in combination with patient data inputted into an external device to determine how the simulation parameters should be modified.

For example, in one embodiment, when a meal event, sleeping event, or other event which may cause, be related to, or be associated with an achalasia event, is expected to occur at a specific time during the day (either because previously sensed data has determined a pattern indicating the existence of such an event or because patient data expressly indicates that such an event should be expected), stimulation parameters may be modified or otherwise established in order to provide the requisite level, degree or amount of stimulation before the anticipated event, such as 5 minutes, 10 minutes, 30 minutes, 45 minutes, 60 minutes, 90 minutes, 120 minutes, or some increment therein. The determination of stimulation parameters, including start time, end time, pulse frequency, duration, ramp rate, duty cycle, and/or amplitude, can be determined independent of the patient's immediate physiological state and is not causally related to the patient's existing condition. Rather, historical data patterns from sensors, including pressure data, LES pressure data, temperature, impedance, incline, or other physiological data, can be used to define the achalasia profile of a patient, namely when, in the course of a day, a patient is likely to experience achalasia. Results from the historical data patterns are then used to proactively normalize LES function in advance of a achalasia event. To properly generate and mine data patterns, it is preferable to capture both the magnitude of the physiological data (i.e. pH<4), the duration (for one hour), and the timing (around 1 pm). It is further preferable to associate different physiological data to see if a predictive pattern may exist between data sets and to further correlate that data with the patient's own reporting of a, pain, discomfort, or other sensations to better determine when an achalasia event is likely to occur in a day.

In one embodiment, the implanted stimulator 904 is configured to check the reliability of the data by processing it to determine whether the data is indicative of the sensor being in an improper location. In one embodiment, wherein the temporary sensor is a capsule measuring pH data intended to measure esophageal pH, such a determination process may be conducted by: a) monitoring the received pH data over a predefined period of time to determine if it is indicative of a high pH environment, such as the patient's stomach as opposed to the esophagus, b) monitoring the received data signal, such as an RF signal, over a predefined period of time to determine if the signal strength has significantly changed or modified, indicating a change in physical location, or c) monitoring a received accelerometer or inclinometer data signal from the pH capsule, over a predefined period of time, to determine if the capsule is in a proper physical orientation. Depending on the reliability check, the implanted stimulator 904 may use, or discard, the sensed data. If no reliable data is received by the implanted stimulator 904, it does not modify stimulation parameters or otherwise engage in a processing routine adapted to use the sensed data to determine how the simulation parameters should be modified. If reliable data is received by the implanted stimulator 904, it modifies stimulation parameters or otherwise engages in a processing routine adapted to use the sensed data to determine how the simulation parameters should be modified.

In one embodiment, the temporary sensor 902 stores the sensed and transmitted data and transmits the stored data to an external reading device. It should be appreciated that the previously discussed methods for using sensed data, whether from a temporary sensor or permanently implanted sensor, may be performed by an external device. For example, in one embodiment, an external device wirelessly receives sensed data and uses the sensed data to determine a pattern indicative of when an achalasia event is likely to be experienced by a patient. Any pattern analysis method known to persons of ordinary skill in the art may be used. The data may include some or all of the sense data, externally inputted patient data, or a combination thereof. As discussed above, the external device would use the data to determine the time(s) of day when a patient typically experiences an achalasia event and the appropriate stimulation parameters required to normalize LES function prior to such achalasia event. In one embodiment, the requisite stimulation parameters are determined by examining historical achalasia events in relation to stimulation parameters that had been implemented and modifying the stimulation parameters to increase or decrease the magnitude or duration of the stimulation accordingly. Additionally, in one embodiment, the implanted stimulator 904 stores the sensed data and data indicative of how stimulation parameters, such as frequency, duration, amplitude, or timing, were modified based on the sensed data, and transmits the stored data to an external reading device.

Figure 9B:
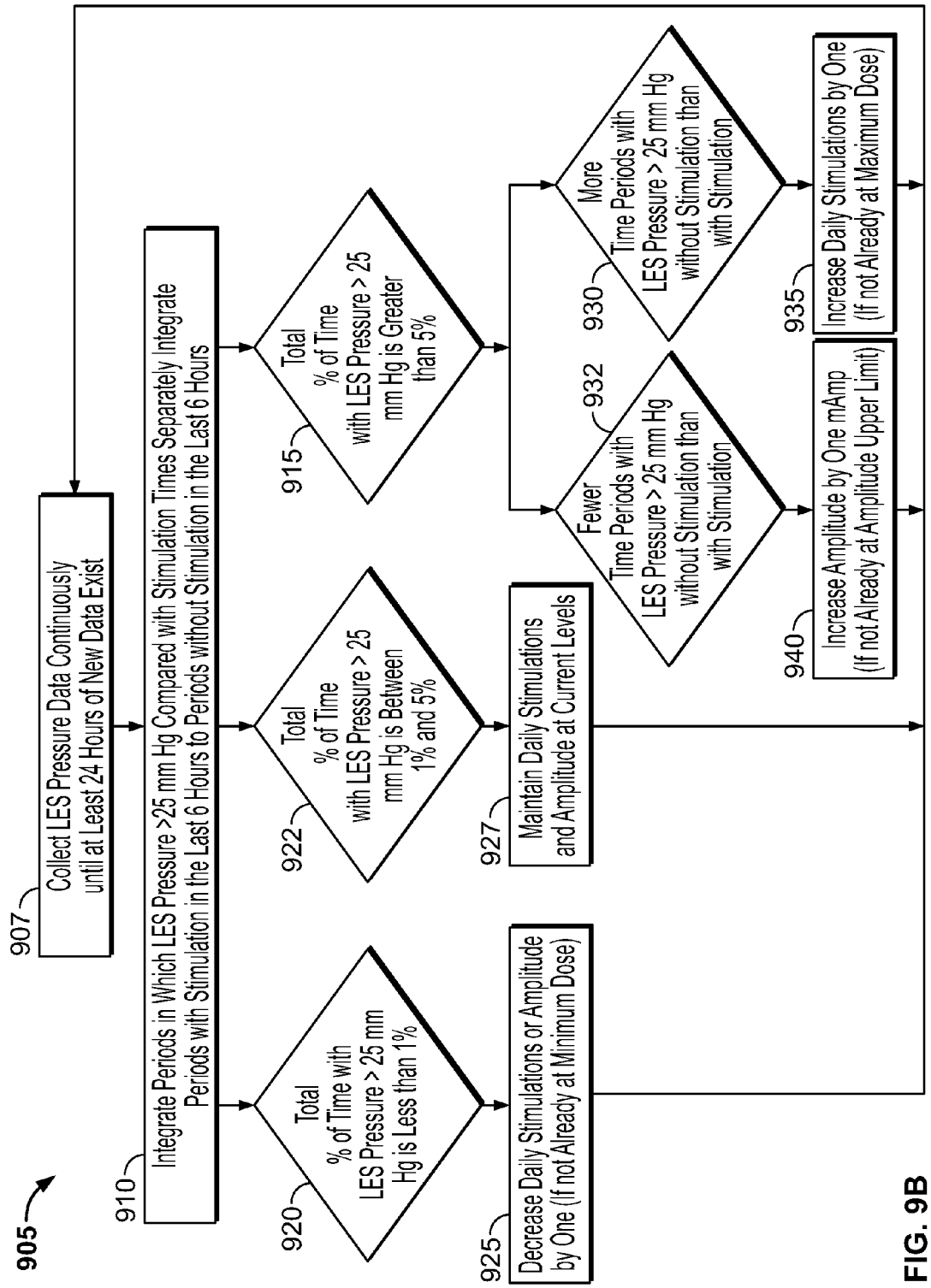
FIG. 9B is a flow sheet depicting a certain parameter setting method of one embodiment of the present invention.

Referring to FIG. 9B, in one embodiment, the process 905 implemented by the stimulator system comprises collecting 907 LES pressure data periodically or continuously over a predefined period, such as 1, 2, 6, 12, 24, 36, 48, or 60 hours, or any time increment in between. Circuitry within the stimulator analyzes the LES pressure data 910 to determine if, within the predefined period, such as 24 hours, LES pressure is greater than a predefined value, such as 25 mm Hg, for a percentage of time higher than a threshold value, such as 1, 2, 3, 4, 5, 10, 15, or 20 hours, or any increment therein 915. The processor may analyze LES pressure data 910 by integrating periods in which the LES pressure is greater than the predefined value compared with stimulation times and separately integrate periods with stimulation in a most recent time period (i.e. last 6 hours) to periods without stimulation in the most recent time period.

In one embodiment, if the percentage of time with the LES pressure greater than the predefined value within a predefined period is lower than a threshold value, such as 1 percent or lower 920, then the circuitry may adjust stimulation parameters 925 so as to reduce the timing, frequency, or size of the stimulation doses. In one embodiment, the circuitry decreases daily stimulations or amplitudes by a discrete amount, such as 1 mAmp. In one embodiment, the system may not reduce the timing, frequency, or size of the stimulation doses below a minimum dose.

If the percentage of time with the LES pressure greater than the predefined value within a predefined period is within a pre-determined range of values, for example, in one embodiment, between 1% and 5% of the total percentage of time 922, then the circuitry will not adjust the stimulation parameters 927 and the current therapy will be maintained.

In one embodiment, if the percentage of time with the LES pressure greater than the predefined value within a predefined period is greater than a threshold value, such as 5 percent or higher 915, then the circuitry will further analyze if there were more periods with LES pressure greater than the threshold value during time periods in which there was no stimulation or during time periods in which there was stimulation. If there were more periods with LES pressure greater than the threshold value during time periods without stimulation than with stimulation 930, the circuitry may increase the number of daily stimulations by a discrete amount, such as by 1 935 or increase the duty cycle or length of a given stimulation session or duration by a discrete amount, such as 1 minute. By doing so, the system assumes the amount of energy delivered per stimulation is sufficient, but there simply were not enough stimulation events in a day, or the stimulation was not long enough. If there were more periods with LES pressure greater than the threshold value during time periods in which there was stimulation than without stimulation 932, the circuitry increases the amplitude of stimulations by a discrete amount, such as by 1 mAmp 940. By doing so, the system assumes the amount of energy delivered per stimulation was not sufficient and therefore increases the energy delivered per stimulation. In one embodiment, the system may not increase the timing, frequency, or size of the stimulation doses above a maximum dose.

In general, if the percentage of time within a predefined period during which LES pressure is greater than a threshold value, such as 25 mm Hg, is higher than an upper value, such as 5%, then the stimulation parameters will be adjusted so as to increase dose. Also, if the percentage of time within a predefined period during which LES pressure is greater than a threshold value, such as 25 mm Hg, is lower than a lower value, such as 1%, then the stimulation parameters may be adjusted so as to reduce dose. The decreasing and increasing of dose will be done based on the temporal behavior of the LES pressure values. It should be appreciated that doses may be incremented by any amount. It should further be appreciated that doses can be effectively decreased or increased by increasing one parameter while reducing another parameter so that the total energy is increased, reduced, or unchanged. Finally, it should be appreciated that all modifiable parameters will be bounded, on at least one of the maximum or minimum boundary, by a range defined by a healthcare provider.

In another embodiment, the operation of the system is augmented with other sensed data. Where the system is being used to stimulate the LES or treat achalasia, LES pressure data can be augmented with accelerometer and/or inclinometer data. The accelerometer or inclinometer sensor(s) could be located within the implantable device or in another device on or inside the patient body. This additional data can enable the control unit algorithm to assess patient modes (e.g., sleep, exercise, etc) and improve the tuning of stimulation parameters for a specific patient, thereby improving device efficacy and/or efficiency. Additional sources of information may include, but not be limited to, esophageal body pressure measurements or an impedance measurement by a capsule or an eating detection mechanism using one or more sources such as impedance or other electrical or electromechanical measurement from within the tissue or from the lumen. These additional sources of information can further be used by the control unit to adjust the stimulation dose and other parameters and other functions of the implantable device. It should be appreciated that any of the aforementioned data may be used individually or in combination to modify the operation of the system and, in particular, to determine how stimulation parameters should be modified to address an anticipated patient achalasia event.

In another embodiment, the system logs the sensed and computed data and downloads the data to an external device for viewing and analyzing by a medical professional or a technician. By permitting on-demand or batch downloading, the system can eliminate the need for the patient to carry an external receiver during LES pressure sensing, thereby improving the use experience of the patient and potentially improving compliance and allowing for longer measurement periods. The system can download data automatically and without any requirement for user intervention, such as when an appropriately calibrated external device comes within a data communication area of the implanted device, or semi-automatically, such as when initiated by the implantable device when the implantable device is in proximity (communication distance) of the external device and the user has provided a password or other indication of approval via the external wireless interrogation device.

It should be appreciated that the external device receiving the sensed or computed data could be located at the healthcare provider's location or at the patient's home. If captured at the patient's home, the data could be automatically sent to the clinic for physician review and/or approval of suggested parameter changes via any communication medium, including Internet, Ethernet network, PSTN telephony, cellular, Bluetooth, 802.11, or other forms of wired or wireless communication. The transmitted data preferably contain the measured values, the recommended stimulation parameters adjustments, or both. Similarly, the physician approval, or physician suggested parameter changes, could be sent back to the external device located at the patient's home which, in turn, transmits appropriate commands to the implanted device, when the two devices are in proximity, to initiate the suggested parameter changes.

In another embodiment, the system monitors sensor, such as capsule, failure. If the sensor fails an internal diagnostic test, a failure or alert signal is transmitted to the implanted control unit, or the implanted control unit itself logs a failed attempt to communicate with, or obtain uncorrupted data from, the sensor. The control unit then transmits that failure or alert signal data to the external device and, in turn, to the healthcare provider, as described above, thereby alerting a healthcare provider that the patient needs to return to have the sensor fixed or another sensor implanted.

In another embodiment, the system is capable of recognizing and registering a plurality of different sensing devices, such as capsules, and re-initiate newly implanted sensors as required to ensure continuous or substantially continuous measurement. For example, the stimulator can be implanted for a long period of time, such as several months or years, and for a shorter period of time, such as once per annum, a sensor is implanted. The stimulator registers the new sensor and automatically adjusts the new sensor for operation in the particular anatomical region, such as the esophagus.

In addition to failing, sensors may migrate out of the implanted anatomical region. For example, wherein a sensor, such as a capsule, has been implanted into a patient's esophagus but has migrated to the stomach, the physical location of the sensor can be derived by examining the sensed data. For example, where a pH capsule has moved from the esophagus to the stomach, the capsule will likely transmit data indicative of extensively long periods during which the pH is highly acidic. In that case, the stimulator system can assume the capsule has migrated, report this failure to an external device, and ignore future data being transmitted from the capsule or record the data but not rely upon it for parameter setting. Similarly, the stimulation system may register a weaker or changed signal, indicative of a sensor moving a distance away from the recording device.

The presently disclosed stimulator system may further comprise a receiving antenna integrated into a stimulator system, which may be used for energy transfer to the stimulator system and communication to and from the device. The close proximity between the stimulator, particularly a miniature device, and a sensor, such as the pH capsule, can be used to achieve communication efficiency and increase durability through a miniature antenna in the stimulator that can accept data from the pH capsule. The close distance can effectively reduce power requirements and enables typical low frequency inductively coupled telemetry for transmission through titanium via coils, as well as high frequency RF communication such as MICS or IMS bands via monopole, dipole, or fractal electric field antennas. The communication distance can be further reduced by enabling anchoring of the pH capsule or nasogastric tube to the implanted control unit. This can be facilitated by, for example, a magnetic force between the two units caused by a magnet in both units or a magnet in one unit and a ferrous metal in the other.

One of ordinary skill in the art would appreciate that other means for communication can be used that will take advantage of the close proximity between the stimulating electrodes and the sensing device, such as a pH capsule, even when the control unit is farther away, thereby allowing for a significant reduction in the power consumption and improvement of reliability of communication. The stimulating electrodes in that embodiment would serve as receiving antennas and also simplify the design of the control unit, thereby avoiding the need for a receiving coil, antenna or other electromagnetic receiving means.

Bi-directional communication between the control unit and the sensor unit can be implemented as part of the system to allow, for example, calibration or activation of specific actions such as additional measurements, determination of measurements to be taken, determination of measurement times, and local stimulation by the sensor unit, among other variables. The sensor unit can also be used to not only transmit the sensed data, but also to transmit energy for charging and powering the control unit and the stimulating device. For example, pH capsules that further act as energy recharging sources can be periodically implanted, as required, to deliver energy to the control unit or a microstimulator in addition to actually sensing pH data.

Patient Selection Methods

In one embodiment, a person is permitted to practice the treatment systems and methods disclosed herein and, in particular, to have an embodiment of the electrical stimulation systems disclosed herein implanted into him or her only if the person passes a plurality of screening or filtering steps.

In one embodiment, a plurality of physiological measurements are taken of the patient and used to determine whether the patient may therapeutically benefit from the electrical stimulation treatment systems and methods disclosed herein. LES pressure data is collected from the patient. For example, LES pressure measurements are obtained over a period of time, such as 4, 8, 12, 16, 20, or 24 hours or some increment therein. The amount of time within the predefined measurement period during which the LES pressure measurement is above a predefined threshold indicative of achalasia, such as an LES pressure of 25 mm Hg, is calculated. The number of achalasia events occurring for more than a predefined period of time, such as more than 1, 3, 10, 15, or 20 minutes, or any increment therein, is determined. The total time for each achalasia event lasting more than the predefined period of time, i.e. 3 minutes, referred to as a long event, is then summed. If that total time exceeds a predefined threshold, such as 5 minutes to 240 minutes or any increment therein, it may be concluded that the patient would therapeutically benefit from the electrical stimulation treatment systems and methods disclosed herein. For example, if a patient has 4 events of achalasia lasting 1, 4, 5 and 6 minutes and the predefined threshold is 3 minutes, the total time would be equal to 15 minutes (4+5+6). If the total time threshold is 10 minutes, then the patient can be categorized as an individual who would benefit from the electrical stimulation treatment systems and methods disclosed herein.

Another physiological measurement that may be used to select eligible patients is LES end expiratory pressure (LES-EEP). In one embodiment, a patient's LES-EEP is measured and collected during resting time, e.g. no swallow for at least 30 seconds, and then compared to at least one threshold. For example, the value of the LES-EEP should be above a normal value threshold, such as 10-20 mmHg, preferably 12-18 mmHg, and more preferably 15 mmHg, in order for the patient to qualify for treatment. In another embodiment, a patient's LES-EEP is measured and collected during resting time, e.g. no swallow for at least 30 seconds, and then compared to a range of pressure values, e.g. to two different threshold values. For example, the value of the LES-EEP should be above a lower threshold, which is indicative of the LES having some base functionality, such as 0 mmHg to 3 mmHg or any increment therein and below an upper threshold, such as 8 mmHg to 10 mmHg or any increment therein.

In another embodiment, a patient's increased LES pressure times are recorded and then compared to the timing of patient's reported achalasia symptoms. The degree of temporal correlation between the increased LES pressure times and reported symptoms is then determined. Patients with a degree of correlation above a predefined threshold would be eligible for treatment while those below the predefined threshold would not be.

In another embodiment, it is determined whether a patient may therapeutically benefit from the electrical stimulation treatment systems and methods disclosed herein by temporarily stimulating the patient for a period of time, such as less than one week, using a non-permanent implanted stimulator to evaluate the patient's physiological response to stimulation and predict the patient's likely physiological response to a permanent stimulator. In one embodiment, the temporary stimulation is delivered using a temporary pacing lead endoscopically implanted in the patient's LES and connected to an external stimulator, which is either a non-portable system or a portable battery-operated device. The temporary stimulation system delivers periodic stimulations over a period of time, from 30 minutes to two weeks or more, during which the patient's symptoms, achalasia events, and physiological response are recorded and correlations between the three are determined. The temporary stimulation data can then be used to determine the likely timings of achalasia events and the required stimulation parameters to proactively normalize the patient's LES in advance of the achalasia events, as previously discussed. Once the temporary stimulation period is complete, the electrode can be removed and a decision can be made regarding whether or not the patient would therapeutically benefit from a permanent implant based, for example, on the patient's physiological response to the temporary stimulation, improvement in symptoms, and/or normalization of LES pressure.

In one embodiment, the temporary stimulator is in the shape of a small capsule-like device that is self-contained and includes all required components for stimulation including a power source or a receiver that allows power to be received wirelessly from outside the body and one or more electrodes. The device is adapted to stimulate the LES tissue. In one embodiment, the device also includes an anchoring component, such as a hook, corkscrew, rivet, or any other such mechanism, which temporarily connects it to the LES wall. The capsule is implanted through an endoscopic or catheterization procedure to the LES wall. Such a capsule is expected to remain attached to the LES wall for a period of one day to two weeks or longer and then detach by itself and leave the body naturally. Further, the device can include a sensor for detecting when it is attached to the wall, which will only stimulate when it detects that the device is still attached to the LES wall. Additionally, the device may include wireless communication to allow telemetry and/or commands to be delivered from outside the body. The capsule can additionally include pH measurement, manometry measurement or other physiological measurement devices or sensors so that the short term efficacy of the stimulation can be more easily evaluated. Additional standard measurements can be made as needed for obtaining more information.

It should be appreciated that any form of temporary stimulator could be used. For example, in various embodiments, a stimulator can include a) a plurality of implantable leads adapted to be temporarily implanted into the LES tissue through endoscopy, laparoscopy or other minimally invasive methods and further adapted to deliver stimulation to the LES, b) a housing which includes a control unit and circuitry for generating electrical stimulation, wherein the housing is adapted to be temporarily implantable and/or integrated with the leads such that the housing itself can deliver stimulation, or externally located and wired to the leads without being implantable and/or c) an additional unit capable of recording the physiological data, stimulation data, and various patient inputs (symptoms, eating, sleeping events, etc.) and adapted to be used for turning stimulation on or off. Optionally, in one embodiment, the additional unit is controlled by a physician and wirelessly programmable using a physician's computer system. Optionally, in one embodiment, the stimulator is configured to include sensors or communicate with sensors that measure the aforementioned physiological measures.

Other approaches for selecting patients based on physiological data and/or temporary stimulation can also be implemented. It should be clear to persons skilled in the art that the above selection methods could be integrated in various ways to result in an optimal selection of patients. For example, in one embodiment, one integrated method is used to screen patients by qualifying candidates according to achalasia long events, the manometry value of LES-EEP, or the number of short events, or any combination thereof. Additionally, a combination of the measures can be used such as dividing the total length of long events by the rate of short events and comparing this value against a properly adjusted threshold, such that patients with a ratio above the threshold are included and others are excluded. Once qualified, the patient can undergo the permanent implant procedure or undergo the temporary stimulation process to further qualify the patient.

Physician Diagnostic and Programming Systems and Methods

Different patients may require different therapeutic regimens, depending upon implant depth, anatomical variations, treatment objectives, and severity of the disease condition. Each patient has a different resting lower esophageal sphincter (LES) pressure and different responses to stimulation (due to expected variability in sphincter muscle condition and also in the implant location). Furthermore, changes to the patient's anatomy, for example, arising from normal healing after implantation, chronic stimulation or age, can also change the optimal stimulation dosage. Accordingly, it is preferred for a patient to first undergo a diagnostic process to determine whether, and to what extent, the patient can be treated by one of a plurality of therapeutic processes, as further described below. It is also preferred for a patient to periodically visit a physician to have the efficacy of the stimulation system checked, optimized, and possibly reprogrammed, as provided below.

In one embodiment, because the goal is to keep the sphincter at a pressure or function which eliminates or greatly reduces the chances for achalasia, it is unnecessary for the muscle to always have low pressure but, rather, it is desirable to have (1) some average pressure sustained at all times with a certain permitted range of variability around it and a minimal pressure that the sphincter will never be, or will rarely be, above or (2) some average function sustained at all times with a certain permitted range of variability around it and a minimal function that the sphincter will never be, or will rarely be, below or a combination thereof. Continuous non-stop stimulation is not optimal because the acute response of enhanced pressure may diminish over time due to neuromuscular tolerance or muscle fatigue. Furthermore, a simple "on-off" regime during which the muscle is stimulated for a first duration and then the stimulation is turned off for a second duration may be effective; however, different muscle properties, variations in the patient condition, and variations in the implant may require a different selection of the "on" and "off" periods for each patient and may also require a change in the initial selection of the "on" and "off" periods over time in the same patient.

In one embodiment, a patient's average pressure (AP) and maximal pressure (MP) are set by conducting a parameter setting test, in which a stimulator is controlled by an operator and a manometry measurement of LES pressure is made. During this test, the operator turns on the stimulation and then observes the LES pressure while keeping the stimulation on until the pressure drops below a first threshold, defined, for example, by MP-AP. When the observed pressure passes this first threshold, the stimulation is either turned off or kept on for an additional short period of up to 5 minutes and then turned off. The operator notes the time when the stimulation is turned off.

The operator continues to observe the pressure and once the pressure reaches MP, the operator turns on the stimulation again and notes the time. This measurement process continues for several hours, such as 2 to 5 hours, so that several stimulation on-off periods can be recorded. At the end of the test period, a chronic "on" time is selected to be the median of the measured "on" periods and a chronic "off" period is selected to be the median of the measured "off" periods. It should be appreciated that the initiation of stimulation, turning off of stimulation, recordation of time periods, and recordation of LES pressure can be performed automatically, based on a pre-programmed set of threshold values, by a computing device comprising a processor and memory storing the threshold and control instructions as a set of programmatic instructions.

In another embodiment, a patient's average pressure (AP) and maximal pressure (MP) is set by conducting a parameter setting test, in which a stimulator is controlled by an operator and a manometry measurement of LES pressure is made. During this test, the operator turns on the stimulation, notes the electrode impedance value, and then observes the LES pressure while keeping the stimulation on until the pressure drops below a first threshold, defined, for example, by MP-AP. When the observed pressure passes this first threshold, the stimulation is either turned off or kept on for an additional short period of up to 5 minutes and then turned off. The operator notes the time when the stimulation is turned off and the electrode impedance value when the stimulation is turned off.

The operator continues to observe the pressure and once the pressure reaches MP, the operator turns on the stimulation again and notes the time and electrode impedance value. This measurement process continues for several hours, such as 2 to 5 hours, so that several stimulation on-off periods can be recorded. Electrode impedance is measured every time the stimulation is turned "on" or "off". At the end of the test period, a chronic "on" time is selected to be the median of the measured impedance value for the "on" periods and a chronic "off" period is selected to be the median of the measured impedance value for the "off" periods. Rather than setting a stimulation device to operate based on fixed time periods, a stimulation device is programmed to turn off and on based upon the measured impedance values, where the device turns on when a patient's impedance value approaches the measured mean, median, or any other calculated impedance value for the on periods and turns off when a patient's impedance value approaches the measured median, mean, or any other calculated impedance value for the off periods. It should be appreciated that the initiation of stimulation, turning off of stimulation, recordation of time periods, recordation of electrode impedance, and recordation of LES pressure can be performed automatically, based on a pre-programmed set of threshold values, by a computing device comprising a processor and memory storing the threshold and control instructions as a set of programmatic instructions. It should be appreciated that, in addition to the above embodiments, a patient's LES pressure may be recorded by conducting a parameter setting test, in which a stimulator is controlled by an operator and a manometry measurement of LES pressure is made. The recorded LES pressures are compared to a predefined threshold to determine a minimum pressure which should preferably not be exceeded. The aforementioned on and off periods are then set or modified based on this minimum pressure data.

It should be appreciated that the use of impedance values is useful, relative to manometry measurements, if the values of the "on" and "off" periods in the acute phase do not converge to a small range within a few minutes. It should further be appreciated that other measurements, instead of impedance, can be used, including physical tension sensors (i.e. implantable strain gauge) or sensors of the muscle electrical activity or sensor of muscle pressure. Furthermore, it should be appreciated that both of the aforementioned tests can be used, and/or combined, to fix time windows for the "on" and "off" periods and rely on impedance measurements in order to adapt, modify, or change the time windows to account for a possible drift in muscle status.

In another embodiment, a doctor makes a determination regarding the LES electrical stimulation therapy (LES-EST) available to a patient by first engaging in a process for evaluating a plurality of appropriate dosing values for a patient. The evaluation process comprises subjecting a patient to a plurality of pulse sequences and measuring the corresponding LES pressure.

TABLE 3

| Phase # | Electrical Stimulation Type | Pulse Frequency | Pulse Duration | Pulse Amplitude |
|---|---|---|---|---|
| 1 | Short Pulse | 20 Hz | 200 μsec | 5 mAmp |
| 2 If #1 reaches ≤25 mmHg | Short Pulse | 20 Hz | 200 μsec | 3 mAmp |
| 3 If #1 does not reach ≤25 mmHg | Short Pulse | 20 Hz | 200 μsec | 7 mAmp |

TABLE 3-continued

| Phase # | Electrical Stimulation Type | Pulse Frequency | Pulse Duration | Pulse Amplitude |
|---|---|---|---|---|
| 4 If #3 does not reach ≤25 mmHg | Short Pulse | 20 Hz | 200 μsec | 10-15 mAmp |
| 5 | Intermediate Pulse | 20 Hz | 3 ms | 3-15 mAmp using the same sequence as 1-4 |
| 6 | Optimal Pulse | 20 Hz | Optimal Pulse | Optimal amplitude |

As shown above, each of phases 1-4 is applied for 20-30 minutes with a 20-30 minute interval between sessions. The pulse increments can range from 0.1 mAmp to 15 mAmp. The pulse in Phase 6 is intermittently applied for 5 hours, during which stimulation is turned on until pressure is less than or equal to 25 mmHg for at least 5 minutes (on period) and then turned off until pressure rises to greater than 25 mmHg or patient's baseline, whichever is higher (off period), and then turned on again until it is less than or equal to 25 mmHg again (on period), repeating thereafter. These on-off sessions continue while the time durations are recorded. These recorded periods are then used to determine the optimal duty cycle for the patient during the treatment phase (patient-specific LES-EST). It should be appreciated that, if a subject experiences pain or discomfort for any given stimulation sequence, the pulse amplitude is decreased in 1 mAmp increments until stimulation is tolerable. Once the effective tolerable setting is established, the patient-specific LES-EST is initiated with the defined stimulation parameters, as determined by the parameter setting stage described above. Preferably, the patient-specific LES-EST is checked at a set schedule (every 6 months or once a year) or when a patient starts reporting achalasia symptoms using manometry and the patient-specific LES-EST parameters are then modified to achieve ideal LES pressure.

It should be appreciated that the aforementioned diagnostic processes account for a plurality of variables that substantially affect treatment quality, treatment efficacy, and patient compliance, including, but not limited to, patient's disease condition and the corresponding stimulation energy level and frequency required to achieve a positive therapeutic effect, patient willingness to manually apply stimulation, and form factor of the stimulation source, among other variables.

The variables generated in the course of the diagnostic processes can be used to automatically program a controller, which may be used to control a stimulator. In one embodiment, a diagnostic terminal executing on a conventional computer generates at least one variable, such as stimulation pulse width, frequency, amplitude, ramp rate, or a duty cycle, that substantially affects treatment quality, treatment efficacy, and patient compliance, including, but not limited to, patient's disease condition and the corresponding stimulation energy level and frequency required to achieve a positive therapeutic effect, patient willingness to manually apply stimulation, and form factor of the stimulation source, among other variables. The diagnostic terminal is in data communication with a controller configuration terminal that electronically receives a controller into an interface or wirelessly communicates with the controller that is responsible for executing the stimulation parameters. Upon generating the variables, the diagnostic terminal transmits the variables, which are eventually received by the controller and saved in an appropriate memory location. The controller then uses the variables to control one or more stimulation settings.

In another embodiment, the stimulation parameters are checked by a physician using a data terminal, such as a laptop, tablet computer, mobile device, or personal computer. As discussed above, data relevant to the efficacy of the stimulation parameters can be wirelessly obtained from the stimulation device memory or from a patient controlled computing device, such as a tablet computer, laptop, personal computer, or mobile device. The physician can modify the stimulation parameters in accordance with the received data and, using the data terminal, issue modified stimulation parameters to the controller of a stimulator as described above.

Exemplary Therapies

The following description is intended to provide examples of how the therapies, described above, may be specifically implemented. They should not be viewed as limiting the general scope of the inventions described herein.

Therapy One: Patient Timed and Delivered Stimulation Using a Handheld Device

In a first therapy, a patient can be effectively therapeutically treated with intermittent wireless short bursts of stimulation applied a plurality of times during a day. For example, in one embodiment, a patient can be treated by applying a burst of stimulation for a period of five minutes or less at a frequency of 5 times or less per day. In another embodiment, the stimulation occurs less than 5 times a day for a period of 30 minutes or less per stimulation. This stimulation frequency is effective to treat certain symptoms of a patient, including diminishing or eliminating a patient's achalasia.

Figure 10:
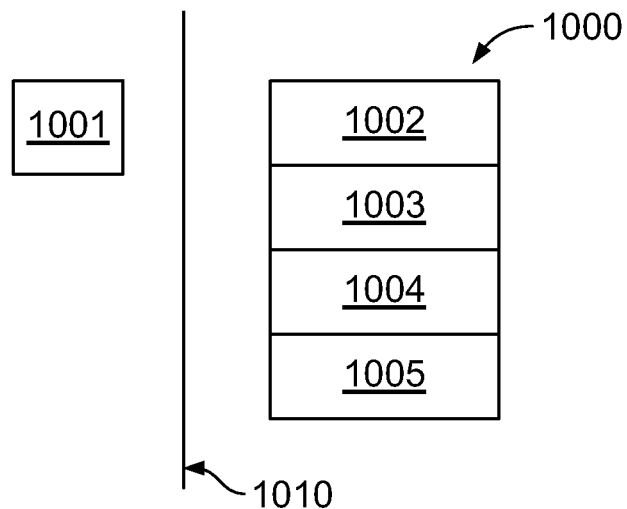
FIG. 10 is a block diagram depicting the modules of an exemplary embodiment of the stimulating device of the present specification.

In this treatment method, a patient can be effectively treated by having the patient apply an external power source over a predefined area on the patient's body and manually initiate stimulation. FIG. 10 is one embodiment of a block diagram of certain modules of a stimulating device of the present specification. In one embodiment, the stimulation system comprises a stimulation source 1000 and a microstimulator 1001. The stimulation source 1000 comprises a controller 1002, transducer 1003, waveform generator 1004, and power source 1005, such as a battery. The stimulation source 1000 directs energy, such as ultrasound or RF energy, across the patient's skin 1010 and toward a microstimulator 1001 that is implanted directly on the site being stimulated. The stimulation source 1000 can generate a plurality of different pulse widths, amplitudes, frequencies, or combinations thereof, as further described below.

In certain situations, the device may require an energy supply to power the implantable pulse generator, but it is difficult or undesirable to include an implantable battery that would be wired to the device due to size limitations, restrictions arising from the implant location, or the need to decrease device costs. In one embodiment, a rechargeable battery is wired to the stimulator. The rechargeable battery stores a smaller amount of charge, and therefore can be small in size, but is configured or adapted to be replenished using wireless transmission of energy.

In another embodiment that requires an implanted device size which is even smaller than that which is possible with a rechargeable battery and associated recharging circuit, the device comprises a passive circuit that receives, in real time, transmitted wireless energy from a transmission source external to the patient. The implanted passive circuit would control the extraction of the transmitted energy and the delivery of the energy to the rest of the stimulator device. The external energy transmission device would control the timing of stimulation and any sensing and/or triggering mechanisms related thereto. One limitation to the wireless transmission of energy is the amount of energy that can be wirelessly transmitted in any given time due to, for example, safety or interference requirements. Such wireless energy transmission limitations narrow the applicable stimulation amplitude and waveform that can be applied to the tissue, thereby limiting the clinical application and benefit of such systems.

In another embodiment, the microstimulator comprises a means for storing a charge locally, such as a short-term energy storage component or a capacitor, and an associated trigger mechanism. During an on-off duty cycle for stimulating the microstimulator, the off-time of the stimulation duty cycle can be used to temporarily store a charge, thereby enhancing the maximal amplitude and variety of waveform that can be applied. The implanted device circuit is configured to control and time the stimulation in response to energy or control information from a controller that is external to the patient and communicates wirelessly with the implanted device. The implanted circuit extracts the transmitted energy or control information and, in response thereto, shapes the waveform within the off-time of each stimulation cycle using components such as capacitors, diodes, inductors, transistors and resistors.

The operating characteristics of a capacitor integrated with, or local to, the implanted device will be determined, at least in part, by the required pulse duration and the ratio of required stimulation pulse amplitude to minimal expected extracted supply current within the implantable device. The capacitor characteristics will also be a function of the load impedance. For example, assuming a required pulse duration of 200 μs to be applied every 50 ms and a required amplitude of 10 mAmp, the device will need to provide a charge of 2 μC (10 mAmp×200 μs). Assuming an impedance of 100 ohms with a voltage of 1 V (10 mAmp×100 ohm), then the minimum required capacitor will have a value as approximated by the following equation:

$$C = Q/V = 2uC/1V = 2\ uF$$

This value will need to be adjusted so that it is not fully discharged during stimulation and to compensate for losses within the implantable device. For an overall cycle of, for example, 50 ms, the theoretical minimal extracted supply current that can drive the required pulse will be:

Minimal extracted current=10 mAmp×200 μs/(50 ms−200 μs)=0.04 mAmp

Adjusting for internal losses within the stimulator will yield a practical limit of about 0.1 mAmp or 100 μAmp. Higher available supply currents can allow for shorter cycles or longer pulse duration as necessary and can be extrapolated from the above.

In one embodiment, energy need not be stored between cycles and the passive circuit responds, in real-time, to the wireless transmission of energy. For example, the implanted circuit may initiate a stimulation pulse in response to a stimulation pulse wirelessly sent by the external energy transmitting unit, where the energy transmission is above a pre-defined time period, is characterized by the intermittent ceasing of energy transmission, or is characterized by another combination of "on"-"off" energy signals.

In one embodiment, the stimulation source 1000 directs ultrasonic energy to the microstimulator 1001 which comprises an ultrasonic receiver. The microstimulator 1001 is implanted into the area to be stimulated via an endoscope. The microstimulator 1001 can function either as a pass-through for energy and stimulation parameters or comprise an energy storage and programmatic memory to deliver short stimulation bursts, using the stored energy, at predetermined time intervals, pursuant to the programmed memory.

In one embodiment, the stimulation source 1000 directs radio frequency (RF) energy to the microstimulator 1001 which comprises an RF receiver. The microstimulator 1001 is implanted into the area to be stimulated via an endoscope. The microstimulator 1001 can function either as a pass-through for energy and stimulation parameters or comprise an energy storage and programmatic memory to deliver short stimulation bursts, using the stored energy, at predetermined time intervals, pursuant to the programmed memory.

In one embodiment, the stimulation source 1000 comprises a controller 1002, transducer 1003, waveform generator 1004, and power source 1005, such as a battery. Operationally, the controller 1002, via a processor in data communication with a memory storing programmatic instructions, causes the waveform generator 1004 to generate a predefined waveform, having an associated pulse width, amplitude, and frequency, which is transmitted via the transducer 1003 to the endoscopically implanted microstimulator 1001. A patient applies the stimulation source 1000 intermittently for a short time period, preferably 30 minutes or less, over the microstimulator 1001 site. Where the microstimulator 1001 comprises a local memory for storing programmatic instructions, in particular stimulation parameters and processes, the stimulation source 1000 need not comprise a controller and memory for storing such programmatic instructions and may simply transmit a predefined amount of energy to the micro stimulator.

Figure 11:
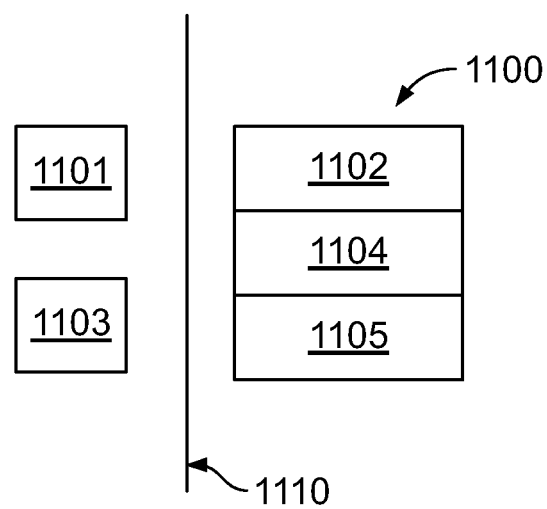
FIG. 11 is a block diagram depicting the modules of another exemplary embodiment of the stimulating device of the present specification.

In another embodiment, referring to FIG. 11, the stimulation source 1100 comprises a controller 1102, waveform generator 1104, and power source 1105, such as a battery. It wirelessly communicates with, and/or transfers energy to, a transducer 1103 that is implanted subcutaneously. The subcutaneous transducer 1103 receives the wirelessly transmitted energy, such as RF or ultrasound, through the patient's skin surface and transmits it, via a wired or wireless connection, to an endoscopically implanted microstimulator 1101. Operationally, the controller 1102, via a processor in data communication with a memory storing programmatic instructions, causes the waveform generator 1104 to generate a predefined waveform, having an associated pulse width, amplitude, and frequency, which is transmitted wirelessly into the patient's subcutaneous region and into the transducer 1103, which further transmits the energy to the microstimulator 1101. A patient applies the stimulation source 1100 intermittently for a short time period, preferably thirty minutes or less, over the transducer site. Where the microstimulator 1101 comprises a local memory for storing programmatic instructions, in particular stimulation parameters and processes, the stimulation source 1100 need not comprise a controller and memory for storing such programmatic instructions and may simply transmit a predefined amount of energy to the transducer 1103 and, thus, to the microstimulator 1101. It should be appreciated that, regardless of the type, the stimulation source 1100 can be integrated into a plurality of different housings, including a miniature flashlight, cell phone case, or smart card. In one embodiment, the subcutaneous transducer 1103 receives lower frequency electro-magnetic energy and commands from the stimulation source 1100 and converts the energy into high frequency RF energy. The frequency conversion will be less efficient than direct RF transmission but the use of the subcutaneous transducer will assist in eliminating heating issues. In addition, the subcutaneous transducer can also be used as a simple energy storage unit. In another embodiment, the subcutaneous transducer 1103 receives lower frequency electro-magnetic energy and commands from the stimulation source 1100 and converts the energy into ultrasound energy.

Figure 12:
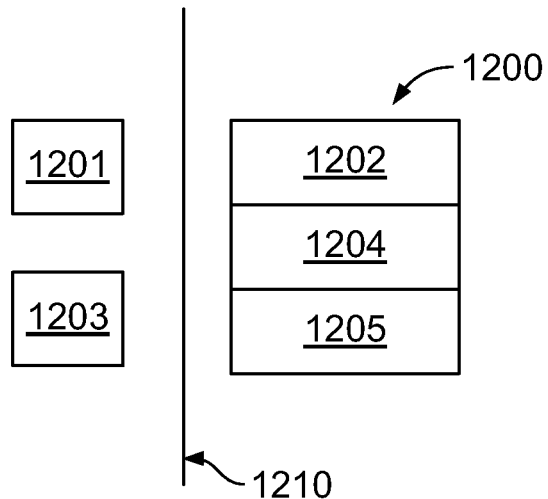
FIG. 12 is a block diagram depicting the modules of another exemplary embodiment of the stimulating device of the present specification.

In another embodiment, referring to FIG. 12, a patient is treated by laparoscopically implanting a plurality of electrodes 1201 (within the anatomical area to be stimulated) in wired communication with a transducer 1203 (comprising an antenna) proximate the skin surface. The transducer 1203 wirelessly communicates with an external energy source 1200 (comprising a controller 1202, waveform generator 1204, and power source 1205, such as a battery) across the surface of the patient's skin 1210. The external energy source 1200 can be applied to the stimulation site by a patient, as described above. With close energy source application, radio frequency, ultrasound, or inductive/magnetic energies can be used.

Referring to FIGS. 10-12 simultaneously, as further discussed below, the stimulation source 1000, 1100, 1200 can initiate or terminate stimulation, when properly placed over the appropriate site, based on any of a plurality of triggers, including manually by a patient, patient activity, or other sensed patient states. The stimulation source 1000, 1100, 1200 can generate a plurality of different pulse widths, amplitudes, frequencies, or combinations thereof, as further described below.

Therapy Two: Controller Timed and Delivered Stimulation

In a second therapy, a patient may not be effectively therapeutically treated with intermittent wireless short bursts of stimulation applied a plurality of times during a day. Rather, a patient requires bursts of stimulation for a period greater than a predefined period of time, or for a frequency of more than a predefined number of times per day. Accordingly, a patient is subjected to stimulation that is initiated, effectuated, or otherwise triggered by a programmed controller. This more frequent, or continuous, stimulation is effective to treat certain symptoms of a patient, including treatment of achalasia, or reaching a predetermined LES pressure, muscle tension or electrode impedance.

Figure 13:
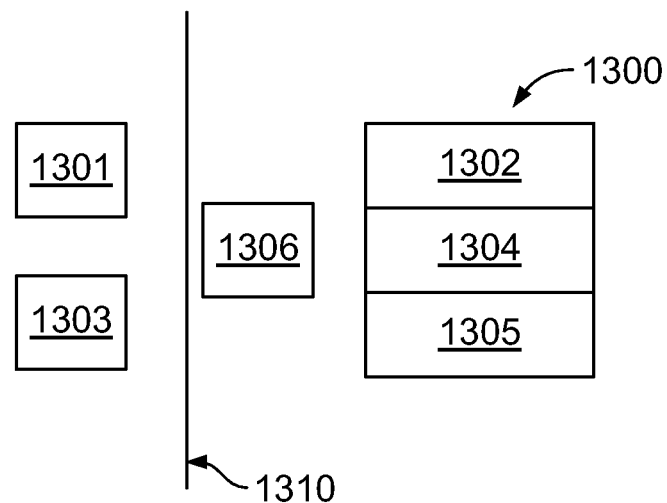
FIG. 13 is a block diagram depicting the modules of another exemplary embodiment of the stimulating device of the present specification.

In this treatment method, a patient can be effectively treated by a plurality of embodiments, including:

1) Referring to FIG. 13, endoscopically implanting a microstimulator 1301 (having a receiver and placed within the anatomical area to be stimulated) in wireless or wired communication with a subcutaneously implanted transducer 1303 that, in turn, wirelessly communicates with a transducer 1306 (comprising at least one antenna and an adhesive surface) applied to the patient's skin surface 1310, which is wired to, and receives signals from, a stimulator source 1300 (comprising a controller 1302, waveform generator 1304, and power source 1305, such as a battery). The controller 1302 can be programmed to initiate or terminate stimulation based on a plurality of patient-specific triggers, such as pH level, LES pressure, fasting state, eating state, sleeping state, physical incline, or patient activity state, among other triggers as further described below. The stimulation source 1300 can generate and transmit radio frequency or ultrasound energy and can generate a plurality of different pulse widths, amplitudes, frequencies, or combinations thereof, as further described below. In one embodiment, the radio frequency or ultrasound pulse is designed to operate over a wireless distance of 6 inches or less, through the human body, with a maximum pulse amplitude of 10 mAmp and a maximum pulse width of 10 msec. It should be appreciated that if one parameter is lowered, such as the wireless distance (lowering it to one inch), another parameter can be modified accordingly, such as the amplitude (increasing it to 30 mAmp).

Figure 14:
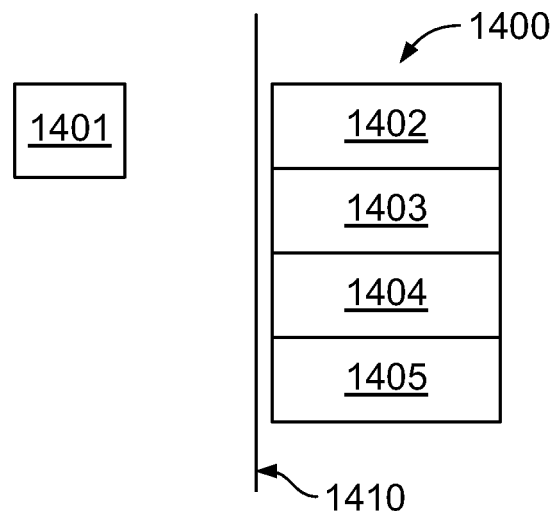
FIG. 14 is a block diagram depicting the modules of another exemplary embodiment of the stimulating device of the present specification.

2) Referring to FIG. 14, endoscopically implanting a microstimulator 1401 (having a receiver and placed within the anatomical area to be stimulated) in wireless communication with a stimulator source 1400 (comprising a controller 1402, transducer 1403, waveform generator 1404, and power source 1405, such as a battery) and which is held against a patient's skin 1410 over the microstimulator site with straps, adhesives, garments, or bindings. The controller 1402 can be programmed to initiate or terminate stimulation based on a plurality of patient-specific triggers, such as pH level, LES pressure, fasting state, eating state, sleeping state, physical incline, or patient activity state, among other triggers as further described below. The stimulation source 1400 can generate and transmit radio frequency or ultrasound energy and can generate a plurality of different pulse widths, amplitudes, frequencies, or combinations thereof, as further described below. In one embodiment, the radio frequency or ultrasound pulse is designed to operate over a wireless distance of 6 inches or less, through the human body, with a maximum pulse amplitude of 10 mAmp and a maximum pulse width of 10 msec. It should be appreciated that if one parameter is lowered, such as the wireless distance (lowering it to one inch), another parameter can be modified accordingly, such as the amplitude (increasing it to 30 mAmp).

Figure 15:
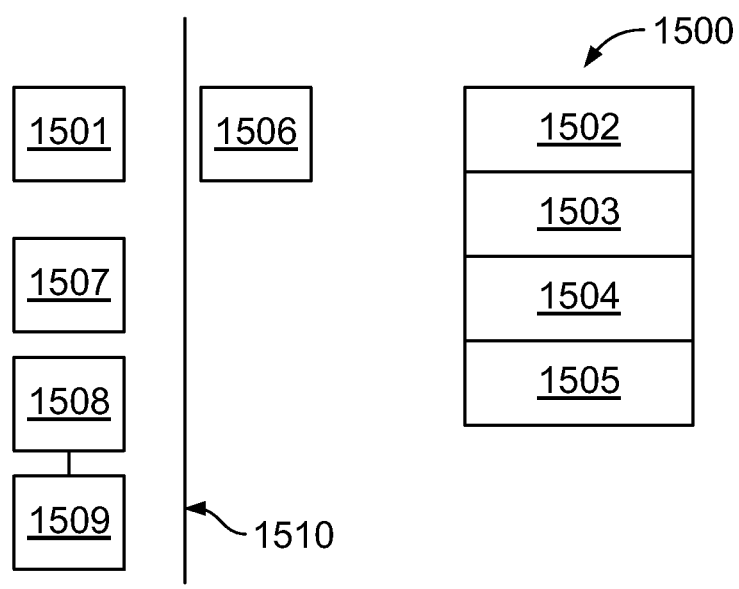
FIG. 15 is a block diagram depicting the modules of another exemplary embodiment of the stimulating device of the present specification.

3) Referring to FIG. 15, endoscopically implanting a microstimulator 1501 (having a receiver and placed within the anatomical area to be stimulated) in wireless communication with a relay device 1506 worn over the stimulation site 1510, that is in wired communication with an external stimulator 1500. The external stimulator 1500 is in wireless communication with an implanted adapter 1507, which is in wireless communication with an external stimulator 1500, or in wireless communication with an implanted transducer 1508 that is in wired communication, via an electrode, to an implanted stimulator 1509. The stimulator 1500 (comprising a controller 1502, transducer 1503, waveform generator 1504, and power source 1505, such as a battery) can be programmed to initiate or terminate stimulation based on a plurality of patient-specific triggers, such as pH level, LES pressure, fasting state, eating state, sleeping state, physical incline, or patient activity state, among other triggers as further described below. The stimulation source 1500 can generate and transmit radio frequency or ultrasound energy and can generate a plurality of different pulse widths, amplitudes, frequencies, or combinations thereof, as further described below. In one embodiment, the radio frequency or ultrasound pulse is designed to operate over a wireless distance of 6 inches or less, through the human body, with a maximum pulse amplitude of 10 mAmp and a maximum pulse width of 10 msec. It should be appreciated that if one parameter is lowered, such as the wireless distance (lowering it to one inch), another parameter can be modified accordingly, such as the amplitude (increasing it to 30 mAmp).

Figure 16:
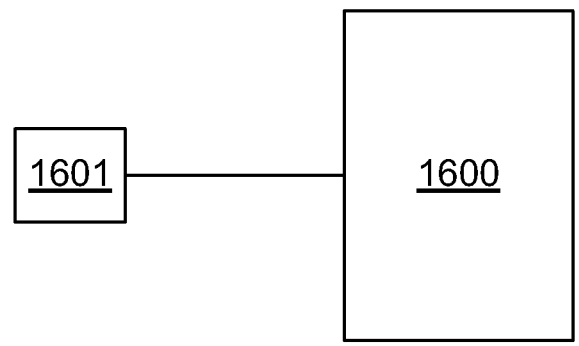
FIG. 16 is a block diagram depicting the modules of another exemplary embodiment of the stimulating device of the present specification.

4) Referring to FIG. 16, laparoscopically implanting a plurality of electrodes 1601 (within the anatomical area to be stimulated) in wired communication with an implanted stimulator 1600 (comprising a primary cell that provides energy and a memory with programmatic instructions for defining appropriate stimulation parameters) which can be programmed to generate stimulation either continuously or periodically based on a predefined program or based on patient-specific triggers, such as pH level, LES pressure, LES impedance, fasting state, eating state, sleeping state, physical incline, or patient activity state, among other triggers as further described below. In one embodiment, the stimulator 1600 wirelessly receives control data or information from an external device, which is controlled, at least in part, by a physician or patient. The stimulator 1600 can generate a plurality of different pulse widths, amplitudes, frequencies, or combinations thereof, as described above.

Figure 17:
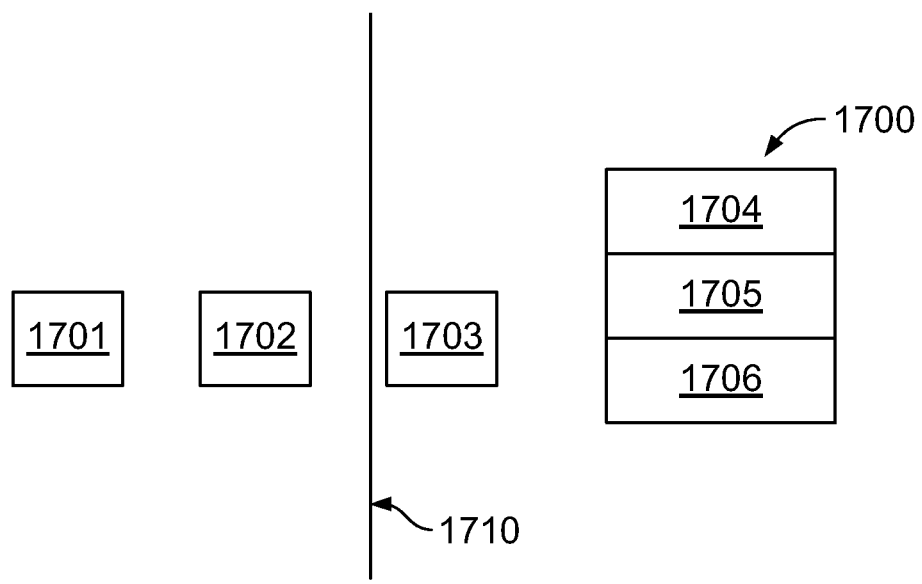
FIG. 17 is a block diagram depicting the modules of yet another exemplary embodiment of the stimulating device of the present specification.

5) Referring to FIG. 17, laparoscopically implanting a plurality of electrodes 1701 (within the anatomical area to be stimulated) in wired communication with a subcutaneously implanted transducer 1702 that, in turn, wirelessly communicates with a stimulator source or a transducer 1703 (comprising at least one antenna and an adhesive surface) applied to the patient's skin surface 1710 which is wired to, and receives signals from, a stimulator source 1700 (comprising a controller 1704, waveform generator 1705, and power source 1706, such as a battery). The controller 1704 can be programmed to initiate or terminate stimulation based on a plurality of patient-specific triggers, such as pH level, LES pressure, fasting state, eating state, sleeping state, physical incline, or patient activity state, among other triggers as further described below. The stimulation source 1700 can generate and transmit radio frequency or ultrasound energy and can generate a plurality of different pulse widths, amplitudes, frequencies, or combinations thereof, as further described below.

It should be appreciated that, while the disclosed system can use RF, inductive coupling, magnetic coupling or ultrasound, in one embodiment, the system can combine the use of RF inductive coupling, magnetic coupling, and ultrasound to take best advantage of transmission efficiencies in various media. In one embodiment, the external stimulator source generates RF waveforms, which wirelessly transmit RF energy to an intermediary receiver that can be implanted subcutaneously and that converts the received RF energy into an ultrasound waveform. The intermediary receiver has an RF receiver, an ultrasound waveform generator, and an ultrasound transmitter. In another embodiment, the device comprises a means for storing a charge locally, such as a short-term energy storage component (capacitor), and an associated trigger mechanism, as described above.

It should be appreciated that the microstimulator (or, where a laparoscopically implanted stimulation electrode and stimulator are used, the stimulator) can locally store energy, be used with RF or US, and rely on an external device for stimulation control and/or energy recharge. Specifically, the microstimulator can comprise a means for storing a charge locally, such as a capacitor. It should further be appreciated that the anatomical region to be stimulated, such as the LES, areas within 2 cm of the LES, the esophagus, or the UES, may be stimulated using a plurality of microstimulators or electrodes, including an array of microstimulators or electrodes affixed to a mesh or other substrate. It should further be appreciated the microstimulator or implanted stimulator can store enough energy to function as a backup, or otherwise fill in gaps in energy transfer from an external source when, for example, wireless transmission coupling is interrupted or inefficient. In another embodiment, the microstimulator or implanted stimulator receives an energy stream from an external stimulator and, in real-time, forms the requisite waveform based on parameters encoded in a wireless control stream or embedded in the energy stream. In another embodiment, the microstimulator or implanted stimulator receives a pre-formed waveform from an external stimulator.

As discussed above, the endoscopic therapeutic treatments are part of the diagnosis process in which a microstimulator is endoscopically implanted and used in combination with an external device for an initial period. Data is gathered regarding frequency of stimulation required, amount of energy required, and other factors. A patient then receives a laparoscopically implanted permanent system operating in accordance with the gathered data.

The above examples are merely illustrative of the many applications of the system of the present invention. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

We claim:

1. A method for treating esophageal dysfunction and preventing a hiatal hernia in a patient, comprising:
   providing a device comprising at least one electrode operably connected to a pulse generator, and an energy source, said device adapted to apply electrical stimulation to a target tissue, wherein the at least one electrode is positioned on a first end of the device and the pulse generator is positioned on a second end of the device;
   implanting said device within a gastrointestinal tract of the patient, wherein the first end of the device is implanted in a portion of esophageal tissue of the patient and said at least one electrode is positioned to be in electrical communication with a lower esophageal sphincter of the patient, wherein the second end of the device is implanted in an abdomen of the patient, and wherein said device is implanted such that a slack in a range of 1 cm to 10 cm exists between said first end and said second end; and
   operating said device to cause electrical stimulation to be applied to the patient's lower esophageal sphincter muscle to modulate function of said lower esophageal sphincter muscle, wherein said operation is not dependent upon, influenced by, modified by, lengthened by, or shortened by a physiological state of a patient.

2. The method for treating esophageal dysfunction and preventing a hiatal hernia of claim 1, further comprising the step of incising a muscle of the lower esophageal sphincter of said patient to eliminate tone of said muscle.

3. The method for treating esophageal dysfunction and preventing a hiatal hernia of claim 1, wherein operating said device to apply electrical stimulation to said lower esophageal sphincter further effectuates an increase in peristaltic activity within the esophageal tissue.

4. The method for treating esophageal dysfunction and preventing a hiatal hernia of claim 1, wherein said esophageal dysfunction comprises any one or more of achalasia, pain with swallowing, stasis, and/or regurgitation.

5. The method for treating esophageal dysfunction and preventing a hiatal hernia of claim 1, wherein said esophageal tissue comprises any one or more of the proximal, mid, distal esophagus and/or LES.

6. The method for treating esophageal dysfunction and preventing a hiatal hernia of claim 1, wherein said operation defines, uses, or is dependent upon a plurality of stimulation parameters that are selected, derived, obtained, calculated, or determined, at least in part, to avoid lower esophageal sphincter fatigue and tolerance.

7. The method for treating esophageal dysfunction and preventing a hiatal hernia of claim 1, wherein said operation defines, uses, or is dependent upon a plurality of stimulation parameters that are selected, derived, obtained, calculated, or determined, at least in part, to account for a latent, delayed, time-delayed, or future response of the lower esophageal sphincter of the patient.

8. The method for treating esophageal dysfunction and preventing a hiatal hernia of claim 4, further wherein said operation is initiated prior to a pre-defined point in time wherein said pre-defined point in time is associated with an achalasia triggering event and wherein said initiation occurs prior to said pre-defined point in time by a minimum time period.

9. The method for treating esophageal dysfunction and preventing a hiatal hernia of claim 8, wherein said minimum time period is at least 5 minutes, 10 minutes, 15 minutes, 30 minutes, 1 hour, 2 hours, 3 hours, 12 hours, 24 hours, or any time increment therein.

10. The method for treating esophageal dysfunction and preventing a hiatal hernia of claim 8, wherein the electrical stimulation is terminated after said pre-defined point in time has passed.

11. The method for treating esophageal dysfunction and preventing a hiatal hernia of claim 1, wherein said operation is performed in accordance with at least one on period, wherein said on period is between 1 second and 24 hours and at least one off period, wherein said off period is greater than 10 seconds.

12. The method for treating esophageal dysfunction and preventing a hiatal hernia of claim 1, wherein a current of the electrical stimulation from said at least one electrode ranges from greater than or equal to 8 mAmp to less than or equal to 1 Amp.

13. The method for treating esophageal dysfunction and preventing a hiatal hernia of claim 1, wherein a pulse duration of the electrical stimulation from said at least one electrode ranges from greater than or equal to 100 μsec to less than or equal to 1 second.

14. A system for treating esophageal dysfunction in a patient, comprising:
a pulse generator in electrical communication with, and physically attached to, at least one electrode, wherein said pulse generator is positioned on a first end of a strap and is configured to be implanted within the patient's abdomen, wherein said at least one electrode is positioned on a second end of said strap and is configured to be implanted in esophagus tissue of the patient, wherein, upon implantation, said at least one electrode and said pulse generator are separated by a slack in a range of 1 cm to 10 cm, and wherein said pulse generator with said at least one electrode provide electrical stimulation to the proximate, mid, or distal esophagus or LES to effectuate a decrease in LES tone and pressure and/or an increase in esophageal peristalsis;
a controller module wired or wirelessly connected to said pulse generator, said controller module capable of receiving, storing and transmitting programmatic instructions directed toward the operation of said pulse generator; and
an energy storage component, wherein said energy storage component is integrated with said pulse generator or with said controller and is configured to be independently implanted within the patient or secured outside the patient against the patient's skin, wherein said operation is not dependent upon, influenced by, modified by, lengthened by, or shortened by a physiological state of the patient.

15. The system for treating esophageal dysfunction and preventing a hiatal hernia in a patient of claim 14, wherein said esophageal dysfunction comprises any one or more of achalasia, pain with swallowing, stasis, and/or regurgitation.

* * * * *